United States Patent
Krueger

(10) Patent No.: US 9,788,714 B2
(45) Date of Patent: Oct. 17, 2017

(54) SYSTEMS AND METHODS USING VIRTUAL REALITY OR AUGMENTED REALITY ENVIRONMENTS FOR THE MEASUREMENT AND/OR IMPROVEMENT OF HUMAN VESTIBULO-OCULAR PERFORMANCE

(71) Applicant: Wesley W. O. Krueger, San Antonio, TX (US)

(72) Inventor: Wesley W. O. Krueger, San Antonio, TX (US)

(73) Assignee: IARMOURHOLDINGS, INC., San Antonio, TX (US)

( * ) Notice: Subject to any disclaimer, the term of this patent is extended or adjusted under 35 U.S.C. 154(b) by 0 days.

(21) Appl. No.: 15/162,300

(22) Filed: May 23, 2016

(65) Prior Publication Data

US 2016/0262608 A1    Sep. 15, 2016

Related U.S. Application Data

(63) Continuation-in-part of application No. 14/326,335, filed on Jul. 8, 2014, now Pat. No. 9,370,302.

(51) Int. Cl.
*A61B 3/14* (2006.01)
*A61B 3/00* (2006.01)
(Continued)

(52) U.S. Cl.
CPC ............ *A61B 3/0041* (2013.01); *A61B 3/032* (2013.01); *A61B 3/113* (2013.01); *A61B 3/18* (2013.01);
(Continued)

(58) Field of Classification Search
USPC .................................................. 351/200–246
See application file for complete search history.

(56) References Cited

U.S. PATENT DOCUMENTS 4,817,633 A    4/1989  McStravick et al.
5,180,907 A    1/1993  Udden et al.
(Continued)

FOREIGN PATENT DOCUMENTS

WO    WO 2013117727    8/2013

OTHER PUBLICATIONS

Allison et al, Combined Head and Eye Tracking System for Dynamic Testing of the Vestibular System. IEEE Transactions on Biometical Engineering, vol. 43, No. 11 Nov. 1996. (USA).

*Primary Examiner* — Mohammed Hasan
(74) *Attorney, Agent, or Firm* — Kilpatrick Townsend & Stockton LLP

(57) ABSTRACT

A system and method for using a virtual reality or an augmented reality environment for the measurement and/or improvement of human vestibulo-ocular performance can be implemented by combining a video camera based eye orientation sensor, a head orientation sensor, a display, and an electronic circuit that connects the eye sensor, head sensor, and display. The system and method can be operated in the range of frequencies between 0.01 Hertz and 15 Hertz. The system and method can use a Fourier transform to compute a gain and a phase. The system and method can be used for measuring vestibulo-ocular reflex, dynamic visual acuity, dynamic visual stability, kinetic visual acuity, retinal image stability, or foveal fixation stability in a non-clinical setting. The system and method can be completely portable, head-worn, and self-contained.

24 Claims, 13 Drawing Sheets

(51) Int. Cl.
- A61B 5/00 (2006.01)
- A61B 3/032 (2006.01)
- G06T 19/00 (2011.01)
- G02B 27/01 (2006.01)
- G06F 3/01 (2006.01)
- A61B 3/113 (2006.01)
- A61B 3/18 (2006.01)
- A61B 5/11 (2006.01)
- A61B 3/11 (2006.01)

(52) U.S. Cl.
CPC .............. *A61B 5/11* (2013.01); *A61B 5/4023* (2013.01); *A61B 5/4064* (2013.01); *A61B 5/6803* (2013.01); *A61B 5/7257* (2013.01); *A61B 5/744* (2013.01); *G02B 27/017* (2013.01); *G06F 3/012* (2013.01); *G06T 19/006* (2013.01); *A61B 3/112* (2013.01); *G06F 3/013* (2013.01)

(56) References Cited

U.S. PATENT DOCUMENTS

| | | |
|---|---|---|
| 5,550,601 A | 8/1996 | Donaldson |
| 5,555,895 A | 9/1996 | Ulmer et al. |
| 5,838,420 A | 11/1998 | MacGregor Donaldson |
| 5,919,149 A | 7/1999 | Allum |
| 5,942,954 A | 8/1999 | Galiana et al. |
| 5,953,102 A | 9/1999 | Berry |
| 6,796,947 B2 | 9/2004 | Watt et al. |
| 7,380,938 B2 | 6/2008 | Chmielewski et al. |
| 7,401,920 B1 | 7/2008 | Kranz et al. |
| 7,448,751 B2 | 11/2008 | Kiderman et al. |
| 7,500,752 B2 | 3/2009 | Nashner |
| 7,651,224 B2 | 1/2010 | Wood et al. |
| 7,682,024 B2 | 3/2010 | Plant et al. |
| 7,727,162 B2 | 6/2010 | Peterka |
| 7,731,360 B2 | 6/2010 | MacDougall et al. |
| 7,753,523 B2 | 7/2010 | Kiderman et al. |
| 7,866,818 B2 | 1/2011 | Schroeder et al. |
| 7,931,370 B2 | 4/2011 | Bartomeu |
| 7,988,287 B1 | 8/2011 | Butler et al. |
| 8,253,814 B2 | 8/2012 | Zhang et al. |
| 8,285,416 B2 | 10/2012 | Cho et al. |
| 8,510,166 B2 | 8/2013 | Neven |
| 8,529,463 B2 | 9/2013 | Della Santina et al. |
| 8,696,126 B2 | 4/2014 | Yoo et al. |
| 8,764,193 B2 | 7/2014 | Kiderman et al. |
| 2002/0118339 A1 | 8/2002 | Lowe |
| 2006/0098087 A1 | 5/2006 | Brandt et al. |
| 2006/0206175 A1* | 9/2006 | Fernandez Tournier ........... A63B 26/003 607/88 |
| 2006/0270945 A1 | 11/2006 | Ghajar |
| 2009/0021695 A1 | 1/2009 | Scarpino |
| 2010/0036289 A1 | 2/2010 | White et al. |
| 2010/0092049 A1 | 4/2010 | Schroeder et al. |
| 2010/0198104 A1 | 8/2010 | Schubert et al. |
| 2010/0280372 A1 | 11/2010 | Poolman et al. |
| 2011/0176106 A1 | 7/2011 | Lewkowski |
| 2012/0133892 A1 | 5/2012 | Furman et al. |
| 2013/0278899 A1 | 10/2013 | Waldorf et al. |
| 2014/0111771 A1 | 4/2014 | Liu |
| 2014/0192326 A1 | 7/2014 | Kiderman et al. |
| 2014/0327880 A1 | 11/2014 | Kiderman et al. |
| 2015/0038803 A1 | 2/2015 | Uhlig et al. |
| 2015/0223683 A1 | 8/2015 | Davidovics et al. |
| 2015/0243099 A1 | 8/2015 | Schowengerdt |
| 2015/0245766 A1 | 9/2015 | Rennaker et al. |
| 2015/0335239 A1 | 11/2015 | Macfougall |
| 2016/0033750 A1 | 2/2016 | Nunnink et al. |
| 2016/0062459 A1 | 3/2016 | Publicover et al. |
| 2016/0081546 A1 | 3/2016 | MacDougall |
| 2016/0085302 A1 | 3/2016 | Publicover et al. |
| 2016/0106315 A1 | 4/2016 | Kempinski |
| 2016/0110920 A1 | 4/2016 | Schowengerdt |
| 2016/0132726 A1 | 5/2016 | Kempinski et al. |
| 2016/0242642 A1* | 8/2016 | Migliaccio ........... A61B 3/113 |

* cited by examiner

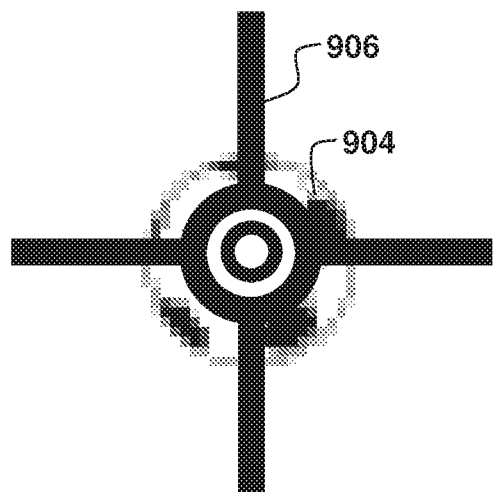
FIG. 11A                FIG. 11B
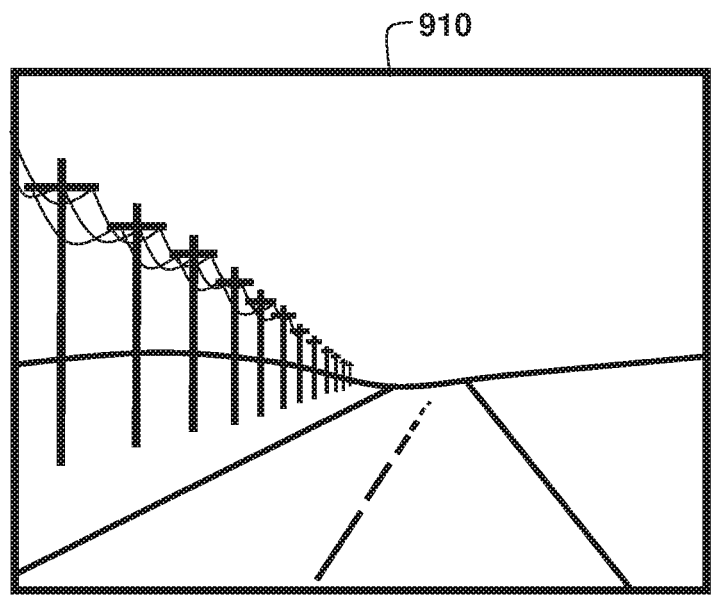
FIG. 12

SYSTEMS AND METHODS USING VIRTUAL REALITY OR AUGMENTED REALITY ENVIRONMENTS FOR THE MEASUREMENT AND/OR IMPROVEMENT OF HUMAN VESTIBULO-OCULAR PERFORMANCE

CROSS REFERENCE TO RELATED APPLICATIONS

This is a Continuation-In-Part of U.S. patent application Ser. No. 14/326,355 filed 8 Jul. 2014 now U.S. Pat. No. 9,370,302 B2, the entire disclosure of which is incorporated by reference herein.

BACKGROUND

The present invention relates to systems and methods that use virtual reality and/or augmented reality environments for the measurement and/or improvement of the human eye response to orientation information that comes from the vestibular system. Terms used to describe this ocular response include dynamic visual acuity (DVA), dynamic visual stability (DVS), kinetic visual acuity (KVA), ocular saccades, retinal image stability (RIS), foveal fixation stability (FFS), vestibulo-ocular reflex, and vestibular ocular reflex. This disclosure and the appended claims use VOP to designate any and all of these measures of vestibular ocular performance. In one embodiment, the present invention comprises a head-worn device for measuring and/or improving a person's VOP by:

(a) presenting visual virtual reality (VR) or augmented reality (AR) information;
(b) tracking head movement; and
(c) tracking eye movement as the visual VR or AR information is presented.

A person's ability to perform physical motion activities depends on his/her oculomotor responses when the body is in motion. The most important of these oculomotor responses is the vestibulo-ocular reflex response, which provides the person with stable images to look at while in motion. When a person does not have a normal VOR, he/she person loses performance in many functions. For example, DVA and FFS test performance deteriorates when the eyes cannot follow the motion of the head. Stated more simply, a person's ability to read while in motion degrades if the vestibulo-ocular reflex cannot compensate for the motion. This vestibulo-ocular performance (VOP) can be evaluated and measured by tracking one or both eyes and the head while a person is watching a display in an AR or VR environment. This VOR can be tested in a variety of ways using tests that can also substitute for the DVA, DVS, RIS, and FFS test methods being used in the prior art.

The vestibular system is regulated by peripheral and central components, each affecting the eye responses with head motion. There are abnormal eye movements associated with both central or peripheral vestibular system disorders. Some of the tests in the prior art and/or tests discussed in this disclosure can be more specific for determining the presence of a peripheral abnormality and some are more specific for identifying central pathology. Measurement of head and eye movements using AR/VR platforms can improve the quality of measurement, which aids the diagnosis of vestibular disorders.

1. DEFINITIONS

The definitions that follow apply to the terminology used in describing the content and embodiments in this disclosure and the related claims.

Vestibulo-ocular refers to the ocular (e.g. human visual motor system) response to stimulus of the vestibular (e.g. inner ear) system, in which the eye movement response is caused by head movement. More specifically, VOR is an involuntary movement of the eyes in response to rotational movements of the head detected by the inner ear balance system. As will be described further in this disclosure, measures of VOP can include gain, phase, symmetry, and saccadic responses to head movements at various frequencies. The VOR stabilizes the visual image on the back of the eye (retina) during head movement by producing an eye movement in the direction opposite to head movement, thus preserving the image on the center of the visual field (e.g. on the fovea). This allows a person to visualize objects clearly during brief head movements. A simplistic view of the VOR involves a 3-neuron arc that consists of the vestibular ganglion, vestibular nuclei, and oculomotor nuclei. When the head moves, the VOR responds with an eye movement that is equal in magnitude but opposite in direction. For example, when the head moves to the right, the eyes move to the left and when the head moves up the eyes move downward. Head movements, rotational and translational, stimulate the VOR. With a rotational movement, the head moves relative to the body. Examples of this include turning the head back and forth, nodding, and bringing the ear in contact with the shoulder. Translational movements occur when the entire body, including the head, is moved in tandem. Translational movements may occur when an individual stands on a moving sidewalk. Thus, rotational VOR responds to angular motion of the head and results from stimulation of the semicircular canals, whereas translational VOR responds to linear motion of the head and results from stimulation of the otolithic organs. Some head movements may involve a combination of both translational VOR and rotational VOR. The VOR is a reflex that acts at short latency to generate eye movements that compensate for head rotations in order to preserve clear vision during locomotion. The VOR is the most accessible gauge of vestibular function. Evaluating the VOR requires application of a vestibular stimulus and measurement of the resulting eye movements. For example, when the head moves to the right, the eyes move to the left, and vice versa. The VOR normally serves to stabilize gaze in space during head movements by generating equal and opposite compensatory eye movements. The VOR has both rotational and translational aspects. When the head rotates about any axis (horizontal, vertical, or torsional) distant visual images are stabilized by rotating the eyes about the same axis, but in the opposite direction. When the head translates, for example during walking, the visual fixation point is maintained by rotating gaze direction in the opposite direction, by an amount that depends on distance. Eye movements generated by the human VOR system are intended to stabilize the image on the retina and specifically on the fovea during brief, non-sustained head movements. In order to see the surrounding world clearly the retinal images on the fovea must remain stable, within certain margins. Stability is affected, however, by the continuous movements of the head, which may cause motion blur. In order to prevent motion blur, head movements are counter-balanced by compensatory eye movements. These are mediated by two reflexes, the VOR, which senses head rotations in the labyrinth, and the optokinetic reflex (OKR), which directly senses visual image motion. Vestibulo-ocular eye movements that reflexively occur in the direction opposite a head movement can also be included within eye signal controls during voluntary head movements. Measurement of the VOR is related to the semicircular canal being tested in the direction of the motion of the head movement. This most often includes both vertical and horizontal VOR tests. Eye-velocity response to the head-velocity stimulus can be seen with the VOR gain for the two directions of rotation and overt and covert saccades can also be identified and measured. During VOR testing, if the person's vestibulo-ocular response is abnormal, then their eyes will be taken off target during the head rotation, because their eyes will not rotate at the correct speed to exactly compensate for head rotation. In this instance, an abnormal VOP means that the eyes can move with the head during a passive unpredictable head turn and will be taken off target by the head turn, so that at the end of the head turn the person must make a corrective saccade toward the target.

The vestibular system can be broadly categorized into peripheral and central components. The peripheral vestibular system is the complex system of the inner ear that helps provide human balance. It is also called the vestibular apparatus and is often referred to as being part of the labyrinth. The peripheral vestibular system is bilaterally composed of three semicircular canals (posterior, superior, lateral) and the otolithic organs (saccule and utricle). The semicircular canals detect rotational head movement while the utricle and saccule respond to linear acceleration and gravity, respectively. These vestibular organs are in a state of symmetrically tonic activity. When excited these vestibular organs stimulate the central vestibular system. The central vestibular pathways (e.g. vestibular nuclei) process this information, along with proprioceptive and ocular input, to maintain our sense of balance and position.

Peripheral vestibular disorders (PVDs) are limited to cranial nerve VIII and all of the inner structures. Persons with a peripheral disorder demonstrate nystagmus to the contralateral side, which suppresses with visual fixation. Nystagmus improves with gaze towards the lesion and worsens with gaze opposite the lesion. Persons may also report a falling sensation. Vegetative symptoms are common. One can expect nausea, vomiting, and possibly sweating and bradycardia. The rate of recovery typically decreases with age and severity, and with the use of vestibulo-suppressive medications. PVDs include pathology of inner ear vestibular structures and the vestibular portion of the eighth cranial nerve. Such pathology diminishes available sensory information regarding head position and movement. These disorders include neuritis, labyrinthitis, bilateral vestibular loss, Meniere's disease, BPPV, and vestibulopathy following surgical procedures.

Central Vestibular Disorders (CVDs) primarily involve the vestibular nuclear complex and the cerebellum, as well as structures of the reticular activating system, midbrain, and higher centers of cortical function. Pathology of the central vestibular structures affects integration and processing of sensory input from the vestibular, visual, and somatosensory systems. The most common CVDs include brainstem strokes, head trauma, migraine-related vestibulopathy, multiple sclerosis, and cerebellar degeneration. Persons with central pathology more often present with complaints of disequilibrium and ataxia rather than true vertigo, but this is not always the case. Often their inability to stand or walk distinguishes them from persons with a peripheral lesion, who more commonly are able to stand or ambulate with assistance. Unlike peripheral lesions, nystagmus of central pathology changes direction with gaze, is unaffected by fixation, and may be purely vertical or torsional.

There can be broad generalizations regarding the symptoms that are more likely to be of peripheral origin compared to those of central origin. When a peripheral lesion is involved, onset is more often sudden and severe with vertigo, where a person reports rotation. Abnormal eye movement, or nystagmus, would be seen accompanying the symptoms of severe vertigo. In contrast, lesions of central origin are usually slow in development, with the person unable to give recall a specific time of onset. The principal symptom is more likely to be that of imbalance and light-headedness with vertigo absent.

Impairment of eye movements, or nystagmus, can be seen in many diseases of the central nervous system, in particular those affecting the brainstem and cerebellum, as well as in those of the vestibular system. Diagnosis for diseases of the central nervous system is made by examination of the different characteristics of eye movements, including: eye position, direction or location along a scan path, velocity of eye movements, range of eye movements, smooth pursuit, point of gaze fixation, fixation duration, static gaze-holding function, and dynamic gaze holding function. CVD diagnosis can also involve testing for the different types of nystagmus (e.g., for example central fixation nystagmus and/or types of movements (fixations and saccades). Depending on the time course of the signs and symptoms, eye movements often indicate a specific underlying cause (e.g., stroke or neurodegenerative or metabolic disorders). For example, isolated dysfunction of vertical eye movements is due to a midbrain lesion affecting the rostral interstitial nucleus of the medial longitudinal fascicle, with impaired vertical saccades only. Gaze-evoked nystagmus (GEN) in all directions indicates a cerebellar dysfunction and can have multiple causes such as drugs, in particular antiepileptics, chronic alcohol abuse, neurodegenerative cerebellar disorders or cerebellar ataxias; purely vertical GEN is due to a midbrain lesion, while purely horizontal GEN is due to a ponto-medullary lesion. The most common pathological types of central nystagmus are downbeat nystagmus (DBN) and upbeat nystagmus (UBN). DBN is generally due to cerebellar dysfunction affecting the flocculus bilaterally (e.g., due to a neurodegenerative disease).

More commonly, with evoked nystagmus of peripheral origin, the nystagmus is mitigated with eye fixation and the nystagmus is enhanced when the fixation is removed. For gaze-evoked nystagmus of central origin, the dominant characteristic is that of direction-changing nystagmus or pure vertical or pure torsional nystagmus. When considering the signs that represent possible central system involvement, abnormalities in pursuit tracking and in random saccade testing are such that they are specific to central system deficits. Spontaneous nystagmus can exist from an acute peripheral lesion or caused by central pathology. It is useful to consider the specific eye movements that are provoked in a normal individual when each of the semicircular canals is individually stimulated. The movements considered below are the compensatory eye movement (slow component of nystagmus), the vestibulo-ocular reflex (VOR), when the canal in question is stimulated, not the beat or fast component.

(a) Horizontal (lateral) canals right and left: VOR response would be to the left and right, respectively.
(b) Anterior (superior) canals right and left: VOR response would be up for both with a torsional movement to the left for the right canal and to the right for the left canal.
(c) Inferior (posterior) canals right and left: VOR response would be down for both with a torsional movement to the left for the right canal and to the right for the left canal.

Using the preceding descriptions of the VOR responses for each of the canals, the only way to produce a down-beating nystagmus from the periphery would be with simultaneous stimulation of both anterior canals. The VOR response would be pure up with the torsional components canceling and the beat would be down. This can occur with both anterior canals that have simultaneous irritative lesions or have simultaneous paretic lesions of both posterior and horizontal canals. A peripheral disorder (bilateral superior canal dehiscence) is also known to produce at least transient pure down-beat nystagmus.

Persons with peripheral labyrinthine lesions can have deficits in smooth pursuit and OKN, but they are rapidly compensated after an acute lesion. By contrast, persons with large, cerebellopontine angle tumors have progressive impairment of pursuit and OKN as the tumor enlarges. Abnormalities of saccadic eye movements suggest intrinsic central nervous system (CNS) dysfunction. Saccade accuracy is severely impaired with cerebellar lesions, while brain stem disease frequently results in a slowing of saccade maximum velocity. Smooth pursuit and OKN abnormalities are common with all types of CNS lesions. The pattern of eye tracking and OKN abnormality can be useful in anatomically localizing nervous system lesions. Persons with downbeat nystagmus suffer from oscillopsia, which leads to an unstable visual perception and therefore impaired visual acuity.

The saccule and utricle collectively comprise what is referred to as the otolith organs. The otolith organs detect position of the head relative to gravity and linear acceleration according to their orientation, when motion occurs in a straight line, to orientate the body in space. The saccule is oriented vertically and registers accelerations in the vertical plane, including the force due to gravity. Therefore, it detects linear motion in the vertical plane, such as ascending or descending in an elevator. It can also provide information about tilting of the head in the vertical plane. When the head moves vertically, the sensory cells of the saccule are disturbed and the neurons connected to them begin transmitting impulses to the brain. These impulses travel along the vestibular portion of the eighth cranial nerve to the vestibular nuclei in the brainstem. The utricle is largely positioned horizontally in the inner ear. The utricle registers accelerations in the horizontal plane of the head, as well as tilt information. Therefore, linear motion in the horizontal plane is sensed, such as moving horizontally in a vehicle. Acute injuries to the utricle are known to cause a subjective tilt of the world. Any orientation of the head causes a combination of stimulation to the utricles and saccules of the two ears. The brain interprets head orientation by comparing these inputs to each other and to other input from the eyes and stretch receptors in the neck, thereby detecting whether only the head is tilted or the entire body is tipping.

The semicircular canals are comprised of three fluid-filled bony channels in the inner ear. The semicircular canals are arranged at right angles to each other and are referred to as the superior (or anterior) semicircular canal, the horizontal (or lateral) semicircular canal and the posterior semicircular canal. Collectively the semicircular canals are referred to as the kinetic labyrinth, because they respond to rotation and angular acceleration. These semicircular canals or channels communicate, by a neural network, with the brain and visual system to provide orientation and balance. Therefore, as a unit, the saccule, utricle and semicircular canals are involved with balance and maintenance of a stable visual image.

A saccade is a fast movement of an eye, head or other part of the body or of a device. It can also be a fast shift in frequency of an emitted signal or other quick change. Saccades are quick, simultaneous movements of both eyes in the same direction. Humans do not look at a scene in fixed steadiness, the eyes move around, locating interesting parts of the scene and building up a mental, three-dimensional 'map' corresponding to the scene. When scanning the scene in front of you or reading these words right now, your eyes make jerky saccadic movements and your eyes stop several times, moving very quickly between each stop. We cannot consciously control the speed of movement during each saccade; the eyes move as fast as they can. One reason for the saccadic movement of the human eye is that the central part of the retina (known as the fovea) plays a critical role in resolving objects. By moving the eye so that small parts of a scene can be sensed with greater resolution, body resources can be used more efficiently. The saccade that occurs at the end of a head turn with someone who has an abnormal VOR is usually a very clear saccade, and it is referred to as an overt saccade. An overt saccade is indicative of abnormal semicircular canal function on the side to which the head was rotated. For example, an overt saccade after a leftwards head rotation means the left semicircular canal has a deficit. Covert saccades are small corrective saccades that occur during the head movement of a person with abnormal inner ear function. Covert saccades reduce the need for overt saccades that the end of the head movement and are more difficult to identify than overt saccades. Covert saccades are very fast. This makes them almost impossible to detect by the naked eye, and therefore sensitive eye tracking measurements are typically required to detect covert saccades. There is a rapid deceleration phase as the direction of sight lands on the new target location. Following a very short delay, large saccades are frequently accompanied by at least one smaller corrective saccade to further approach a target location. Corrective saccades can occur even if the target has been made to disappear, further supporting the projected, ballistic nature of saccadic movements. However, corrective saccades are more frequent if the target remains visible.

Accuracy, amplitude, latency and velocity can be measured with oculomotor eye movements, most commonly with saccades, vergence, smooth pursuit, and vestibuloocular movements. Saccades can be elicited voluntarily, but occur reflexively whenever the eyes are open, even when fixated on a target. They serve as a mechanism for fixation, rapid eye movement, and the fast phase of optokinetic nystagmus. The rapid eye movements that occur during an important phase of sleep are also saccades. After the onset of a target appearance for a saccade, it takes about 200 ms for eye movement to begin. During this delay, the position of the target with respect to the fovea is computed (that is, how far the eye has to move), and the difference between the initial and intended position, or "motor error" is converted into a motor command that activates the extraocular muscles to move the eyes the correct distance in the appropriate direction. The latency, amplitude, accuracy and velocity of each respective corrective saccade and latency totals and accuracy can be calculated.

Saccade accuracy refers to the eye's ability to quickly move and accurately shift from one target fixation to another. Saccade adaptation is a process for maintaining saccade accuracy based on evaluating the accuracy of past saccades and appropriately correcting the motor commands for subsequent saccades. An adaptive process is required to maintain saccade accuracy because saccades have too short a duration relative to the long delays in the visual pathways to be corrected while in flight.

Saccade amplitude—refers to the size of the eye movement response, usually measured in degrees or minutes of arc. The amplitude determines the saccade accuracy. This is sometimes denoted using "gain". It is also described as the angular distance the eye travels during the movement. For amplitudes up to 15 or 20°, the velocity of a saccade linearly depends on the amplitude (the so-called saccadic main sequence). Saccade duration depends on saccade amplitude. In saccades larger than 60 degrees, the peak velocity remains constant at the maximum velocity attainable by the eye. In addition to the kind of saccades described above, the human eye is in a constant state of vibration, oscillating back and forth at a rate of about 60 Hz.

Saccade velocity—this is the speed measurement during the eye movement. High peak velocities and the main sequence relationship can also be used to distinguish micro-/saccades from other eye movements like (ocular tremor, ocular drift and smooth pursuit).

Saccade latency—this is the time taken from the appearance of a target to the beginning of an eye movement in response to that target. Disorders of latency (timing) can be seen with saccades, VOR and visual pursuit.

Saccadic Inhibition.

Studies of eye movements in continuous tasks, such as reading, have shown that a task-irrelevant visual transient (for example a flash of a portion of the computer display) can interfere with the production of scanning saccades. There is an absence or near-absence of saccades initiated around 80-120 ms following the transient. This inhibitory effect (termed saccadic inhibition SI) is also observed in simple saccade experiments using small visual targets and it has been suggested that SI may be similar to, or underlie, the remote distractor effect.

The Remote Distractor Effect.

The remote distractor effect is a related automatic effect on saccadic latencies found when a visual onset occurs elsewhere in the visual field simultaneously with the appearance of a saccade target. Such an occurrence results in a prolongation of saccadic latency whether or not the location of the target is completely predictable. The remote distractor effect has greatest magnitude for distractors at the fovea, with the size of the latency increase decreasing in a very systematic manner at more eccentric locations. Importantly, the magnitude is dependent on the distance of the distractor from the fovea, not from the target. This relationship suggests that the effect operates through the fixation maintaining process.

Nystagmus is a description of abnormal involuntary or uncontrollable eye movement, characterized by jumping (or back and forth) movement of the eyes, which results in reduced or limited vision. It is often called "dancing eyes". Nystagmus can occur in three directions: (1) side-to-side movements (horizontal nystagmus), (2) up and down movements (vertical nystagmus), or (3) rotation of the eyes as seen when observing the front of the face (rotary or torsional nystagmus).

Visual acuity (VA) refers to acuteness or clearness of vision, which is dependent on optical and neural factors, i.e., (i) the sharpness of the retinal focus within the eye, (ii) the intactness and functioning of the retina, and (iii) the sensitivity of the interpretative faculty of the brain. A Snellen chart (eye chart that uses block letters arranged in rows of various sizes) is frequently used for visual acuity testing and measures the resolving power of the eye, particularly with its ability to distinguish letters and numbers at a given distance as well as the sharpness or clearness of vision.

The dynamic visual acuity (DVA) can be used interchangeably with kinetic visual acuity (KVA) as they both have the same meaning. In this document, DVA will be used to assess impairments in a person's ability to perceive objects accurately while actively moving the head, or the ability to track a moving object. It is an eye stabilization measurement while the head is in motion. In normal individuals, losses in visual acuity are minimized during head movements by the vestibulo-ocular system that maintains the direction of gaze on an external target by driving the eyes in the opposite direction of the head movement. When the vestibulo-ocular system is impaired, visual acuity degrades during head movements. The DVA is an impairment test that quantifies the impact of the vestibulo-ocular system pathology on a user's ability to maintain visual acuity while moving. Information provided by the DVA is complementary to and not a substitute for physiological tests of the VOR system.

The DVA quantifies the combined influences of the underlying vestibulo-ocular pathology and the person's adaptive response to pathology. DVA testing is sometimes obtained for those persons suspected of having an inner ear abnormality. Abnormalities usually correlate with oscillopsia (a visual disturbance in which objects in the visual field appear to oscillate or jump while walking or moving). With the current standing DVA testing worsening of visual acuity by at least three lines on a visual acuity chart (e.g., Snellen chart or Rosenbaum card) during head turning from side to side at 1 Hz or more is reported as being abnormal. In normal individuals, losses in visual acuity are minimized during head movements by the vestibulo-ocular system that maintains the direction of gaze on an external target by driving the eyes in the opposite direction of the head movement When the vestibular system is impaired, visual acuity degrades during head movements. Individuals with VOP deficits can improve their dynamic acuity by performing rapid "catch-up" saccadic eye movements and/or with predictive saccades.

Dynamic visual stability (DVS) and retinal image stability (RIS) can be used interchangeably. In this document, DVS will be used to describe the ability to visualize objects accurately, with foveal fixation, while actively moving the head. When the eye moves over the visual scene, the image of the world moves about on the retina, yet the world or image observed is perceive as being stable. DVS enables a person to prevent perceptual blurring when the body moves actively. The goal of oculomotor compensation is not retinal image stabilization, but rather controlled retinal image motion adjusted to be optimal for visual processing over the full range of natural motions of the body or with head movement. Although we perceive a stable visual world, the visual input to the retina is never stationary. Eye movements continually displace the retinal projection of the scene, even when we attempt to maintain steady fixation. Our visual system actively perceives the world by pointing the fovea, the area of the retina where resolution is best, towards a single part of the scene at a time. Using fixations and saccadic eye movements to sample the environment is an old strategy, in evolutionary terms, but this strategy requires an elaborate system of visual processing in order to create the rich perceptual experience. One of the most basic feats of the visual system is to correctly discern whether movement on the retina is owing to real motion in the world or rather to self-movement (displacement of our eyes, head or body in space). The retinal image is never particularly stable. This instability is owing to the frequent occurrence of tremors, drifts, microsaccades, blinks and small movements of the head. The perceptual cancellation of ocular drift appears to primarily occur through retinal mechanisms, rather than extra-retinal mechanisms. Attention also plays a role in visual stability, most probably by limiting the number of items that are fully processed and remembered.

Foveal Fixation Stability (FFS) refers to the ability to maintain an image on the fovea, which is crucial for the visual extraction of spatial detail. If the target image moves 1° from foveal center, or if random movement of the image on the fovea exceeds 2°/sec, visual acuity degrades substantially. Either of these conditions may occur if deficiencies in oculomotor control compromise the ability to maintain target alignment within these limits. Many aspects of oculomotor function do change with age. For example, smooth pursuit movements slow with age, and the range of voluntary eye movements becomes restricted, especially for upward gaze. DVA, FFS, and the vestibulo-ocular reflex decline with age.

Visual pursuit means the movement of the eyes in response to visual signals. Smooth pursuit eye movements allow the eyes to closely follow a moving object. It is one of two ways that humans and other visual animals can voluntarily shift gaze, the other being saccadic eye movements. Pursuit differs from the VOR, which only occurs during movements of the head and serves to stabilize gaze on a stationary object. Most people are unable to initiate pursuit without a moving visual signal. The pursuit of targets moving with velocities of greater than 30°/s tend to require catch-up saccades. Most humans and primates tend to be better at horizontal than vertical smooth pursuit, as defined by their ability to pursue smoothly without making catch-up saccades. Most humans are also better at downward than upward pursuit. Pursuit is modified by ongoing visual feedback. Smooth pursuit is traditionally tested by having the person follow an object moved across their full range of horizontal and vertical eye movements.

Visual pursuit accuracy is defined by the ability of the eyes to closely follow a moving object. The pursuit of targets moving with velocities of greater than 30°/s tends to require catch-up saccades. Smooth pursuit accuracy, represents how closely the percentage of time the smooth pursuit velocity value remains within the target velocity value.

Visual pursuit movements are much slower tracking movements of the eyes designed to keep the moving stimulus on the fovea. Such movements are under voluntary control in the sense that the observer can choose whether to track a moving stimulus. Although it may appear that our eyes are not moving when we fixate an object, in fact they are in continual small-scale motion, showing irregular drift and tremor, interspersed by miniature saccadic movements (less than 0.5 degrees). These fixational eye movements are essential to prevent our visual percept from fading. Pursuit consists of two phases—initiation and maintenance. Measures of initiation parameters can reveal information about the visual motion processing that is necessary for pursuit Visual pursuit acceleration—this is the rate of change of the eye velocity. The first approximately 20 milliseconds of pursuit tends to be the same regardless of target parameters. However, for the next 80 milliseconds or so, target speed and position has a large effect on acceleration.

Visual pursuit velocity—After pursuit initiation, speed of the eye movement (velocity) usually rises to a peak and then either declines slightly or oscillates around the target velocity. This peak velocity can be used to derive a value for gain (peak velocity/target velocity). It is usually near the velocity of the target. Instead of using peak velocity, it is also sometimes of interest to use measures of velocity at particular times relative to either target appearance or pursuit initiation. Eye velocity up to 100 milliseconds after target appearance can be used as a measure of prediction or anticipation. Velocity measured 100 milliseconds after pursuit begins reveals something about the ability of pursuit system in the absence of visual feedback.

Visual pursuit latency—is defined by the time from target appearance to the beginning of pursuit. The difficulty here is defining when pursuit begins. Usually it is measured from traces of eye velocity. It is often calculated by finding the intersection between two regression functions one fitted to velocity about the time of target appearance, and the second fitted over the initial part of the pursuit response.

Pupillometry tests represent conventional examination of pupillary function including inspecting the pupils for equal size (1 mm or less of difference may be normal), regular shape, reactivity to light, and direct and consensual accommodation. Traditionally, a flashlight test is one known pupillometry test that may also be desirable if neurologic damage is suspected. In a normal reaction to the flashlight test, both pupils constrict when one is exposed to light. As the light is being moved from one eye to another, both eyes begin to dilate, but constrict again when light has reached the other eye.

Frequency, in this disclosure and claims, means the number of cycles (typically rotational cycles) per second. Frequency is expressed in Hertz, which is abbreviated as Hz. VOR, DVA, DVS, RIS, and other ocular reflexes are typically measured at frequencies that include at least one frequency in the range of 0.01 Hertz (one cycle every 100 seconds) to 15 Hertz (15 cycles per second). Many prior art systems at least measure in the range of 0.1 Hertz (one cycle every 10 seconds) to 1.28 Hertz (slightly more than one cycle per second).

Gain, in this disclosure and claims, means the measured ratio of eye movement velocity to head movement velocity. More specifically, for example, the "gain" of the VOR is defined as the change in the eye angle divided by the change in the head angle during the head turn. The gain of the horizontal and vertical VOR is usually close to 1.0, but the gain of the torsional VOR (rotation around the line of sight) is generally low. Eye and head movements during the VOR are oppositely directed, and if eye velocity exactly mirrors head velocity, the gain remains at 1 during the entire head movement. This, however, is only true, if one assumes zero latency between head and eye movements. In fact, the latency of the VOR is typically about 10-20 milliseconds. A gain of 1.0 and a phase shift of 180° indicate perfect vestibulo-ocular function, meaning that the eyes move synchronously with head movement but in the opposite direction. For a healthy person, the VOR is at its best during sinusoidal head oscillations or rotations in the range of 2 Hz to 6 Hz as encountered in natural locomotion. VOR is less efficient at the extremely low frequencies (less than 2 Hz) of head movement. The gain of the translational VOR has to be adjusted for distance, because of the geometry of motion parallax. When the head translates, the angular direction of near targets changes faster than the angular direction of far targets. If the gain of the VOR is abnormal (for example when the eye muscles are weak, or if a person has taken certain drugs or had a traumatic brain injury resulting in a balance disorder), then head movement results in image motion on the retina, resulting in blurred vision. Under such conditions, motor learning adjusts the gain of the VOR to produce more accurate eye motion. This is what is referred to as VOR adaptation.

Phase (or phase shift), in this disclosure and claims, is a measurement of the relationship between eye movement velocity and head movement velocity at a particular oscillation frequency of the head. More specifically, phase shift is an offset in the timing of eye movement relative to head motion at a specific rotational oscillation frequency. The phase shift of the VOR is a second useful measure of the vestibular system and represents the timing relationship for the eye and head position. Ideally, eye position should arrive at a point in time that is equal with the oppositely directed head position. By convention, this is described as a zero phase shift. Phase is a parameter that describes the timing relationship between head movement and reflexive eye response. When the head and eyes are moving at exactly the same velocity in opposite directions, they are said to be exactly out of phase, or 180°. If the reflex eye movement leads the head movement, a phase lead is present, and if the compensatory eye movement trails the head movement, a phase lag is present.

Symmetry (and asymmetry), in this disclosure and claims, is a comparison of eye response or (reflex) in opposite directions. The words symmetry and asymmetry can be used interchangeably. Symmetry is typically expressed as a percentage. For example, the horizontal symmetry (or asymmetry) can be expressed using the following equation:

$$\text{Symmetry}=100\times((\text{Left velocity})-(\text{Right velocity}))/((\text{Left velocity})+(\text{Right Velocity}))$$

Horizontal symmetry is related to yaw of the eyes. The equation for vertical symmetry (or asymmetry) is the same as the above with the words "up" and down substituted for right and left. Vertical symmetry is related to pitch of the eyes. Symmetry can also be measured for head rotation as viewed from the front (i.e. roll) and the associated roll (or torsion) of the eyes on a clockwise versus a counter-clockwise direction when viewed from the front. Symmetry is typically evaluated at the same frequencies as gain and phase. It can be performed for one eye or both eyes. Symmetry can also be described as a comparison of the slow component of the nystagmus when rotated to the right compared with rotation to the left. Asymmetry can be present in some cases of unilateral vestibular hypo-function, as well as in other forms of vestibular dysfunction.

A Fourier transform is used to convert any arbitrary motion into a series of sinusoidal motions at various frequencies. By doing this, a graph of input motion and output motion as a function of time (i.e. in the time domain) can be converted into a graph that shows the gain and phase response plotted as a function of frequency (i.e. the response in the frequency domain). A Fourier transform can be used to convert a comparison of random natural motion (linear and/or rotational) of the head and the eyes into information that shows the gain and phase response of the eyes to movement of the head (i.e. VOR). Thus, Fourier transforms make it possible to measure VOP in a non-clinical environment without having to provide head excitations at specific frequencies.

Torsion refers to the process of being rotated about an axis. As it relates to the eye movement, it means any rotation of the vertical corneal meridians (any line bisecting the cornea through its apex). Torsional eye movements can be defined in two different ways, namely as a rotation about the line of sight and as a rotation about an antero-posterior (forward-to-backward) axis that is fixed in the head. The most natural definition of a torsional eye movement is as a rotation about the line of sight. The line of sight is the imaginary line that connects the eye with the fixation target. When the eye rotates about this line, the eyes remain fixated on this same target. When the eye makes any horizontal and/or vertical gaze shift, the line of sight and, therefore, the axis of rotation for torsion, shifts as well. For example, if one looks straight ahead, eye torsion occurs about an antero-posterior (forward-to-backward) axis. If one looks leftward, the axis of rotation for eye torsion is also rotated leftward.

If we look at a certain object, a projection of the object is made on the retina of the eyes. This projection is called the retinal image. If any torsion is made in an eye, for example in clockwise direction, then the retinal image of the object rotates by exactly the same amount, but in counterclockwise direction. Functions of eye movements in general include 1) the tracking of moving objects (visual or smooth pursuit), 2) the redirection of fixation to points of interest (saccades), 3) stabilization of the retinal images and 4) the maintenance of correspondence of the images in both eyes. Torsional eye movements are potentially important in the last two of these functions.

Degrees of freedom (DOF) refers to the freedom of movement of a rigid body in three-dimensional space. Specifically, the body could to translate in three orthogonal directions: forward/backward (surging); up/down (heaving); and left/right (swaying); and rotate about orthogonal axes: tilting forward and backward (pitching); turning left and right (yawing); and tilting side to side (rolling).

Pitch is referred to as rotation about the side-to-side axis (also called the lateral axis or transverse axis), which by example, passes through an airplane from wing tip to wing tip. Pitch changes the vertical direction the airplane's nose is pointing. A pitch motion is described as an up or down movement of the body, like that of bending forward or backward.

The longitudinal axis, using the example of a plane, passes through the plane from nose to tail. Rotation about this front-to-back is called bank or roll. Another example of a roll is the head tilting to the side toward the shoulder. A rolling motion is an up and down tilting movement of the head and shoulders.

Yaw refers to the rotation around the vertical axis. A yaw motion of the head is described as a horizontal movement from side to side. When turning the head horizontally or vertically (i.e., yaw or pitch) the VOR maintains visual fixation on the visual element throughout the head movement and thereby reduces the motion of the element visualized on the retina. The semicircular canals in the inner ear detect rotary accelerations, such as when turning the head, while the otoliths detect linear accelerations during a translation, for instance, and through the earth's gravitation. The canals and the otoliths are the anatomic substrates for VOR eye movements.

Benign Positional Paroxysmal Vertigo (BPPV) is a common cause of dizziness. On average, about 1.6% of the population has BPPV each year and about 20% of all dizziness seen in medical offices is due to BPPV. BPPV can occur in children but it is rare. BPPV is much more common in older persons, and the number of people (i.e. prevalence) in the population increases linearly with age. About 50% of all dizziness in older people is due to BPPV. BPPV is generally thought to be due to debris that has collected within a part of the inner ear. This debris can be thought of as "ear rocks", although the formal name is "otoconia". These are comprised of small crystals of calcium carbonate derived from a structure in the ear called the "utricle. The otoconia are displaced from the normal position within the utricle and come to rest in the semicircular canal resulting in "canalithiasis" or actually on the cupula resulting in "cupulolithiasis". The incidence of otoconia affecting the cupula is much less common. When the otoconia detach from the utricle they can enter any of the semicircular canals (the posterior canal (~80%), the lateral canal (~18%) or the anterior canal (<2%). An abnormality of anyone of the semicircular canals can have an adverse effect on VOP. Therefore, when testing VOP, it is advantageous to evaluate each semicircular canal. While the saccule also contains otoconia, they are not able to migrate into the semicircular canal system. The otoconia may have migrated from the utricle due to head injury, infection, surgery, another other disorder of the inner ear, or may have degenerated because of advanced age. It can also occur following the administration of ototoxic medication or can be idiopathic (e.g. the cause is unknown). The symptoms of BPPV include dizziness or vertigo, lightheadedness, imbalance, and nausea. The vertigo may last 30 seconds to 2 minutes. Some may complain of mild postural instability between attacks. Episodes of benign paroxysmal positional vertigo can disappear for some time and then re-occur. Some people also feel out of balance when standing or walking. Abnormal rhythmic eye movements (nystagmus) usually accompany the symptoms of benign paroxysmal positional vertigo. Activities that bring about the signs and symptoms of BPPV can vary, but BPPV is usually brought on by a change in the position of the head. The symptoms can often occur upon getting out of bed or rolling over in bed. In the past, BPPV testing is done by a dynamic positional test that positions the sitting person with their head turned 45 degrees to the left or right and then quickly moved into a supine position with the head tilted back and slightly lower than the shoulders. The purpose of the maneuver is to provoke the otoconia to move within the fluid of the inner ear and stimulate the canal or cupula. This is the only test that can clearly diagnose the presence of posterior canal or anterior canal BPPV (benign paroxysmal positional vertigo). Other canals must be evaluated with the head hanging and with the head lateral positions. BPPV typically exhibits a crescendo-decrescendo nystagmus observed with a delay of about 10 seconds, with a torsional component to the undermost ear and vertical upbeat component. To diagnose lateral canal BPPV, the person can lay on their back and turn the head to the left and then to the right. If the Dix-Hallpike test identifies a burst of nystagmus (typically torsional) then subsides when testing is complete, this can indicate the presence of posterior canal BPPV. If Dix-Hallpike testing is normal (e.g. no nystagmus is present), then the person can lay on their back and turn the head to the left and then to the right. If a horizontal nystagmus in the direction of the lower ear occurs (e.g. geotropic), this can be a sign for a typical lateral canal BPPV. If a horizontal nystagmus in direction of the upper ear occurs (ageotropic), this can be a sign for an atypical lateral canal BPPV. The head position for testing the left anterior and right posterior or right anterior and left posterior semicircular canals require the head to be turned 35-45 degrees and the person should be looking back at the "target" of interest or fixation. The head impulse should be performed in the plane of the canals being tested, NOT toward the nose. Superior canal BPPV is uncommon because the anatomy favors spontaneous clearing of otoconia. The eyes should always move in the plane of the stimulated canal, no matter where gaze is directed. So, for example, for left superior canal BPPV, when the body is supine and head extended, otoconia and endolymph should move away from the superior canal ampulla. This is the same as moving the head down and to the left, which excites the left superior canal. The expected compensatory eye movement is slow phase up/quick phase down in the left superior canal. The eyes will beat downward when directed to the left, and torsionally counter-clockwise (with respect to the person) when directed to the right. The down-beating is what will distinguish this from right posterior canal BPPV because posterior canal stimulation would be expected to cause up-beating nystagmus. As with all BPPV due to canalithiasis, the nystagmus may have a delay of 2-15 seconds in onset, should reach a crescendo fairly soon after that, be associated with vertigo during that time, and decay within 2 minutes. For cupulolithiasis, there may be no delay and no decay. Rehabilitation treatments in the past for BPPV have been effective, with roughly an 80% cure rate. In the past, physical head positional maneuvers are both intended to move debris or otoconia out of the portion of the inner ear where the particles are normally not located (e.g. such as the posterior canal) to the portion of the inner ear where the particles normally reside (e.g. the utricle). For example, a Semont maneuver (also called the "liberatory" maneuver) involves a procedure whereby the person is rapidly moved from lying on one side to lying on the other. It is a brisk maneuver, but can be effective in removing particles from the cupula. The Epley maneuver, also called the particle repositioning or canalith repositioning procedure, involves sequential movement of the head into four positions, staying in each position for roughly 30 seconds. The recurrence rate for BPPV after these maneuvers is about 30 percent at one year, and in some instances, a second treatment may be necessary.

Virtual reality (VR) can be defined as a computer-generated simulation of a three-dimensional image or environment that can be explored and interacted with by a user. The user becomes part of the virtual scene or immersed within the environment. While being part of the virtual environment, he or she can interact within a seemingly real or physical way, to use or manipulate objects or special electronic equipment. An example would be to perform a series of actions with a device or use a glove fitted with sensors or to wear a helmet with a projected virtual screen inside. Virtual reality environments can be implemented stereoscopically using an opaque display system, i.e. the user only sees the virtual scene and cannot see through the scene. The peripheral vision can be blocked to decrease any distraction from the user experience. Virtual reality can be used in simulators. Virtual display images or visual elements may be actively streamed from an attached computer, a wireless computer source, a smartphone, a smart display pad, or directly with digital camera systems and virtual camera systems. Virtual reality can also be created using holographic or volumetric three-dimensional displays.

Augmented reality (AR) is the superimposition of a computer-generated image on a user's view of the real world to provide a composite view. Augmented reality can be implemented using a see-through stereoscopic display or by a see-through holographic or volumetric three-dimensional display.

A concussion is a traumatic brain injury (TBI) that alters the way your brain functions. Although concussions usually are caused by a blow to the head, they can also occur when the head and upper body are violently shaken. These injuries can cause a loss of consciousness, but most concussions do not. Because of this, some people have concussions and may not realize it. Concussions are common, particularly if you play a contact sport, such as football. Every concussion has some effect on the brain to some extent. This injury needs time and rest to heal properly. Most concussive traumatic brain injuries are mild, and people usually recover fully. Post-injury symptoms may include disorientation, dizziness, nausea, imbalance, "blurred" or distorted vision, loss of coordination and concentration and/or memory. Not all post-accident symptoms are related specifically to injury of the brain. Concussions can be divided into three categories: vestibular concussions (inner ear), cerebral concussions (brain), and a combination of both (inner ear and brain).

Following a concussion, symptoms can commonly be related to inaccurate information being sensed by the damaged or weakened vestibular sensor in the inner ear (arising from the utricle, any one of the semicircular canals, saccule or vestibular nerve). This abnormality results in continuous misinformation being sent to the brain regarding the person's position in 3-dimensional space. Symptoms can also occur from numerous areas in the brain, such as the cerebellum, brain stem, corpus callosum (which connects the brain's two hemispheres), frontal lobes (helps in decision-making and memory, the mammillary bodies and hippocampus (involved with memory) and substantia nigra (involved with movement). Secondary symptoms of the post-concussion syndrome are caused by the brain attempting to adapt to the conflicting information the abnormal inner ear is providing. It is common for permanent damage to the balance system to result in long-term symptoms even after the first concussion. The reticular activating system in the brain stem is an area of the brain that acts as the "processor" for incoming information of all types and is responsible for "awareness" or the feeling of being "awake" or "clear". Abnormal input from the inner ear confuses the brain by creating a "sensory" dilemma. This dilemma results in a reduction in the processing speed of the brain in an attempt to understand the conflicting information. The limbic system is a portion of the brain responsible for sensations of "feelings". Persons with post-concussion abnormalities often describe sensations of hyper-emotionality, such as uncontrolled outbursts of crying, anxiety or anger. Abnormal eye movements, such as seen with the VOR or saccades will occur with concussions and TBI and the types of abnormal eye movements are often related to the area in the vestibular system affected with the traumatic event. When an eye response abnormality exists, impairments are evident with eye tracking and eye fixation as the head is in motion. Subsequently, human performance declines because of the inability of the eyes to maintain a focused ability on a target while in motion. After a concussion, the neuro-ophthalmologic exam commonly detects abnormalities in convergence, accommodation, the vestibulo-ocular reflex, ocular muscle balance, saccades, and visual pursuit. Visual performance measures can enhance the detection and management of concussions/traumatic brain injuries (TBI). The value of more immersive testing with this invention can more accurately enable subtle changes to be detected, can refine the ability to make appropriate return-to-play decisions, and can potentially determine susceptibility to long-term sequelae of concussions. Vestibular ocular motor screening (VOMS) has demonstrated consistency as well as sensitivity in identifying persons with concussions. The VOMS may augment current assessment tools and can serve as a single component of a comprehensive approach in the assessment of concussions after occupational or sport-related injury. Vestibulo-ocular dysfunction has been detected in a significant proportion of children and adolescents with acute sport related concussion and post-concussion syndrome. When the VOR abnormality is seen, this is a feature indicating a significant risk factor for the subsequent development of the post-concussion syndrome in pediatric acute sports-related concussion groups.

2. PHYSIOLOGY

The vestibulo-ocular reflex involves a three-neuron arc, consisting of the oculomotor nuclei, vestibular nuclei, and vestibular ganglion. The vestibular ganglion is sometimes referred to as Scarpa's ganglion, and it contains the cell bodies of the bipolar afferent neurons. The three-neuron arc is the framework to the vestibulo-ocular reflex (VOR) and the pathways that generate the reflex are extremely complex in nature. The 3-neuron arc, as the simplest VOR, consists of:

1. Primary afferent fibers from the cristae of the semicircular ducts;
2. Vestibular Nuclei, which are neurons that send their axons to the nuclei of the extraocular muscles, passing in the medial longitudinal fasciculus; and
3. Motor Neurons that send their axons to the extraocular muscles.

The abducens nuclei, otherwise known as cranial nerve VI (CN VI), innervate the lateral rectus muscle and are responsible for rotating the eyes laterally. The oculomotor nuclei, also known as cranial nerve III (CN III), are primarily responsible for controlling medial rectus (i.e. causing eyes to pull in). The actions involved in a leftward head rotation can be described as follows:

1. The head rotates left; and
2. The eyes turn to the right (at pretty much at the same speed). In order to turn to the right, the right lateral rectus and the left medial rectus muscle must contract. This requires the motor nuclei and abducens nucleus to send a signal to move the right eye to rotate outward. It also requires that the motor nuclei and oculomotor must elicit a signal to cause the left eye to rotate inward.

The VOR generates compensatory eye movements in response to head motion detected by the vestibular sense organs located in the inner ear. The oculomotor response to angular head movement is called the angular VOR (AVOR or VOR) and has been demonstrated for rotation in yaw, pitch, and roll. An oculomotor response to linear acceleration has been described for acceleration along the interaural axis, spinal axis, and nasal-occipital axis and has been called the linear VOR (LVOR). The VOR is crucial to the maintenance of gaze stability and visual acuity. Individuals who have lost their vestibular systems suffer from illusory motion of the seen world (oscillopsia) during head motion and may have difficulty recognizing familiar faces while walking. Dysfunction within the VOR pathways may result in nystagmus, ocular misalignment, ocular torsion, and pathologic head tilt. All of these findings can adversely affect human performance to focus on a target of interest with rotational or translational movement or motion.

The visual, vestibular and proprioceptive systems are key sensory organ systems for maintaining balance. The corrective eye movement response is used to provide stable vision during the head movements of walking, running, driving and all of the other normal movement activities. The visual system receives sensory input from the eyes to determine body position in space and with movement. The vestibular system receives sensory input from the inner ears. The inner ear is sensitive to gravity and detects both linear and angular movements. The proprioceptive system provides information about the relative position of body segments to one another and about the position of the body in space. When these three systems are functioning properly, balance problems do not normally exist. In addition, these three systems are mutually interdependent and provide redundancy, which permits balance to be maintained if one of these three primary systems fails. Three resultant mechanisms created by the visual, proprioceptive, and vestibular systems include the oculomotor system, VOR, and the vestibular spinal reflex. The simple eye movement response (e.g. VOR) is an indicator of the function of one part of the balance system.

The oculomotor system keeps images centered on the fovea, which is the area of high visual acuity. DVA is the ability of an individual to quickly fixate and re-fixate on different and moving targets or visual elements. The three components of this oculomotor system controlled by the central nervous system include: saccades, smooth pursuit, and optokinetics. The saccadic system is responsible for rapidly directing the fovea to a target of interest in visual space. This system creates a conjugate movement of the eyes, a saccade that brings the fovea on target within a fraction of a second. Saccades are demonstrated and measured by having an individual keep his or her head still while moving only his or her eyes from target to target (typically, the target will appear middle, then left, middle, then right, etc.). The smooth pursuit system is concerned with keeping the fovea on a moving target once that target has been located. Smooth pursuit is tested by having a person keep his or her head still while smoothly following a moving target with his or her eyes. The optokinetic system detects motion using peripheral vision. The optokinetic system is tested by having a person keep his or her head still while trying to focus on targets that move rapidly across the person's field of vision, disappearing on one side and reappearing on the other.

As noted previously, the VOR is a reflex eye movement designed to stabilize images on the retina, specifically the fovea, during head movement by producing eye movement in the direction equal and opposite to head movement. If the position of the head is altered, this reflex system keeps the eye looking in the same direction as it did before the movement. The head movement of interest typically ranges from 0.1 Hz (nearly still) up to 15 Hz. The VOR elicits eye movements in response to head movements in all directions, including horizontal, vertical, and rotational head movements. When head motions are above 2 Hz (two back and forth motions in one second), the VOR is essential to helping maintain balance, because when head motions reach that speed, the smooth pursuit system, the saccadic system, and the optokinetic system cannot effectively function at that speed, and the VOR takes over. The VOR has often been measured in the dark by some to distinguish eye movements driven by vestibular stimuli from eye movements driven by visual stimuli. The performance of the VOR can be measured by the gain, which is defined as the amplitude ratio between eye and head velocities. If a person's VOR gain is poorly calibrated, then head movements result in image motion on the retina, causing blurred vision. Under such conditions, motor learning adjusts the gain of the VOR to produce more accurate eye motion. Such adjustments are needed throughout life, as neurons and muscles develop, weaken, and die or when a new pair of eyeglasses changes the magnification of the visual field. Depending on the relative direction of head motion and image motion, the gain of the VOR can be adaptively increased or decreased. An increase in VOR gain is induced by image motion in the direction opposite that of the head (gain up stimulus) and a decrease in VOR gain is induced by image motion in the same direction as the head (gain down stimulus).

The VOR needs to be fast: for clear vision, head movement must be compensated almost immediately; otherwise, vision corresponds to a photograph taken with a shaky hand. To achieve clear vision, signals from the semicircular canals are sent as directly as possible to the eye muscles. The connection between the semicircular canals and the eye muscles is made using only three neurons, and is called the three-neuron arc. Using these direct connections, eye movements lag the head movements by less than 10 ms, and thus the VOR. The VOR acts at short latency to generate eye movements that compensate for head rotations to preserve clear vision during locomotion. The VOR is the most accessible gauge of vestibular function. Evaluating the VOP requires application of a vestibular stimulus and measurement of the resulting eye movements.

More specifically, the VOR serves to compensate eye movements effectively for head movements at frequencies in the range of 0.1-15 Hz, especially if the head movement is voluntary. However, the VOR is less accurate at lower frequencies, especially those lower than 0.1 Hz, where the gain drops significantly and a phase lead appears. The optokinetic reflex has the opposite performance characteristics. It has longer latency (due to the fact that it uses visual input and not inner ear stimulation) than the VOR, but at low frequencies (i.e. less than 0.1 Hz), it has near unity gain and no phase difference. From 0.1 Hz to approximately 1 Hz, the optokinetic reflex begins to lose gain and develop a phase lag due to higher latencies. At higher frequencies it cannot effectively compensate due to its relatively long latency and low gain compared to the VOR. Therefore, the combination of the two mechanisms allow for maximal image stabilization all the way from the lowest frequencies (governed mostly by the optokinetic reflex) to the highest frequencies (governed mostly by the VOR). There is another aspect of the VOR/optokinetic reflex combination that contributes to improved performance over either system alone. This aspect is a timing issue: time of onset and time of offset. As previously mentioned the VOR has a very short latency (onset time) while the optokinetic reflex has a longer latency. The VOR then allows for a faster reaction time even at lower frequencies. But the VOR will eventually decay during constant, zero-acceleration rotation due to the elasticity of the cupula within the semicircular canal. Although effectively extended through central processes, the time constant of pure VOR related nystagmus in humans is approximately 25 seconds. The optokinetic reflex, however, has a long latency but no time constant, as its response does not decay with repeated stimulation of the retina by an optical flow. Therefore, as VOP decays, the optokinetic reflex is building up, creating a continual, seamless stabilization of images on the retina.

The vestibular spinal reflex adjusts posture for rapid changes in position. It helps the maintenance of balance with rapid head movement. At least two of the three balance-related sensory organ systems (vestibular, visual, and proprioceptive) are necessary to maintain balance, albeit with some difficulty if one of the three is dysfunctional. However, even though the interdependence of the systems may lead to balance compensation when there is a loss of at least one system, other brain functions may suffer as a result. In particular, cognitive difficulties can be caused by disturbances in the balance mechanisms. These difficulties are felt to be a result of suppression of the reticular activating system in the brainstem. Since the areas of the brain that usually carry out thought and memory functions now must focus on balance, the brain sacrifices some of its cognitive function. This leads to a change in mental abilities of the individual. When an individual appears to be suffering from a balance disorder, the individual can be tested to determine which of the three systems exhibits abnormalities. Numerous tests have been developed to assess the function of these three systems.

To understand more in detail, the VOR starts in the vestibular system, where semicircular canals get activated by head rotation. During rotational movements of the head, the endolymphatic fluid within the semicircular canals shifts because of its inertia. This deflects the cupula. Endolymphatic flow toward the ampulla is excitatory in the horizontal canals, while flow away from the ampulla is excitatory in the superior and posterior canals. A signal of rotation or translation impulses are sent to the vestibular nerve (cranial nerve VIII) through Scarpa's ganglion and end in the vestibular nuclei in the brainstem. The afferent nerves from the ampulla actually carry both excitatory and inhibitory signals to the 4 major vestibular nuclei: medial vestibular nucleus, lateral vestibular nucleus, inferior or descending vestibular nucleus, and superior vestibular nucleus. Different regions within each of the nuclei project to the oculomotor nuclei (cranial nerves III, IV, and VI), which control the muscle movements of the eyes.

Efferent signals from these nuclei then result in contraction and relaxation of the appropriate ocular muscles. Excitation of the superior canal results in contraction of the ipsilateral superior rectus and contralateral inferior oblique muscles and relaxation of the ipsilateral inferior rectus and contralateral superior oblique muscles, which results in an upward torsional eye movement. Excitation of the posterior canal results in contraction of the ipsilateral superior oblique and contralateral inferior rectus muscles and relaxation of the ipsilateral inferior oblique and contralateral superior rectus muscles. This results in a downward torsional eye movement. Finally, excitation of the lateral canal results in contraction of the ipsilateral medial rectus and contralateral lateral rectus muscles and relaxation of the contralateral medial rectus and ipsilateral lateral rectus muscles. This results in a horizontal eye movement toward the opposite ear.

In addition to these direct pathways, which drive the velocity of eye rotation, there is an indirect pathway that builds up the position signal needed to prevent the eye from rolling back to center when the head stops moving. This pathway is particularly important when the head is moving slowly, because in this situation position signals dominate over velocity signals. The eye muscles require this dual velocity-position drive. The integrator for horizontal eye position is in the nucleus prepositus hypoglossi in the medulla, and the neural integrator for vertical and torsional eye positions is in the interstitial nucleus of Cajal in the midbrain. The same neural integrators also generate eye position for other conjugate eye movements such as saccades and smooth pursuit. The vestibulo-cerebellum compares input from visual and vestibular sensors and mediates changes in the VOR after vestibular injury or change in visual function.

In addition to oculomotor projections, the vestibular nuclei send fibers to the vestibulo-cerebellum, the nucleus prepositus hypoglossi, and the cells within the paramedian tracts. The nucleus prepositus hypoglossi is crucial for the maintenance of a steady gaze, while the cells within the paramedian tracts are responsible for relaying information to the vestibulo-cerebellum, specifically the flocculus. Reciprocal projections to and from the cerebellum assist in fine motor control of eye movements. The latency of action of the rotational VOR is 7-15 milliseconds, which is the time required for the eyes to respond in an equal, but opposite, manner to the motion of the head. This time is remarkably fast compared with the latency for visually mediated eye movements, which is longer than 75 milliseconds. Cerebral function may also be responsible for the modification of the VOR and the ability to suppress the VOR. Specifically, injuries to the parietal vestibular cortex and the ocular gyms appear to interfere with visual suppression of the VOR. In particular, the right temporoparietal cortex is believed to be involved in the modulation of the VOR. This region has been shown to be sensitive to the effects of sleep deprivation, particularly with respect to VOR gain during step testing.

The translational VOR pathways are activated in response to stimulation of the otolithic organs. The utricle responds to lateral translation stimuli, whereas the saccule responds to vertical translations. Translational VOR pathways also appear to be mediated by projections to the ocular motor nuclei via projections from the vestibular nuclei. Specifically, excitation of the utricular macula results in contraction of the ipsilateral superior oblique, superior rectus, and medial rectus muscles and relaxation of the contralateral inferior oblique, inferior rectus, and lateral rectus muscles.

Having described the normal vestibulo-ocular system, it is important to discuss vestibulo-ocular dysfunction. Similar to all other systems in the body, most individuals are not aware of the presence of the vestibulo-ocular system until it malfunctions. Acute vestibulo-ocular dysfunction may manifest in several different ways, depending on the anatomical location of the lesion or lesions, and may result from labyrinthine disorders or disorders of the central vestibular system. Studies have shown that people with a unilateral peripheral vestibular lesion may exhibit asymmetric responses to rotation. On the other hand, people with a compensated unilateral lesion show a characteristic pattern of decreased gain and increased phase lead at low-frequency stimulation. Bilateral peripheral vestibular lesions are characterized by low gain and phase lag as determined by sinusoidal testing. These persons commonly report oscillopsia, a sensation of vertical or horizontal motion of the environment, or persistent unsteadiness, especially in the dark. Rotational chair testing is ideal in the assessment of these persons because, unlike caloric testing, higher frequencies are tested and both labyrinths are simultaneously stimulated. This allows for an accurate determination of remaining vestibular function, which is important for determining a course of treatment.

Central vestibular deficits may also affect VOP. Gains may be increased in some individuals with cerebellar deficits. Cerebellar atrophy, on the other hand, may result in a disorganized nystagmus pattern with beat-to-beat variabilities in amplitude. Lesions within the parietal vestibular cortex and the ocular gyms may interfere with the ability to suppress VOP visually. High-velocity angular vestibulo-ocular function can also be affected by post-blast exposure, as studied in military service members.

Although an impaired VOP is generally the result of an injury to the vestibular system, VOP may also be affected by systemic disease processes such as migraines, depression, and anxiety disorders. With migraine vestibulopathy, one may see an elevated gain with visually enhanced VOR, a testing paradigm where the VOR rotation stimulus is done in a lighted (i.e., visually enhanced) environment rather than in the traditional dark booth. Persons who experience anxiety disorders may have an increased vestibular sensitivity resulting in significantly higher VOR gains and shorter time constants. Finally, those persons with major depression have been shown to have hypoactive vestibular nuclei, resulting in a decrease in the slow phase of the nystagmus.

Other common issues can also adversely affect VOP. Vestibulo-ocular performance may be affected by systemic disease processes such as migraines, depression, and anxiety disorders. Poor alertness, inadequate sleep, poor visual acuity, and performing in low light levels can adversely affect these responses. Drugs can also have a profound adverse effect on VOR, DVA and poor foveal fixation stability. Ethanol consumption can disrupt the VOR, reducing DVA and retinal visual stability or foveal fixation of visual elements of importance. Classes of sedatives (example Barbiturates), stimulants (example Adderall), recreational drugs (Cocaine), anti-histamines (Benadryl), labyrinthine suppressants (example Scopolamine), pain medications (example Oxycontin), phenothiazines, (example Phenergan), muscle relaxants (example Valium), ototoxic medication (example cisplatin, gentamicin, streptomycin) can all cause abnormal oculomotor responses. Surgery or tumors affecting the vestibular system can also adversely affect these responses.

Other external factors affecting a person can contribute to an abnormal VOR, poor DVA and foveal fixation stability. For example, provocative motion environments in aviation can be prone to cause destabilization of the retinal image, when flight pattern, vibration, angular motion, translation and lack of vision can be of sufficient severity to prevent a pilot from reading the instruments. The ability of a pilot to perceive important visual cues, either from the external world or from flight deck instruments, can be degraded by factors that impair either the quality of the retinal image or the transduction process of the image by the sensory cells of the retina.

There can be technical reasons, such as goggle slippage with testing, that causes eye-to-head movement velocity asynchrony in both head movement directions rather than systematic eye velocity saturation in just one direction, and can adversely affect the measurement of VOP.

When the VOR or DVA are abnormal, which occurs during the early stage after unilateral vestibular loss, recovery is delayed if the visuomotor experience is prevented. Avoidance of movements and body positions that provoke vertigo also retards recovery. Factors affecting recovery of the VOR and/or DVA when it is reduced include medications, visual and somatosensory inputs, stage at which treatment is commenced, daily exercise duration, symptom intensity, the site of the lesion, the person's age, and psychogenic factors. The use of centrally acting medications such as vestibular suppressants, antidepressants, tranquilizers, and anticonvulsants also prolong the mean duration of therapy required to achieve the eventual outcome.

There can be factors that enhance the VOR and RIS or DVA. Increased mental activity, ortho-optho (eye movement) exercises, head/eye exercises, lack of drugs/alcohol, rest and better lighting in the area of performance all will enhance the VOR and/or DVA. With any of these factors better RIS and retinal visual stability can be achieved.

3. CLINICAL TESTING

Historically, VOR, DVA, and DVS measurement have been performed in a controlled environment, typically a clinical setting. Techniques used to measure VOR in clinical settings include (1) stimulating the inner ear with caloric irrigation using air or water and (2) rotational testing, of which there are four types in the prior art: (2a) rotational testing by fixing the head to a rotationally moving chair, (2b) actively moving the head only, using an external signal such as a metronome with video recording (2c) passively moving the head only, with the assistance of another person using video recording and (2d) active head shake testing, using Frenzel glasses, with an observer looking at eye movements. Traditional vestibulo-ocular performance testing (including DVA, etc) has been limited to horizontal and vertical tracking due to equipment limits.

Caloric irrigation produces a convection current of endolymph when the canal is oriented vertically because endolymph sinks when cooled and rises when warmed. Thus, cool irrigation causes nystagmus (which is seen with video recording as rapid eye twitching) away from the ear and warm irrigation causes nystagmus toward the ear. Caloric irrigation is inherently limited by the effectiveness of heat transfer between the external and inner ear. A small or occluded external ear canal reduces the intensity of the caloric stimulus to the inner ear. Consequently, a reduced response may result from technical issues such as inadequate irrigation rather than vestibular hypo-function.

Rotational testing can be performed using active (volitional) or passive rotations with video recording. Rotational testing can be low frequency or high frequency. Rotational testing can use head only or whole body rotations (which occurs in a rotary chair). There are two main advantages of rotational testing over caloric testing. First, rotational testing does not depend on the effectiveness of thermal energy transfer across the middle ear and through the temporal bone. Second, rotational testing allows precise application of multiple frequencies of rotational stimuli, whereas caloric testing is equivalent to a single, very low frequency (0.003 Hz) vestibular stimulus. There are two main disadvantages of rotational testing. One disadvantage is that rotation affects both ears simultaneously, making it less helpful in detecting unilateral lesions. Another disadvantage is the cost of the equipment.

The stimuli during rotational testing are usually either impulses or sinusoidal rotations. Impulse rotations demand a rapid acceleration (usually about 100°/second/second) to a constant speed and, after the nystagmus fades away, a sudden stop during which the nystagmus is again recorded. Sinusoidal rotations are performed by rotating the person's head or body from side to side, so that head movement recordings appear as a series of sine waves. The frequency of these sinusoidal rotations is measured in cycles/second, also known as Hertz (Hz). VOR rotary testing is done in darkness or with the eyes closed to avoid the influences of vision on the VOR. The VOR can also be suppressed by fatigue or inattentiveness. Consequently, mental alerting tasks (e.g., mental arithmetic) are used to maximize VOR responses. The purpose of rotational testing is to determine whether dizziness may be due to a disorder of inner ear or brain. There are three parts to the test. The chair test measures symptoms of dizziness (jumping or back and forth movement of the eyes, called nystagmus) while being turned slowly in a motorized chair with the head fixed. Persons with inner ear disease become less dizzy than do normal persons. The fixation test measures nystagmus while the person is being rotated, while they are looking at a dot of light that is rotating with them.

Rotary chair testing provides a known stimulus input and measuring the response output. The ratio of the output to input is called the "transfer function". There are many reasonable protocols for the input. For a linear system, any protocol that includes a reasonable selection of frequency components should result in the same result, which is a gain and time constant. As there are nonlinear processes in the vestibular system (such as prediction), the various methods may not always produce the same results. At present, most laboratories use either sinusoidal testing or step testing.

The sinusoidal test protocol involves rotating the chair so that it moves sinusoidally. Because the derivative of a sine is another sinusoid, chair position, velocity and acceleration all change sinusoidally. Ordinarily one chooses a desired peak chair velocity, such as 60 deg/sec, and one also picks a series of frequencies to test covering about 0.1 to 1 Hz. These frequencies cover the range of responses where gain and phase show their greatest variability when there is disease. A variant of sinusoidal testing is "sum of sines" (SOS) where one mixes together a group of sine waves to make the input less predictable. Although the SOS appears complex, it can be analyzed using standard mathematical methods (i.e. Fourier analysis). A "Bode plot" is essentially a semi-logarithmic plot of vestibular gain and phase and is generally used to present results. A powerful motor is needed to attain the higher frequencies, and for this reason, sometimes testing will only include lower frequencies or the peak velocity will be reduced at the highest frequency.

The step test involves suddenly changing chair velocity (with an impulse of velocity). Step responses provide roughly equivalent gain/phase information, as does sinusoidal testing. Step responses have many problems. They require a powerful chair to provide a high acceleration transient. They may be less reliable as well as somewhat more stressful to the person, and for this reason, sinusoidal testing is generally preferred. Motion sickness is sometimes associated with prolonged vestibular responses, and for this purpose, step responses may be preferable to sinusoids. Practically though, nausea is unusual in sinusoidal testing and this is not a strong consideration.

There are several other alternative procedures involving rotation of the head to evaluate VOP. Active head movement allows the user to self-move the head back and forth with an external stimulus such as the sound of a metronome (autorotation). With each click of the metronome, the person moves the head. The frequency of the clicking and therefore the head movements will gradually increase. Both of these tests provide high-frequency information compared to being seated in a rotary chair (which provides low frequency data) and measure something a little different, which is the contribution of the inner ear, cognitive input, and neck inputs to nystagmus rather than the contribution of the inner ear alone. The Vestibular Autorotation Test is a computerized test that measures the horizontal (sideways rotation or yaw) and vertical (up/down rotation of the face, also known as pitch) VOR with the use of active head movements in the range of 0.1 Hz to 15 Hz to obtain gain and phase.

The VOR, when tested by passive rapid movement of the head using an assistant, is referred to as the Rapid head impulse test or Halmagyi-Curthoys-test. As the rapid head impulse test is performed, the head is rapidly moved to the side with force, and the VOR will be controlled if the eyes succeed to remain looking in the same direction. When the function of the balance system is reduced, for example in the right ear by a disease or by an accident, quick head movement to the right cannot be sensed properly. As a consequence, no compensatory eye movement is generated, and the person cannot fixate a point in space during this rapid head movement.

Active Head Shake Test: Rapid horizontal head shaking by oneself for 15 to 20 seconds occasionally results in horizontal post-headshake nystagmus usually (but not always) directed away from the side of a unilateral vestibular loss. When done in the office setting Frenzel's glasses are typically worn while doing this test to prevent ocular fixation that can suppress the nystagmus. Headshake nystagmus is generally thought to occur when asymmetries in resting vestibular tone are exaggerated via brainstem control mechanisms.

Optokinetic nystagmus (OKN) can be tested by moving a strip with parallel stripes in front of the person's eyes and asking the person to watch the stripes go by. It can also be tested by asking the person to watch any other similar moving image. This type of image normally induces rhythmic eye movements (called nystagmus) that consist of an alternating slow phase with slow pursuit movements in the direction of strip movement, and a rapid phase with quick re-fixations back to midline.

4. LIMITATIONS OF THE PRIOR ART FOR A NON-CLINICAL ENVIRONMENT

To measure the VOR under natural conditions, both head and eye movements must be measured accurately during active natural head motion in an ambulatory setting. Prior art systems for tracking head and eye movements have serious limitations due to the complexity of the equipment being used. Prior art systems for tracking eye movement include electro-oculography, magnetic scleral search coils, infrared video-nystagmography, and other video eye-tracking devices. Prior art head motion can come from a rotary chair that is excited at a specific set of frequencies and amplitudes. It is also known to measure head motion using a magnetic position transducer. These prior art techniques do not allow for a simple and low cost system for measuring or enhancing VOP.

Electro-oculography (EOG) is a commonly method for recording eye movements. This technique measures the change in corneo-retinal potential using electrodes placed around the inner and outer canthi of the eyes. It is limited by poor sensitivity, poor vertical and binocular measurements, artifacts introduced by muscle action potential, and electrical noise introduced by electrode movement and other physiological and environmental sources. To test the VOR reliably, it is important to determine that other types of eye movements are normal for two reasons. First, proper interpretation of the VOR responses depends on intact eye movements. Second, abnormalities of eye movements can themselves be useful in localizing neurologic abnormalities. EOG permits recordings of the direction, amplitude, and velocity of eye movements. Torsional eye movements are not recorded with EOG.

Magnetic search coil are a reliable eye movement recording technique, but it requires the person to wear a specialized contact lens during testing and is available for clinical use only in a few institutions. Magnetic scleral search coils are circles of electrically conductive wire that are embedded into tightly fitting contact lenses or a rubber ring that adheres to the white portion (sclera) of the eye. They can also be surgically implanted in the sclera (white portion) of the eye. Alternating magnetic fields are then generated by electromagnets (field coils) positioned around the eye. Through magnetic induction, electric currents are generated in the search coils. The polarity and amplitude of the current generated varies with the direction and angular displacement of the eye. By measuring these values, the position of the eye can be determined. Magnetic scleral search coils can be applied to one or both eyes. In order to detect eye orientation in more than one dimension (e.g. up/down versus left/right), multiple electromagnets must be oriented orthogonally to one another. Each electromagnet must generate a field using a different frequency in order to allow a computer to determine the displacement in multiple dimensions. A second search coil could be added to measure torsional rotation of the eye. Magnetic scleral search coils cannot be used to measure free head motion due to the requirement that the search coils (and therefore the eyes) must remain close to the center of the magnetic field generated by the field coils. Use of this technique is also limited by the inability to make measurements of linear motion of the head. Furthermore, search coils have an invasive nature.

Infrared video nystagmography is an alternative method of determining eye movements that utilizes infrared cameras positioned to detect movement of the eyes in darkness. Horizontal eye movements are the most important and easiest to record because vertical eye movements are prone to blinking and eyelid movement artifacts. However, vertical eye movements should be identified and measured to help determine vertical nystagmus and blinking that may affect horizontal channel recordings. Torsional eye movements can be seen on infrared video recordings.

Other video eye-tracking devices can provide comparable results to the scleral search coil method for measuring eye movements. The main disadvantage of video recordings compared with coils was their limited sampling frequency. This is important for investigating fast eye movements, such as saccades or responses to impulsive vestibular stimulation, where accurate latency and gain measurements over a short time span are required. Another disadvantage of infra-red (IR) video systems is the difficulty in tracking eye positions in the dark because of large pupils and increased occlusion of the pupils by eyelids. If eyelashes or droopy eyelids partly occlude the pupil, proper detection of eye position may be deteriorated. Dark eyelashes may also be problematic, because they can be confused with the pupil. With IR video systems, subjects generally cannot wear glasses due to obstruction by the head device. On the other hand, soft contact lenses do not seem to influence performance. In contrast, with scleral search coils only hard lenses can be used.

Studies of eye movements are often performed with the subject's head secured to the headrest of a chair in which is rotated (e.g. rotary chair testing). For example, the "gold standard" for testing the VOR has utilized low-frequency rotation (e.g., 0.1 Hz) of a subject in a horizontal plane. During natural movements such as locomotion, however, the head is subjected to rapid, unpredictable transient head perturbations with frequency components of up to 15 Hz. The long latency and poor high-frequency response of visual or cervical reflexes make them poorly suited for responding to these perturbations. A primary physiological role of VOR is to compensate for the high-frequency perturbations encountered during locomotion.

It is known to use a head tracker that uses a magnetic position transducer (see Allison et al, IEEE Transactions on Biomedical Engineering, November 1996). However, the transducer described by Allison requires the use of an external pulsed magnetic transmitter at a fixed location and therefore the system is not a self-contained portable system that can be used in any environment.

To summarize, current clinical vestibular eye response measuring equipment is highly specialized, bulky and requires a dedicated laboratory. There is need to have a simpler system and method of measuring vestibulo-ocular performance. The use of virtual reality or augmented reality environments can greatly simplify the measurement of VOP with the potential for helping a person improve his/her VOP.

BRIEF DESCRIPTION OF THE DRAWINGS

For a more complete understanding of the present invention and the advantages thereof, reference is made to the following description taken in conjunction with the accompanying drawings in which like reference numerals indicate like features and wherein:

FIG. 11A shows an unaltered visual element;

FIG. 11B shows the visual element of FIG. 11A that has been altered by defocusing the visual element and superimposing a target;

FIG. 12 shows a scene that can be used for optokinetic testing in a virtual or augmented environment;

Figure 1:
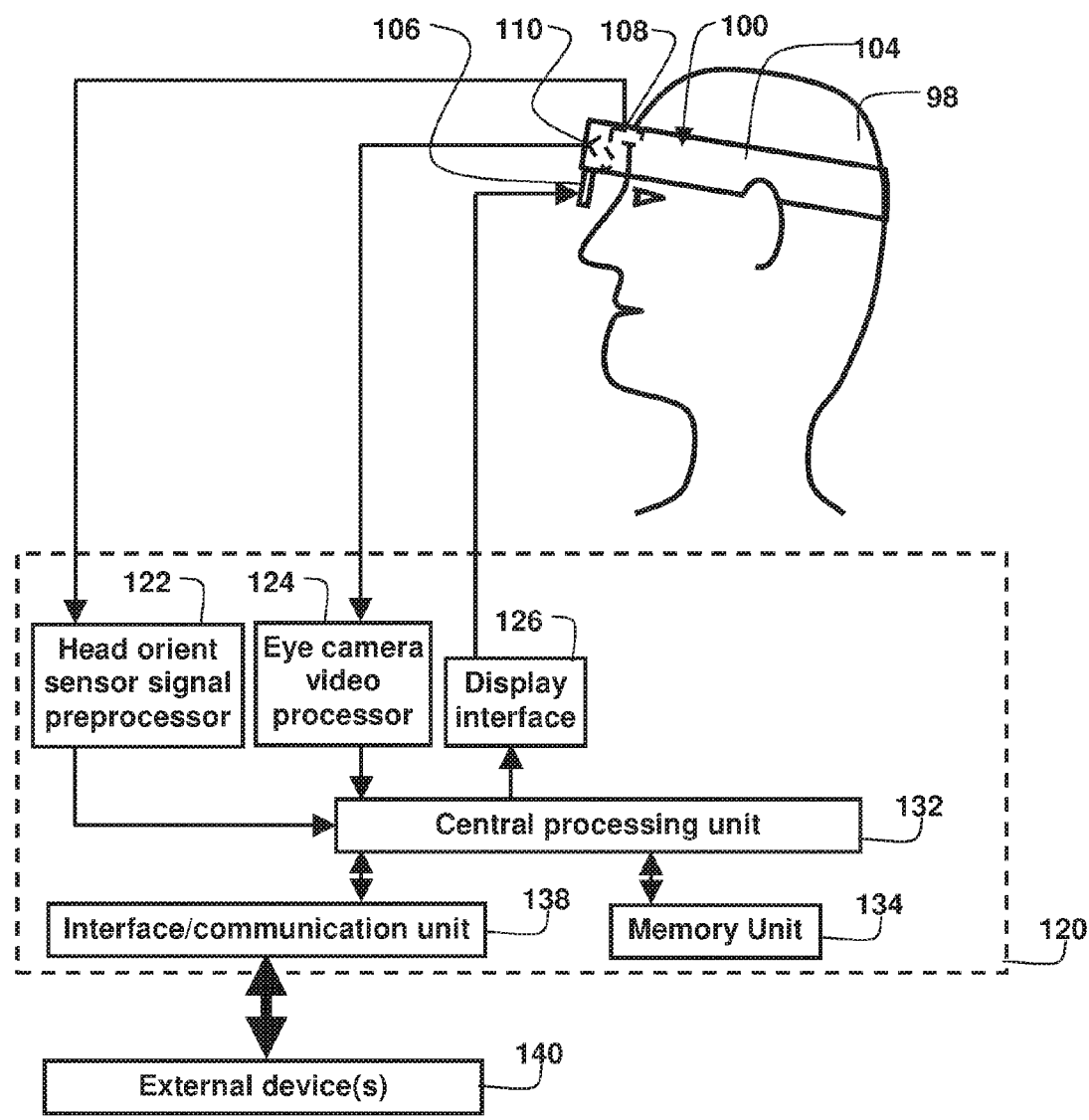
FIG. 1 shows a person wearing a head-worn augmented reality system for measuring and/or improving vestibular performance, ocular performance, and/or vestibulo-ocular performance.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment.

It should be understood that various changes could be made in the function and arrangement of elements without departing from the spirit and scope as set forth in the appended claims. Preferred embodiments of the present invention are illustrated in the Figures, like numerals being used to refer to like and corresponding parts of the various drawings. Specific details are given in the following description to provide a thorough understanding of the embodiments. However, it will be understood by one of ordinary skill in the art that the embodiments may be practiced without these specific details.

1. Overview of System and Method

In one embodiment, the present invention comprises a head-worn device for measuring and/or improving a person's VOP (vestibulo-ocular performance) by:
(a) presenting visual virtual reality (VR) or augmented reality (AR) information;
(b) tracking head movement; and
(c) tracking eye movement as the visual VR or AR information is presented.

VR or AR devices incorporating eye tracking can provide more realistic and immersive methods for identifying and measuring eye movement or oculomotor responses to changes in head orientation. VOR measurements using VR or AR can be used to predict human performance, to determine candidacy for specific jobs or tasks, or for neurologic health status assessment (such as alcohol and drug usage, the need for rehabilitation, or for the detection, assessment, or management of concussions). VR and/or AR platforms can be an engaging method for vestibular assessment and treatment. All six semi-circular canals can be evaluated for normal function, hypofunction, hyperfunction, for the presence of abnormalities such as BPPV, and to help determine if a person has a peripheral vestibular disorder or central disorder. By using an AR/VR device with a data interface, all of the information obtained by using the device can be directly shared to other devices or uploaded to remote locations. With these immersive systems of assessment, accuracy of measurement and methods of treatment can easily be provided by visualizing the correct head position and providing the person using these devices an enhanced fixation ability to reposition the otoconia back into the utricle and out of the affected semicircular canal or cupula.

In embodiments of the present invention, VOP testing could be done in an AR or VR environment. The use of an AR/VR environment provides an opportunity to create VOP tests with a variety of advantages. For example, in an AR/VR environment, tracking can easily be done not only in a purely horizontal or vertical direction, but also using any pattern combining horizontal (i.e. x-direction), vertical (i.e. y-direction), or depth (i.e. z-direction) movement, including but not limited to sinusoidal, pendular, and diagonal scan paths in a three-dimensional space. When testing, the eye tracking sensor or sensors can automatically establish an electronic 'lock-on' to the person's eye. Different speeds of for testing can be available, such as 2 Hz, 4 Hz or 6 Hz. Accuracy of the shift of the eyes from target fixation to another can be measured. Analysis for gain and phase of tracking can also be measured. Peak velocity, amplitude, latency, duration, and inhibition of saccades can additionally be measured. The remote distractor effect can be detected. The slow component velocity (SCV) with optokinetic and gaze testing can also be measured using either an AR or a VR environment. Smooth pursuit accuracy movements, velocity, acceleration and latency can also be measured. Measurement of oculomotor movement can be performed either with traditional methods or by using variety of pattern, directions and frequency of the image presentation in the AR or VR environment. Oculomotor assessment and measurement in these systems can provide potential higher level of evaluation that what was available in the prior art and this can be performed with static or dynamic methods, both for the object being viewed, as well as for the person using the VR or AR platform and engaged in the testing. Additionally, realistic images can be used to simulate the target of interest or visual element being viewed or the environment in which the person would normal be engaged in when performing his or her activities of choice or occupation. For example, VOR testing can be performed in either platform where is object is static and the person moves the head in a horizontal or vertical manner, or the object can be dynamically changing in size, position, or other features, while the person is rotating the head. Natural or realistic images can be used in the visualized scene, as well as with the target of interest being viewed and measurement of the eye's ability to focus on the target can easily be measured. One can determine a fixation or distraction factor. A person who has a high amount of distraction would most likely not be able to perform as well as another person who had a high fixation factor, in the presence of high distraction scene content.

2. Detailed Description of the Figures

Referring now to the figures, FIG. 1 illustrates a person 98 wearing a head-worn augmented reality system for measuring and/or improving vestibular performance, ocular performance, and/or vestibulo-ocular performance. Referring in more detail to FIG. 1, the person is wearing a headband head worn unit 100, which comprises a headband 104, a see-through display 106, a head orientation sensor 108, and an eye sensor 110. The headband 104 is a head attachment element that is designed to fit snugly on the head of the person 98 so that all changes in head orientation result in equal changes in orientation of the head-worn unit 100. The head orientation sensor 108 is rigidly attached to the headband 104. In at least one embodiment, the head orientation sensor 108 senses (is responsive to) pitch, roll, and/or yaw. Pitch can be described as upward or downward movement of the face. Roll can be described as rotation of the face when viewed from the front. Yaw can be described as leftward and rightward movement of the face when viewed from the front. The head orientation sensor 108 can be constructed from one or more elements or it can be monolithic. The head orientation sensor 108 can use one or more accelerometers, gyroscopes, magnetometers, or any other relative or absolute position, velocity, or acceleration sensing device capable of being understood by anyone skilled in the art. In one embodiment, the orientation sensor comprises a micro-electro-mechanical system (MEMS) integrated circuit.

Further referring to FIG. 1, in one embodiment, the eye sensor 110 is more specifically an eye tracking digital video camera that is pointed at the eyes of the person 98. The eye sensor can be responsive to vertical movement of the eyes (which represents pitch), rotation of the eyes (which represents roll), and horizontal movement of eyes (which represents yaw). There can be only one eye sensor camera 110, that monitors only one eye, one eye sensor camera 110 with a wide angle, that can monitor both eyes, or two separate cameras, one to monitor each eye. There can also be multiple cameras, to monitor different areas of each eye (e.g. eye response sensors tracking pupil features and corneal reflection surface(s). The eye sensor video camera 110 can be positioned anywhere around the eye, and can utilize visible or invisible light.

In the embodiment shown in FIG. 1, the see-through display 106, head orientation sensor 108, and camera 110 are connected to an electronic module 120. The electronic module comprises a head orientation sensor signal preprocessor 122 that is connected to the head orientation sensor 108, an eye camera video processor 124 that is connected to the camera 110, and a display interface 126 that is connected to the display 106. Inside the electronic module 120, the head orientation sensor signal preprocessor 122, the eye camera video processor 124, and the display interface 126 are connected to a central processing unit 132. Also connected to the central processing unit 132 is a memory unit 134 and an interface and/or communications unit 138. The memory unit 134 can store multiple readings and results, which can be used for data logging, tracking of multiple users, and tracking of performance at various times. The interface and/or communications unit 138 can be connected to an external device 140. Transmission of signals between the communications unit 138 and the external device can be through a wired connection or a wireless connection using any connection method and/or protocol capable of being understood by anyone skilled in the art, including, but not limited to a serial protocol (such as USB), an ethernet protocol (such as TCP/IP), and a cellphone protocol (such as LTE). Additional elements that are not shown, but might be included in the electronic module 120 can be a battery and a power management module. The battery in the electronic module could be wirelessly charged. Communication between the electronic module 120 and the head worn unit can be through a wired connection or a wireless connection using any connection method and/or protocol including, but not limited to those described for the connection between the electronic module 120 and the external device 140.

Figure 2:
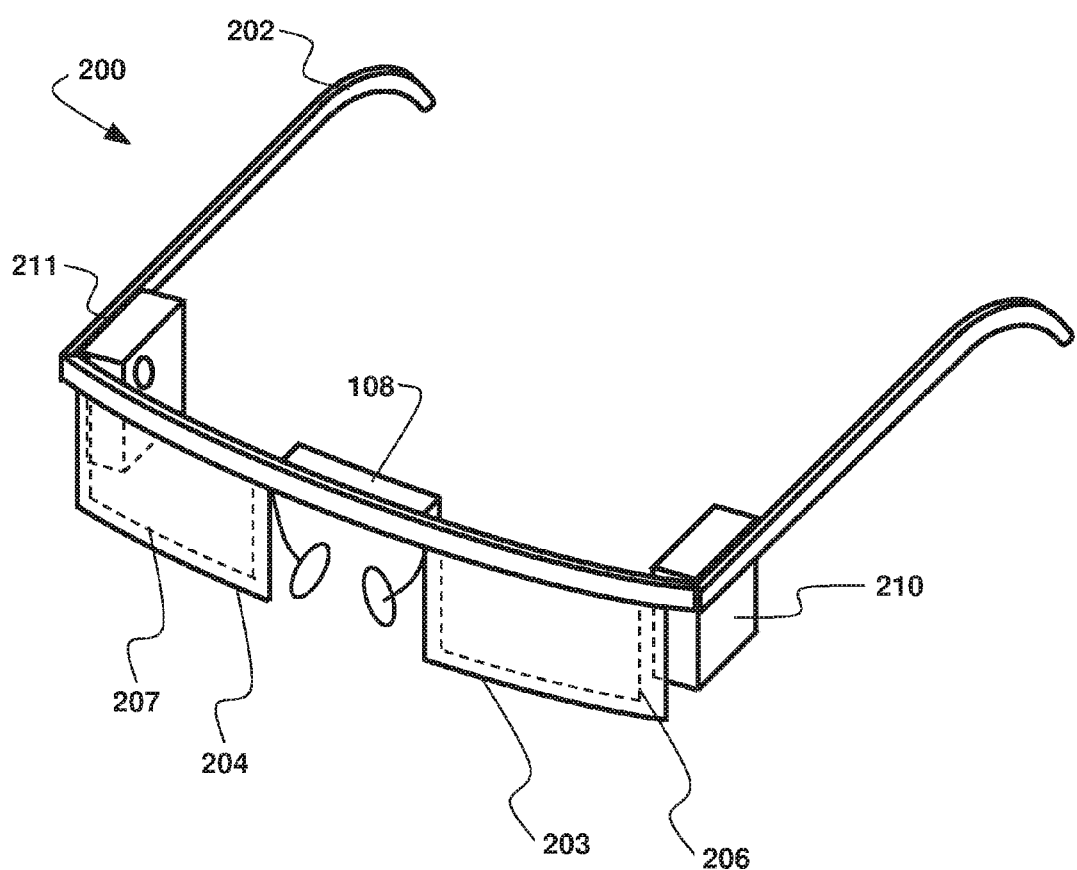
FIG. 2 shows an eyeglasses embodiment of a head-worn augmented reality unit.

FIG. 2 shows an eyeglasses embodiment of a head-worn augmented reality unit 200. The eyeglasses unit 200 shown in FIG. 2 is similar to the headband unit 100 shown in FIG. 1 and could have any of the features and attributes of the unit shown in FIG. 1. The eyeglasses unit 200 could be electronically coupled to an electronic module 120 in FIG. 1 and this electronic module 120 could be part of the eyeglasses unit 200, or the electronic module could be external to the eyeglasses unit 200 and communicate through a wired or wireless connection. The eyeglasses unit could be used for measurement of VOP or any related measurement or ocular, vestibular, or vestibulo-ocular function. The eyeglasses unit 200 comprises a spectacles frame 202, which serves as the equivalent of the head attachment element (headband) for the embodiment shown in FIG. 1, a left eyeglass 203, and a right eyeglass 204. The left and/or right eyeglasses could be lenses, they could be clear windows, or they could be translucent windows. Also shown are a left display 206 and a right display 207. In the embodiment shown in FIG. 2, the displays, 206 and 207, are see-through displays that are located between the left and right eyeglass, 203 and 204, and the eyes of the person. When the displays, 206 and 207, are in this location, it is not as obvious to an outsider that the unit 200 is an augmented reality unit. The displays, 206 and 207, could also be external to the left and right eyeglasses 203 and 204. There could be only one display, 206 or 207. The display could be off-bore and only visible in a person's peripheral vision, such as in the version of Google Glass® that was available in 2014-2015.

Further referring to FIG. 2, the eyeglasses unit also comprises a head orientation sensor located in the bridge 108, a left eye tracking digital video camera 210 and a right eye tracking digital video camera 211. All of these components can be connected similarly and in any configurations and combinations that were described with reference to FIG. 1.

Figure 3:
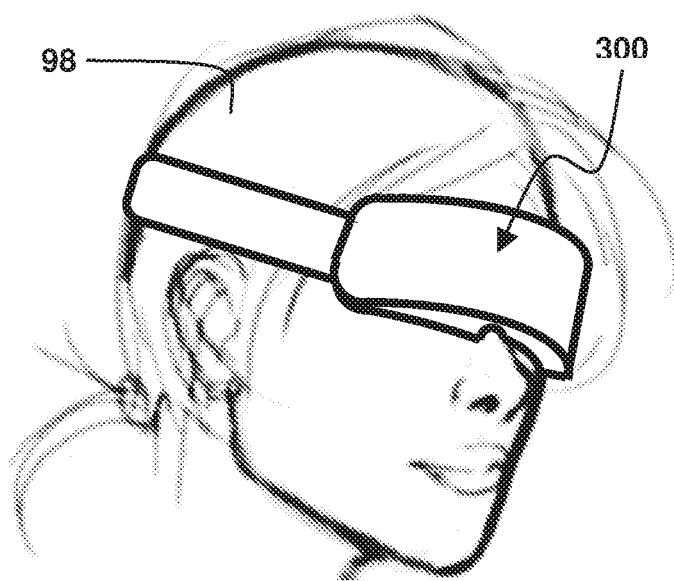
FIG. 3 shows a goggles embodiment of a head-worn virtual reality unit.

FIG. 3 shows a goggles embodiment of a head-worn virtual reality unit 300. In the augmented reality units of FIG. 2 and FIG. 3, the display is either see-through, or it is opaque, but only covering one eye or part of an eye. In the virtual reality unit, the display is opaque and the person 98 is typically completely immersed in the scene being displayed. Other than the difference in display, the goggles embodiment 300 can have many of the same elements and configurations that were described with respect to FIG. 1 and FIG. 2 including, but not limited to the head orientation sensor 108, the eye tracking video camera(s) 110, and the electronic module 120.

Figure 4:
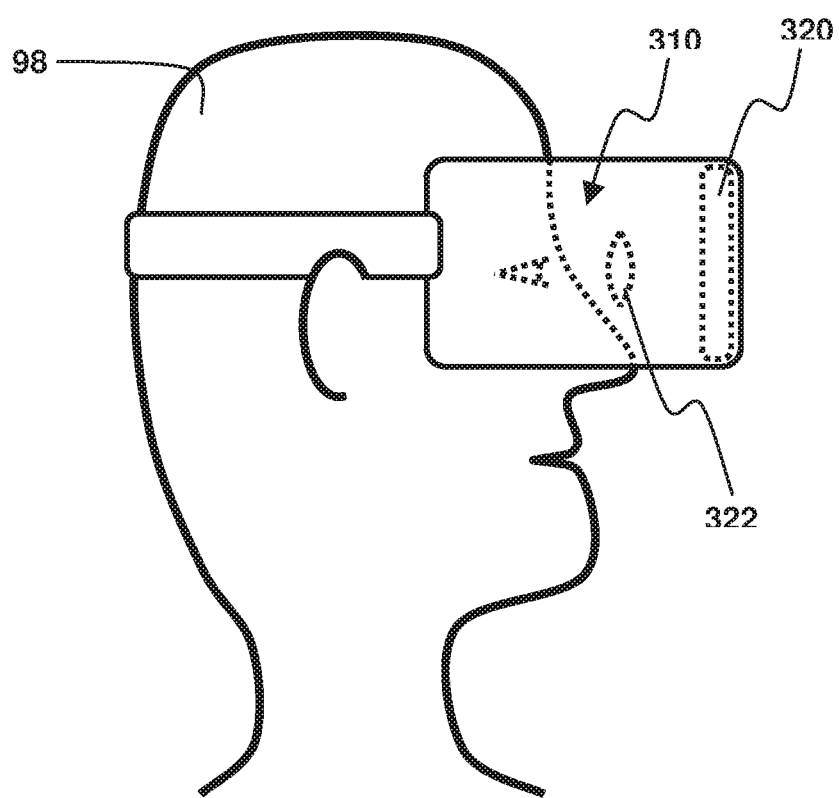
FIG. 4 shows head-worn virtual reality goggles comprising a smartphone.

FIG. 4 shows head-worn virtual reality goggles comprising a smartphone 310. These goggles 310 use the smartphone 320 to provide the display, the eye tracking digital video camera, and the head tracker functionality, as well as doing many, if not all, of the functions of the electronic module. To help the person's eyes focus on the display of the smartphone 320, these virtual reality goggles further comprise one or two lenses 322 that sit between the eyes of the person 98 and the smartphone 320.

Figure 5:
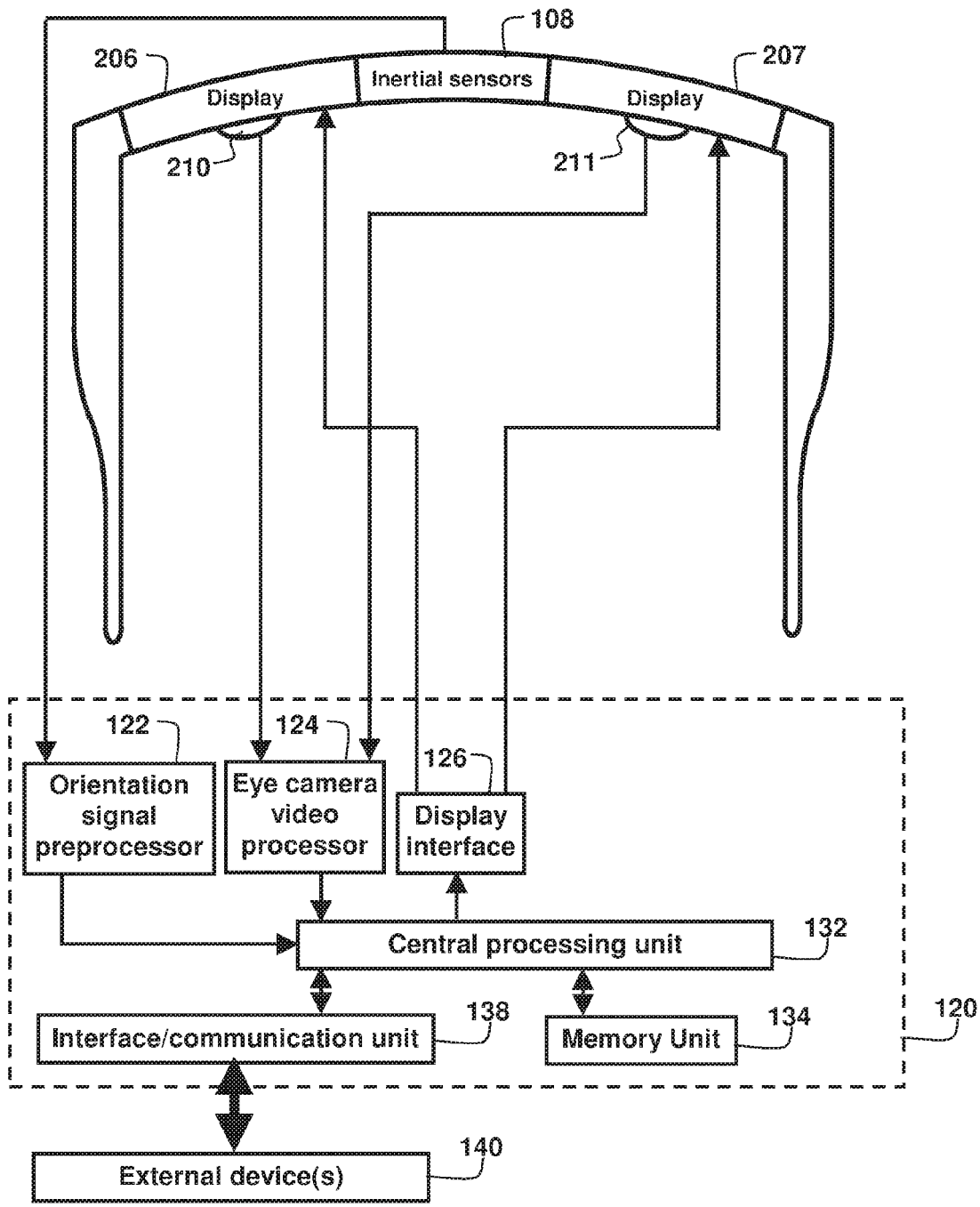
FIG. 5 shows a top view of an augmented reality or virtual reality system.

FIG. 5 shows a top view of an augmented reality or virtual reality system that also includes the main elements that were shown with respect to FIG. 1 to FIG. 4 including a head orientation sensor 108, a left display 206, a right display, a left eye tracking digital video camera 210, a right eye tracking digital video camera 211, an electronic module, an orientation signal preprocessor 122, an eye camera video processor 124, a display interface 126, a central processing unit 132, a memory unit 134, an interface/communication unit 138, and an external device 140.

Figure 6:
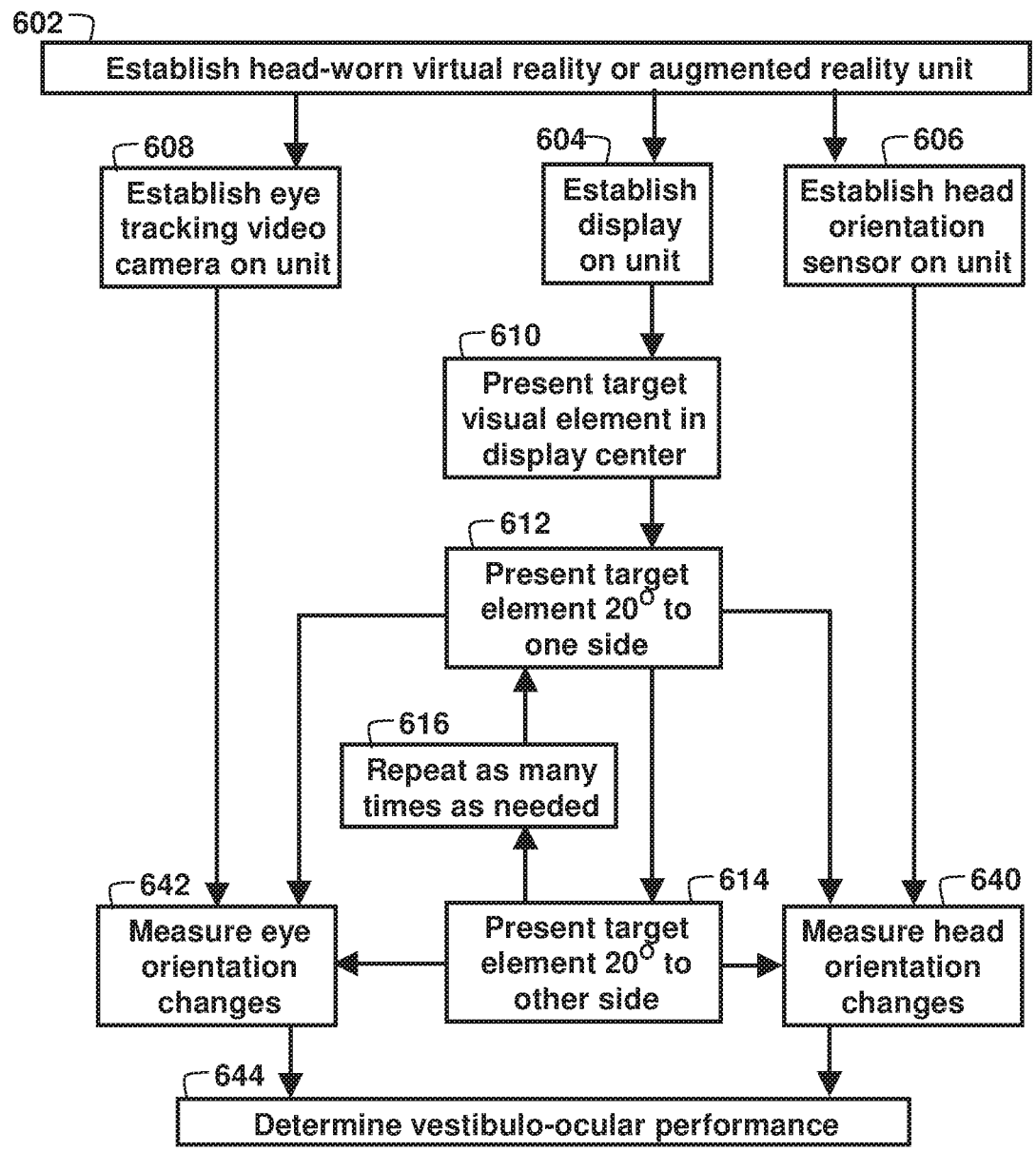
FIG. 6 shows a vestibulo-ocular performance calibration test method.

FIG. 6 shows a vestibulo-ocular performance calibration test that can be implemented in a head-worn AR or VR unit. This test comprises the following configuration and steps:

The head-worn AR/VR unit 602 comprises a display 604, a head orientation sensor 606, and an eye tracking video camera 608.

Head: In this test, the subject is asked to keep his/her head motionless or the head is constrained to keep it motionless. The head orientation sensor 640 is used to verify that the head is stationary.

Eyes: The subject is asked to track a visual target element of interest by moving his/her eyes. The eye sensor (typically a video camera) measures the subject's eye movement 642 as visual elements are displayed.

Display: The display background is subdued, plain, solid, and/or non-distracting. In this test, the display background is similar to the background that has been used in prior art VOR testing in which the subject is asked to look at a solid colored wall in the clinician's office which has a bright white circular dot (the target visual element of interest) projected on it. In the AR/VR embodiment of this test, the display background on the head-worn device is similar to the wall of the prior art test. The display also presents a target visual element of interest that is similar the projected white circular dot of the prior art clinical test. The target visual element of interest then behaves in the following way:
1. The target visual element is initially displayed centrally 610.
2. It is then displayed about 20 degrees off center on one side (left or right) as the central image is dimmed 612.
3. It is then displayed about 20 degrees off center to the other side as the image to the one side is dimmed 614.
4. This process of dimming the target visual element of interest on one side and displaying it on the other side is repeated as many times as needed 616.
5. This test can be conducted in the vertical, as well as the horizontal direction.

Processor: The processor in the AR/VR system then compares eye movement to timing and appearance/disappearance of visual elements on display, and the location of these visual elements to determine vestibulo-ocular performance 644. Performance could be measured as accuracy, gain, phase, symmetry, velocity, saccades, and/or visual acuity.

Figure 7:
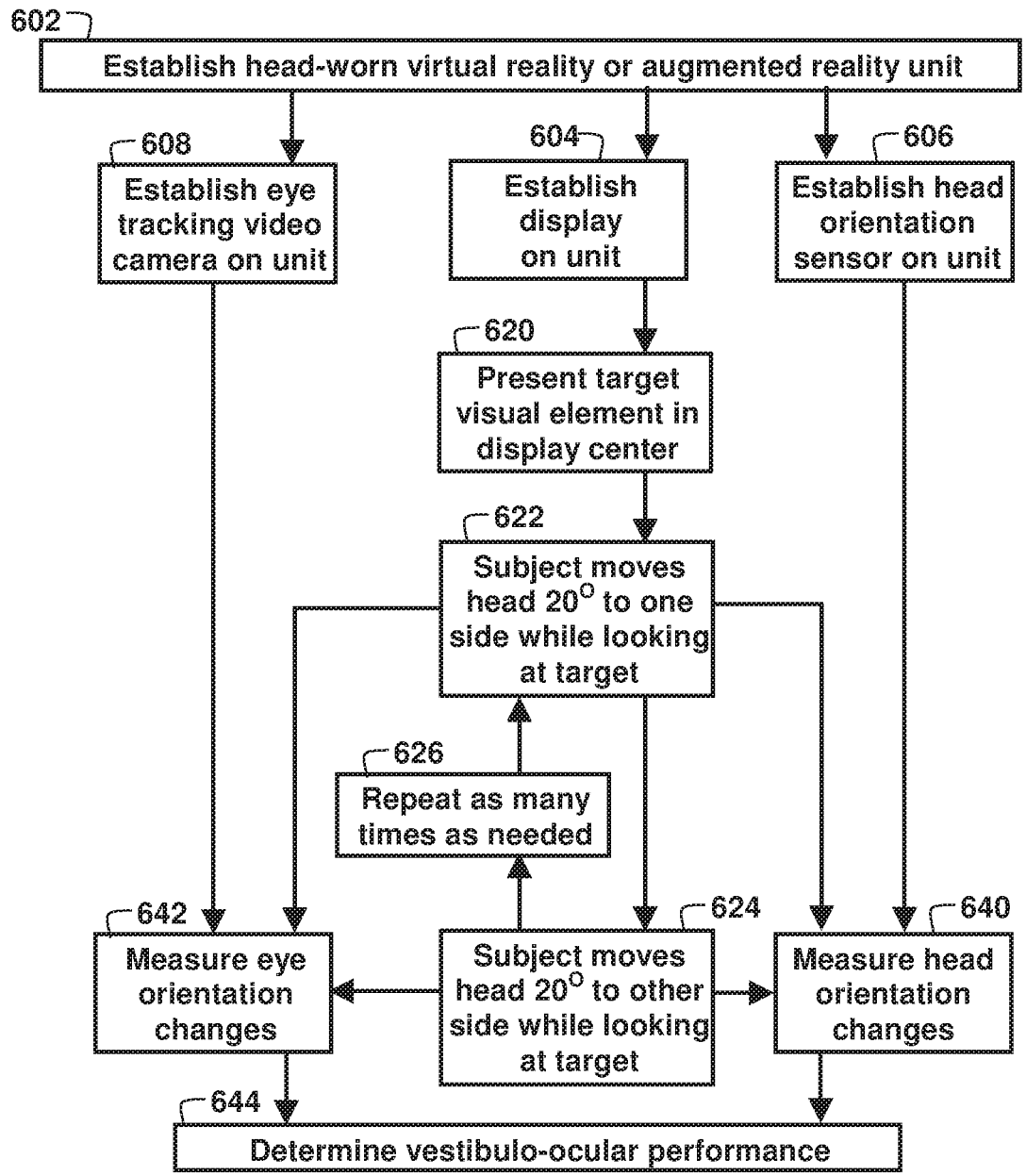
FIG. 7 shows a static active vestibulo-ocular performance test method.

FIG. 7 shows a static active vestibulo-ocular performance test that can be implemented in a head-worn AR or VR unit. This test comprises the following configuration and steps:

The head-worn AR/VR unit 602 comprises a display 604, a head orientation sensor 606, and an eye tracking video camera 608.

Display: In this test, the display is static—neither the background nor the target visual element of interest move or change in any way. The display comprises a subdued background and a centered white circular dot 620, similar to what was described with reference to the test shown in FIG. 6A.

Head: In this test, the subject is asked to actively move his/her head about 20 degrees each time he/she is given a cue signal. The head orientation sensor measures changes in head pitch, roll, and/or yaw 640.

Eyes: The subject is instructed to keep his/her eyes focused on the target visual element as the head moves. The eye sensor (typically a video camera) measures eye movement relative to head movement 642.

Cues are provided to tell the subject when to move the head. These cues can be audio cues. The cues could be haptic (i.e. tap on the hand). The cues could be visual (i.e. change of color or intensity of the visual target element of interest). The cues are typically timed randomly so the subject doesn't try to anticipate the timing.

The test sequence is as follows:
1. The subject is instructed to move the head 20 degrees in one direction when a first cue is given, and to hold the head in this new position 622.
2. The subject is instructed to move the head back 20 degrees when the second cue is given 624.
3. The subject is instructed to move the head the first direction a second time when the third cue is given.
4. The process is repeated as many times as needed 626.
5. This test can be conducted in the vertical, as well as the horizontal direction.

Processor: The processor in the AR/VR system then compares eye movement to timing and appearance/disappearance of visual elements on display, and the location of these visual elements to determine vestibulo-ocular performance 644. Performance could be measured as accuracy, gain, phase, symmetry, velocity, saccades, and/or visual acuity.

Figure 8:
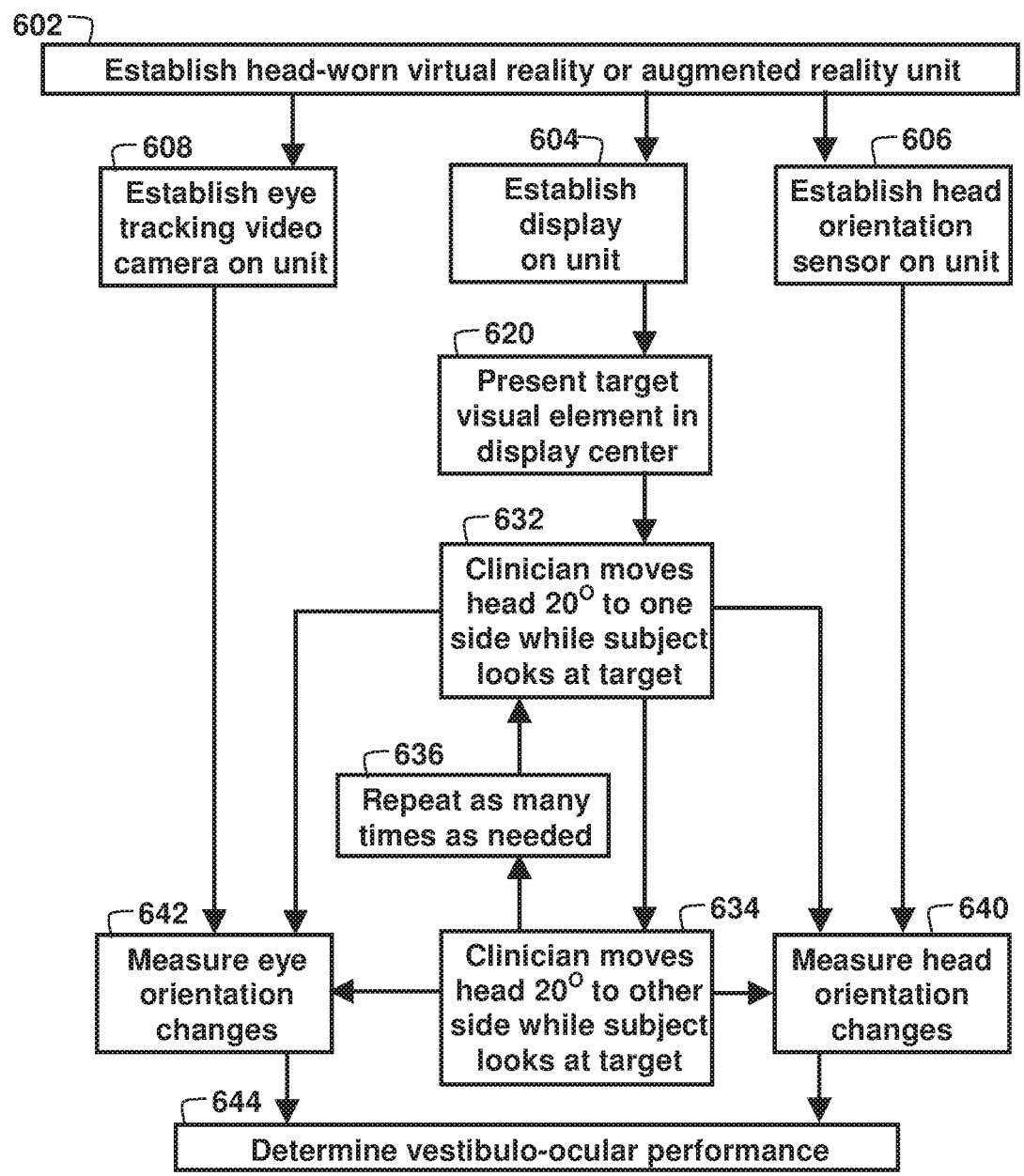
FIG. 8 shows a static passive vestibulo-ocular performance test method.

FIG. 8 shows a static passive vestibulo-ocular performance test that can be implemented in a head-worn AR or VR unit. This test comprises the following configuration and steps:

The head-worn AR/VR unit 602 comprises a display 604, a head orientation sensor 606, and an eye tracking video camera 608.

Display: In this test, the display is the same as for the test described with reference to FIG. 6B, with a target visual element presented in the center 620.

Head: In this test, the clinician holds the subject's head and moves it about 20 degrees each time 632. The head orientation sensor measures changes in head pitch, roll, and/or yaw 640.

Eyes: The subject is instructed to keep his/her eyes focused on the target visual element as the head moves. The eye sensor (typically a video camera) measures eye movement relative to head movement 642.

The test sequence is as follows:
1. The clinician moves the subject's head 20 degrees in one direction and then holds it in this new position 632.
2. The clinician then moves the head back 20 degrees and holds it 634.
3. The clinician moves the head the first direction a second time.
4. The process is repeated as many times as needed 636.
5. This test can be conducted in the vertical, as well as the horizontal direction.

Processor: The processor in the AR/VR system then compares head movement and eye movement to determine vestibulo-ocular performance 644. Performance could be measured as accuracy, gain, phase, symmetry, velocity, saccades, and/or visual acuity.

There can be many additional embodiments of the basic vestibulo-ocular performance tests described with reference to FIG. 6, FIG. 7, and FIG. 8. Some of these embodiments can include combinations of the variations listed here:

a. The visual target element (traditionally a white dot) can be any other shape, size, or coloring or have any other features capable of being understood by anyone skilled in the art. Examples of these variations in the target visual element could include:

A different shape (such as a shape comprising a cross hair);
Different contrast, either more or less;
Different intensity;
Different size;
Different focus, either more in-focus or out of focus;
Having one or more features in the visual element that move relative to the rest of the visual element;
The appearance of a natural object (such as a baseball, a basketball, or a bird); and/or;
Any combination of any of the above.

b. The test shown in FIG. 7. or FIG. 8 could be run with the target visual element not being stationary. This would make the overall test more similar to a natural environment in which the head, the eyes, and the visual world are all moving relative to one another and relative to a stationary reference frame at all times. When implemented on a display in an AR/VR environment, this would mean that the target visual element could:

Move with the head movement;
Move contrary to the head movement;
Move perpendicular to head movement; and/or Move in any random pattern not associated with head movement c. The background (traditionally a subdued, plain, solid, and/or non-distracting wall of a clinician's) office could be presented on the display of the AR/VR system as any other background capable of being understood by anyone skilled in the art. Examples of variations of the background can include embodiments in which the background is more natural and similar to actual scene and/or any of the variations in the following list:

The background can be completely static

The background can have moving and/or flashing elements

The background can be enhanced with auditory distractions consistent with the imagery being displayed The background can be in or out of focus The background can be low intensity/contrast or high intensity/contrast relative to target of interest DVA (dynamic visual acuity) and FVS (foveal visual stability) can be tested using a system and method similar to the vestibulo-ocular performance (VOP) test shown in FIG. 7. The following are the main elements of a DVA or FVS test performed in this way using a VR or AR environment:

Step 1. Perform a routine vision test by presenting a Snellen chart, or something similar, using the display of the AR/VR unit. This is needed to establish a baseline visual acuity in a static environment. This static test does not necessarily need to be done with a Snellen chart (the standard chart used by optometrists and ophthalmologists), it could also be done by asking the subject to identify characters of various sizes, positions, and/or locations.

Step 2. The subject is presented a visual element in the display center in a manner similar to step 620 of FIG. 7, but in the case of a DVA or FVS test, the target visual element also comprises a character that the subject must identify.

Step 3. The size and character of the target visual element in the display center changes at random times while the subject is performing the steps described at 622 and 624 in FIG. 7.

Step 4. The subject speaks out the character observed each time it changes.

A VR/AR environment can also be used for positional testing. For example, VR goggles can be configured to display a background that has illumination, but no definable image that might provide orientation information to the subject. The subject, could then be asked to turn the head left, right, lie supine, while supine head turns right, head turns left, then turn the body (roll) right and turn the body (roll) left. During each positional change, the eyes are tracked using the AR/VR system to look for abnormal eye movements. If a target visual element was visible during this testing the nystagmus would be suppressed. However, elements with poor contrast can be displayed to provide a more immersive test environment. Visual elements in this instance should not have defining characteristics that might enable eye fixation.

A subject can be tested for BPPV using the method shown in FIG. 8 with the clinician moving the head in a specific pattern that allows the individual semicircular canals to be tested. Note that this means the head is not moved the 20 degrees side-to-side, but is instead moved based on standard protocol for the specific semicircular canal being tested.

Figure 9A:
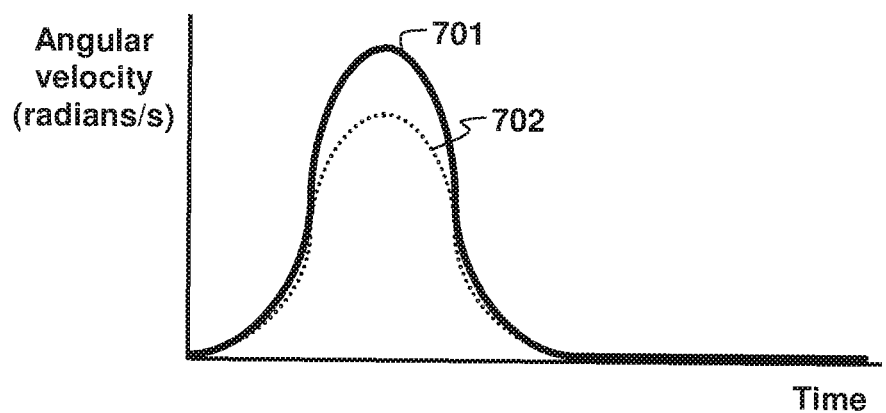
FIG. 9A shows vestibulo-ocular gain measurement.
Figure 9B:
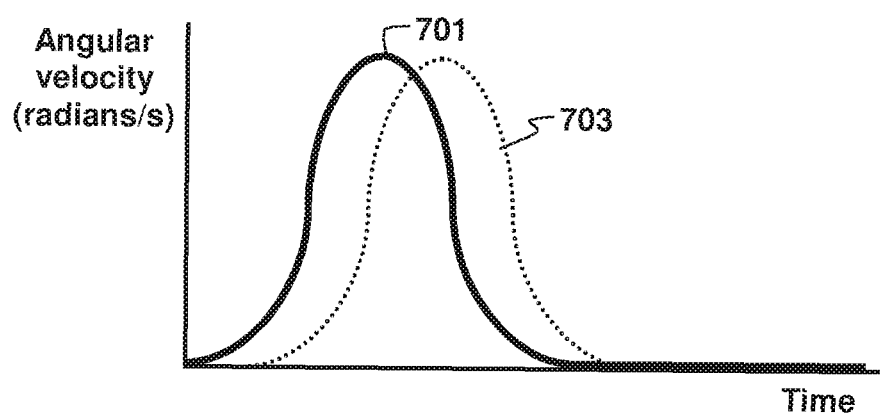
FIG. 9B shows how vestibulo-ocular phase is measurement.
Figure 9C:
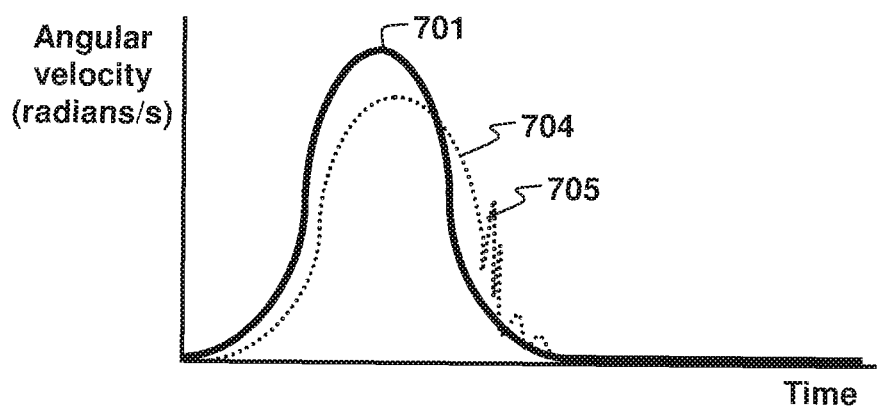
FIG. 9C shows vestibulo-ocular saccades.

FIG. 9A, FIG. 9B, and FIG. 9C provide graphs of time versus angular velocity that show how ocular response to a vestibular input can be measured. In these figures, the input is a rotation of the head, which is shown as the solid line at 701. This head rotation information would typically be measured using the head orientation sensor 108 that has been shown in FIG. 1, FIG. 2, and FIG. 5. The output is the eye response to the head rotation, which is shown as the dotted line at 702, 703, and 704, and would typically be measured using the eye sensor, which is typically an eye tracking digital video camera 110, such as that shown in FIG. 1. The actual eye response is in the direction opposite of the head rotation, 701, but it has been plotted in the same direction to make it easier to compare the input and output of a person's vestibulo-ocular system. In FIG. 9A, the velocity of the eyes is slower than that of the head, which results in a gain of less than 1.0. In FIG. 9B there is a delay between the rotation of the head and the rotation of the eyes, which results in a phase lag. In FIG. 9C, the eye rotation also lags the head rotation as shown at 704, but is caught up by saccades 704 near the end of the rotation.

Figure 10A:
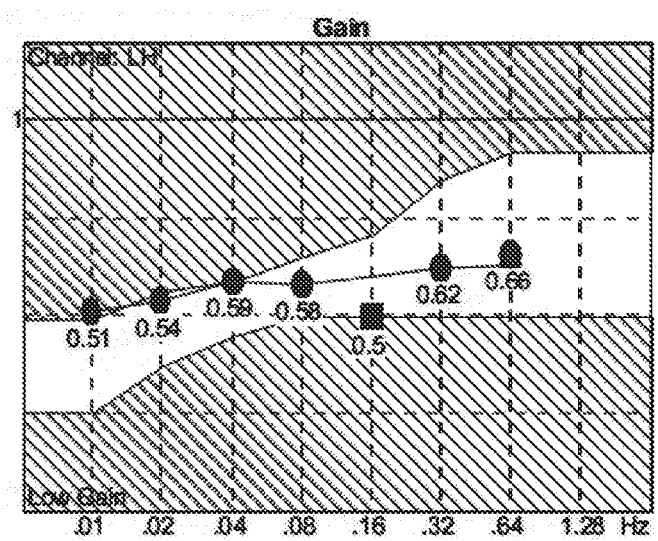
FIG. 10A illustrates an example of the left eye gain of a healthy person's vestibulo-ocular response to motion between 0.1 Hertz and 1.28 Hertz.
Figure 10B:
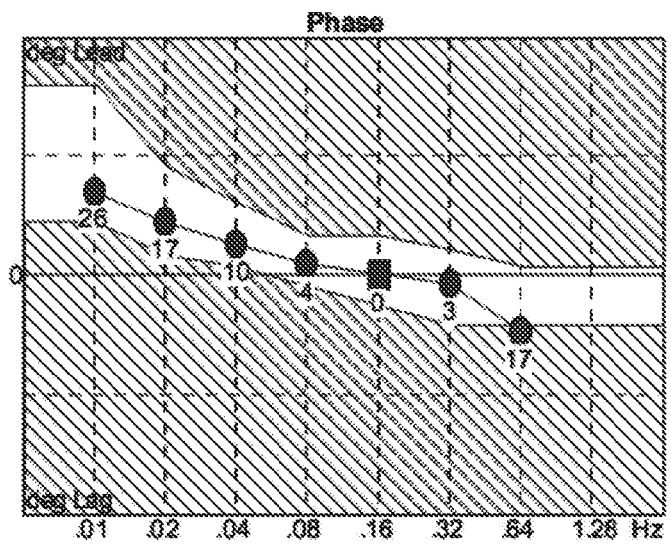
FIG. 10B illustrates an example of the phase lead and lag for a health healthy person's vestibulo-ocular response to motion between 0.1 Hertz and 1.28 Hertz.
Figure 10C:
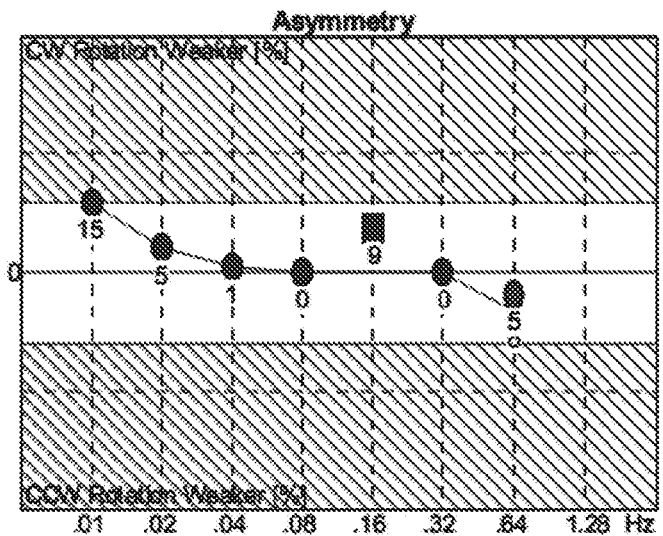
FIG. 10C illustrates an example of the asymmetry readings between counterclockwise and clockwise horizontal rotation of a healthy person's vestibulo-ocular response to motion between 0.1 Hertz and 1.28 Hertz.

The measures shown in FIG. 9A, FIG. 9B, and FIG. 9C, can be plotted at different frequencies and compared between the left eye and the right eye to create the plots shown in FIG. 10A, FIG. 10B, and FIG. 10C., which illustrate some typical eye responses to oscillation of a healthy person's head (e.g. vestibulo-ocular responses) in a horizontal plane at frequencies ranging from 0.1 Hertz (1 cycle every 10 seconds) to 1.28 Hertz (approximately 5 cycles every 4 seconds). More specifically, FIG. 10A shows the gain at these frequencies, FIG. 10B shows the phase lead and lag at these frequencies, and FIG. 10C shows the relative symmetry (or asymmetry) between clockwise and counterclockwise oscillations. It should be noted that 0.1 Hertz to 1.28 Hertz is typical for the range of frequencies being used by prior art VOR testing systems. The embodiments described in this disclosure can include any frequency in the range of 0.01 Hertz (1 cycle every 100 seconds) to 15 Hertz (approximately 15 cycles every second).

FIG. 11A, FIG. 11B, FIG. 12, FIG. 13, FIG. 14, and FIG. 15 relate to targets or visual elements that could be presented on a VR or AR display to facilitate measurement and/or improve vestibular, ocular, and/or vestibulo-ocular function. These targets or visual elements can be designed to enhance the eye fixation on the displayed image when the head is motionless and the visual element is in motion. These targets or visual elements could also be designed for when the head is in motion and the visual element is motionless or when both the head and the visual element are in motion. In either VR or AR, the displayed targets or visual elements can be static in a position or location or the displayed targets or visual elements can be dynamically changing in position, depending on the specific test being performed or rehabilitation method being used. The targets or visual elements, upon which the eyes are attempting to focus, can be of a variety of colors, sizes, shapes, and forms. They can change in color, size, shape, and form. They can contrast with other items being displayed to be more or less dominant in order to provide visual weight to enable fixation. These targets or visual elements can use specific colors with more saturation and can change in scale and proportion, all in an effort to draw the fovea toward a specific point of fixation on the target or visual element. Without using such enhancements to what is displayed, when performing VOR, DVA, or other oculomotor testing, the eyes tend to wander and have more microsaccades, which decrease the fixation ability and lessens the attentiveness of the person performing the test and the accuracy of testing. Generally, it is important to have some small point of focus to lessen the microsaccades and enhance the fixation ability. These same targets or visual elements can be used for VOR re-training when a VOR abnormality exists.

The ideas expressed in the previous paragraph can best be explained by looking at some examples. FIG. 11A shows an example of a target or visual element in the form of a soccer ball 902. This soccer ball could be part of an existing scene viewed on a VR or AR display or viewed through an AR display or the soccer ball could have been added to the scene. The soccer ball could be spinning, which might make the patter on the ball distracting. FIG. 11B shows the visual element (soccer ball) of FIG. 11A that has been altered by defocusing the ball 904 and superimposing a target in the form of a cross-hair 906 that is easier for the eyes to focus on. It would be easier for the eyes to focus on the element shown in FIG. 11B than the element shown in 11A due to the shape, size, contrast, and suppression of the pattern on the ball. Although this example has been done using a black and white image, color and color contrast can be more effective. For example, the visual element seen in the VR or AR platform display could be a red colored ball and within the center of the ball a dark cross-hair surrounded by a lighter yellow circle could be placed. This strongly contrasted central focal point could help the eye focus on a specific point and lessen the "eye scanning" while undergoing VOR testing or VOR re-training. In another example, the element being viewed can be in the shape of a familiar object, such as a basketball, football, helmet or object used in one's occupation. It can also have a centered focal point, created by high contrast and high color saturation compared to the surrounding background to maintain the foveal fixation duration attractiveness and lessen microsaccades.

FIG. 12 shows a scene that can be used for optokinetic testing in a virtual or augmented environment. In traditional optokinetic testing, a person's head is motionless while seated inside a moving drum with alternating black and white vertical lines or a hand held drum with alternating black and white vertical lines is placed in front of the person. The drum is slowly rotated. The alternating lines induce nystagmus and cause visually induced motion sickness. The movement of the eyes is measured as the drum rotates left and then right. Measurements can be at different drum speeds. This same test can be performed using an AR or VR platform by creating a visual image that includes elements that work just like the vertical lines in the drum. Examples of natural scenes that are similar to the drum with lines can include examples such as being seated in a car and watching a train go by or driving and watching the telephone poles move by, such as the scene 910 shown in FIG. 12. Similarly flying objects can be visualized as moving across the visual field or along another plane of motion beside the person. These visual elements can also change in size, color or other dimensions, as the person gets closer to the virtual object or further from the visual element. Motion can occur in any direction relative to the person, as the eye movement is being assessed and measured.

Figure 13:
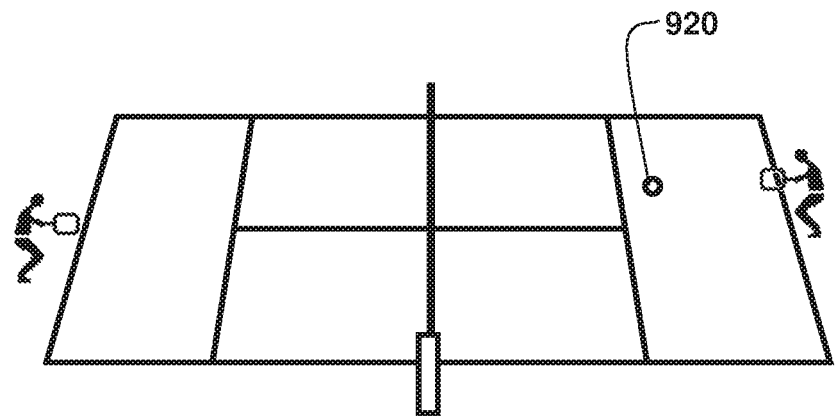
FIG. 13 shows a scene that can be used for testing eye-tracking performance in a virtual or augmented environment.
Figure 14:
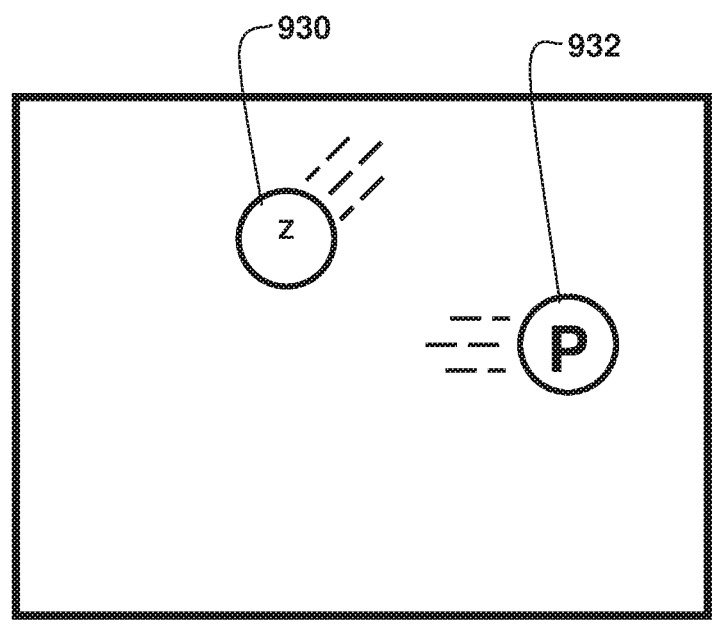
FIG. 14 shows a scene that can be used for dynamic visual acuity testing in a virtual or augmented environment.
Figure 15:
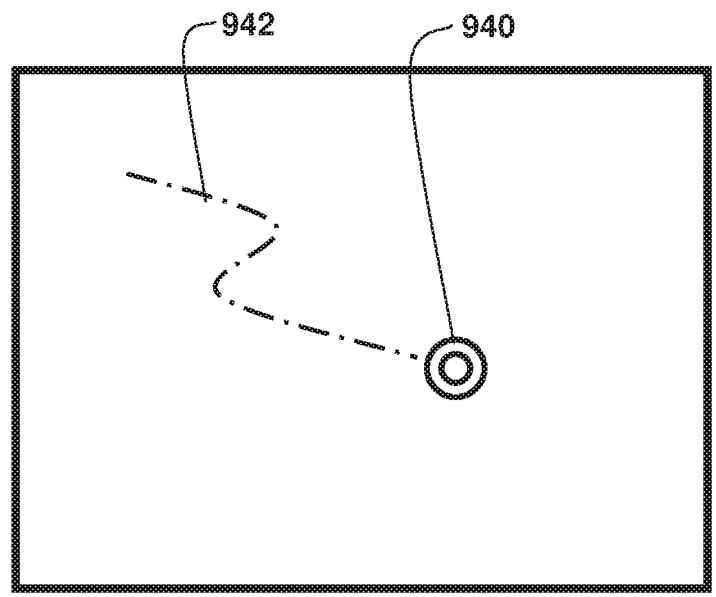
FIG. 15 shows a scene that can be used for scan path tracking in a virtual or augmented environment.

FIG. 13, FIG. 14, and FIG. 15 illustrate other AR/VR display scenes that can be used for VOR/DVA testing. These scenes can include a test environment comprising natural background features combined with a visual element or target whose shape, color, size, motion, or other attributes have been selected or added to facilitate testing of vestibulo-ocular performance. For example, if the VOR is being tested on a basketball player, the background features may be a basketball court surrounded by fans, who are yelling and moving. The visual element to be tracked could be the basketball and VOR testing can be virtually tested with the ball as the target of interest being in motion. This would be a realistic method of assessing VOR function. DVA measurement can also be performed with dynamic changes of the target or visual element of interest, requiring the person to identify characteristics of the element while it is in motion and the person is in motion and comparing this to the SVA prior to the onset of the DVA test. FIG. 13 shows a scene for this type of VOR testing might look like. In the example shown in FIG. 13, the static scene is the tennis court and the moving target is the tennis ball 920. FIG. 14 shows letters that could be superimposed onto the moving element (such as the tennis ball in FIG. 13) to test DVA. The target visual element 920 in FIGS. 13, 930 and 932 in FIG. 14, or 940 in FIG. 15 could move in different trajectories, the letters could be of different sizes, and the ball could move at different speeds and accelerations to provide a meaningful test as shown by comparing visual element 930 with visual element 932. The targets can be rapidly moving is a specific plane or scan path (such as watching a tennis ball move across the court or with tracking tests that have a rotating target visual element.

DVA testing could be performed with lettered optotypes and as the head rotates back and forth, the letters can rotate in position. Alternatively, numbers can be used as well as other familiar images of objects. The images can also be native or natural to the background environment displayed. As the head rotates back and forth, the target or visual element is more difficult to visualize. If there is a VOR abnormality, for example the eyes will not be able to focus on the target or visual element of interest and will subsequently have less fixation and more errors in identifying a visual element. Measurement can also be performed with the visual element stationary and the head in motion or both the visual element and head in motion, which would be more realistic with everyday experiences. Static visual testing (SVT) can be performed to obtain a normal visual test. The visual acuity can be obtained, while the head and the visual element, or optotype being displayed are both motionless. Similar to a standard eye exam, an AR/VR platform can enable a person's static visual acuity (SVA), a component of DVA testing, by asking a person to identify a multitude of images or optotypes (letters, symbols, characters, figures of different sizes, shapes, orientation) on the visual screen.

Smooth pursuit testing can be performed with similar targets or visual elements of interest as have been described previously. Smooth pursuit testing has traditionally been performed with the head motionless and the eyes following a moving light or finger moving across a visual field. FIG. 15 shows a scene that can be used for scan path tracking in a virtual or augmented environment. An enhanced target visual element 940 can be sent across the scene along a specific path 942, while the measured eye movement follows the visual element. The path of these visual images or elements can assume any pattern, such as a zigzag, a saw toothed, or a square wave, or have a scan path that is snake-like, curved, sinusoidal or rotational to provide a realistic and natural method of assessment of visual pursuit.

Figure 16:
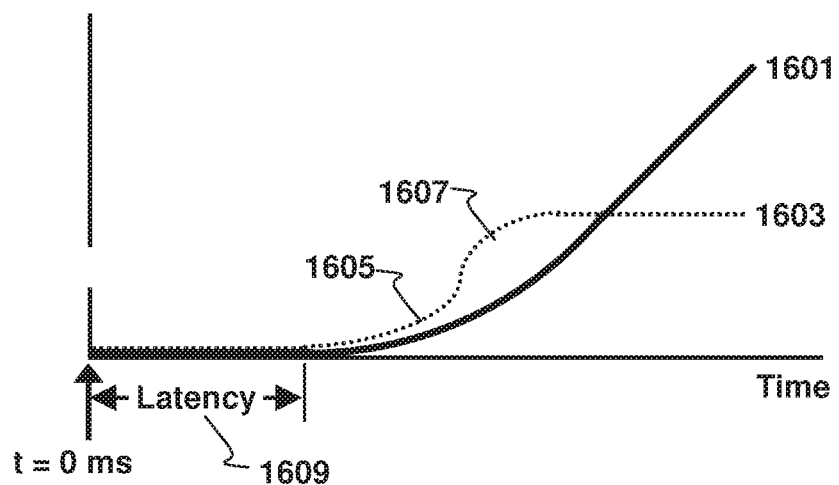
FIG. 16 shows the relationship between target movement, eye position, eye velocity, and eye acceleration for smooth pursuit.

FIG. 16 shows the relationship between target movement, eye position 1601, eye velocity 1603, and eye acceleration for smooth pursuit. The time when the target is moved is identified as t=0 ms. The eye position 1601 and eye velocity 1603 can then be tracked as a function of time. Latency 1609 is the delay from the time the target moves to the time the eye starts to move. Then the eye velocity 1603 will first accelerate 1605 and decelerate 1607 until the eye velocity 1603 matches the target velocity.

Figure 17A:
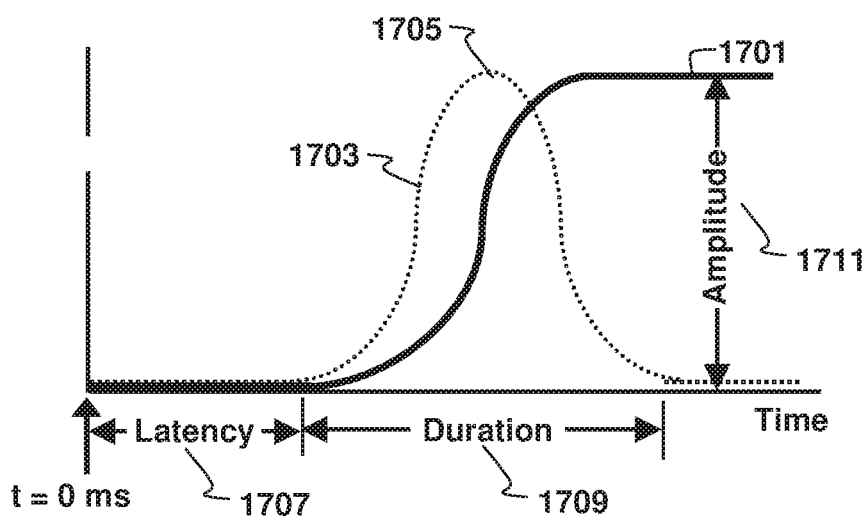
FIG. 17A shows the relationship between target movement, eye position, and eye velocity for a saccade.
Figure 17B:
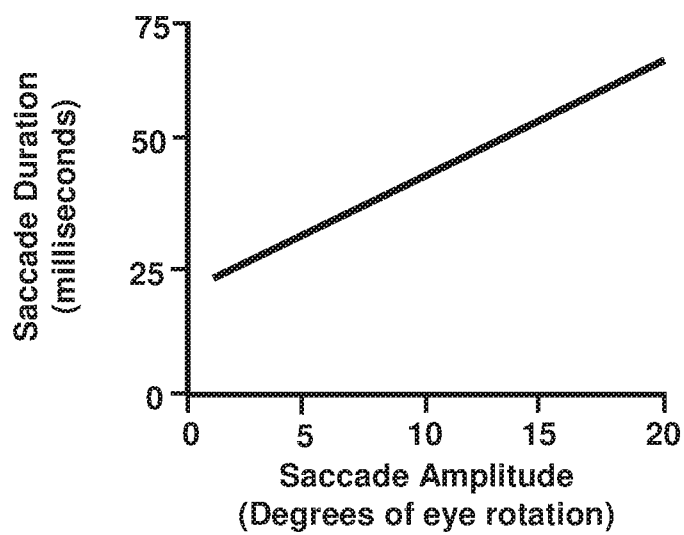
FIG. 17B shows the typical relationship between saccade amplitude and saccade duration.

FIG. 17A shows the relationship between target movement, eye position 1701, and eye velocity 1703 for a saccade. The time when the target is moved is identified as t=0 ms. The eye position 1701 and eye velocity 1703 can then be tracked as a function of time. Latency 1707 is the delay from the time the target moves to the time the onset of a saccade. As shown, the saccade eye velocity 1703 increases, reaches a peak velocity 1705, and then returns to zero. The length of time from the start to the end of this velocity curve is called the saccade duration 1709. The saccade eye position 1701 changes during this duration 1709 to reach a new position that differs from the initial eye position by a distance that can be defined as a saccade amplitude 1711. FIG. 17B shows the typical relationship between saccade amplitude and saccade duration.

Note that any of the testing described in any of these drawings can be done with static targets or visual elements being viewed, or with dynamic targets or elements. The images or elements viewed may be familiar objects, such as balls, or objects more familiar to one's occupation. The visual target or visual elements may be displayed in a manner that is native or natural to the background.

3. Eye Tracking

To measure specific eye responses, such as the VOR, DVA and/or DVS both eye tracking and head tracking measurements are required. Eye tracking is the process of measuring either the point of gaze (where one is looking) or the motion of an eye relative to the head position. An eye tracker is a device for measuring eye positions and eye movement. Eye tracking and/or measurement can be done in many ways, examples of which include: (a) using a device such as a contact lens that is attached to the eye; (b) using a head worn device; (c) using a remote system; or (d) using a sensor attached to another part of the body, such as a hand-held device or a smart watch. The eye tracking and/or measurement can be done: (a) in a non-contact fashion with the use of a light source (invisible light, such as with the use of an infra-red camera or light, or visible light); by using a video camera or other sensor system designed to visually capture and record the eye movement activity; (c) with a marker or sensor on a contact lens; and/or (d) with a magnetic system such as one using magnetized contacts and an external detector. If one or more video cameras are to be used for eye tracking, it is desirable to have a sampling rate at least 30 frames per second (30 Hz) and preferably at least 50/60 Hz. Many video-based eye trackers have sample rate of at least 250, 350 or even 1000/1250 Hz. These higher sampling rates may be needed in order to capture fixation of eye movements or correctly measure other saccade dynamics. In embodiments of the present invention, the video camera contained in a smart phone or tablet device could be used as an eye tracker. Since the eyes are not located at the center of head rotation, any rotation of the head requires translation of the eye relative to visual targets. For targets at optical infinity, this translation does not require any compensatory movement. For near targets this translation becomes significant and compensatory eye movements are required for stable gaze and at close target distances. One must also compensate when measuring VOR and the compensation requires knowing the distance between the center of rotation and the visual target. The relative location of the center of rotation of the eye with respect to the head mounted head tracker receiver varies for each subject because of anatomical considerations.

If a light source is used for eye tracking and/or measurement, the light source is directed toward the eye or eyes and a camera tracks the reflection of the light source and visible ocular features such as the pupil features and/or cornea surface reflection(s). The information can then be analyzed to extract eye rotation and ultimately the direction of gaze from changes in reflections. Additional information such as blink frequency and changes in pupil diameter can also be detected by the eye tracker. The aggregated data can be stored and written to a file that is compatible with eye-tracking analysis software. Graphics can be generated to visualize such findings. Beyond the analysis of visual attention, stored eye data can be examined to measure the cognitive state or other information.

A camera can be used as a sensor for detecting light in high resolution. When tracking and/or measuring the eye activity or eye movement, such as the VOR, an IR or video camera may be used and can be comprised of a single camera system or a multiple camera system. The camera can be located on the framework of the head worn device or within the lens material, or in the contacts being worn. If using a hand held device, the video camera can be located remotely in the device being held, mounted or worn elsewhere on the body. The camera control unit can be activated by such options as: an external wireless signal, a touch unit, rapid head movement or voice activation. The control unit can also be timer actuated, triggered by an eye blink for a defined period of time, or by placing the device on the head (e.g. putting on the head-worn unit). The eye tracking system can be mounted on a head worn device, on eyeglasses framework, or partially within the lens of eyeglass or contact lens on in a hand held mobile smart device, such as a smart phone, smart pad, or limb worn computer system.

The eye tracking and/or measuring system may include hardware such as an infrared camera and at least one infrared light source, a video tracking system and recorder. The infrared camera may be utilized by the eye tracking system to capture images of an eye of the wearer. The video images obtained by the infrared camera regarding the position of the eye of the wearer may help determine where the wearer may be looking within a field of view of the head mounted display used in the system. The infrared camera may include a visible light camera with sensing capabilities in the infrared wavelengths. Infrared light or radiation is a longer-wavelength radiation than visible light. It exists just outside of the spectrum of visible light. Heat, or thermal energy, is a common source of infrared light. An infrared camera is a device specially designed to detect and display the sources of this kind of light. A thermal infrared camera converts the heat detected into electrical signals, which are then projected in an image. Many types of night vision cameras are based on infrared light. A human body will always emit heat, and infrared cameras will detect this radiation.

The infrared light source can include one or more infrared light-emitting diodes or infrared laser diodes that may illuminate a viewing location, i.e. an eye of the wearer. Thus, one or both eyes of a wearer of the system may be illuminated by the infrared light source. The infrared light source may be positioned along an optical axis common to the infrared camera, and/or the infrared light source may be positioned elsewhere. The infrared light source may illuminate the viewing location continuously or may be turned on at discrete times.

The optical system may include components configured to provide images to a viewing location, i.e. an eye of the wearer. The components may include a display pane, a display light source, and optics, such as mirrors or refractive lenses. These components may be optically and/or electrically-coupled/connected to one another and may be configured to provide viewable images at a viewing location. One or two optical systems may be provided in the system. In other words, the head mounted display may allow the wearer to view images in one or both eyes, as provided by one or more optical systems. Also, the optical system(s) may include an opaque display and/or a see-through display connected to the display panel, which may allow a view of the real-world environment while providing superimposed virtual images. The infrared camera or video camera, using visible light, coupled to the eye tracking system may be integrated into the optical system with a data storage and logging recorder.

Video-based eye trackers typically use the corneal reflection (the first Purkinje image) and the center of the pupil as features to track over time. A more sensitive type of eye tracker, the Dual-Purkinje eye tracker uses reflections from the front of the cornea (first Purkinje image) and the back of the lens (fourth Purkinje image) as features to track. A still more sensitive method of tracking is to image features from inside the eye, such as the retinal blood vessels, and follow these features as the eye rotates.

Eye tracking data can also be collected using a multi-camera eye gaze tracker, which is based on one-camera gaze estimation algorithm. Using an algorithm, the 3D eyeball position can be estimated by the two corneal surface reflections (or glints) of the IR lights. Each camera can estimate the gaze independently and can allow large head movement. The accuracy of this system is less than 1 degree.

Eye tracking using binocular horizontal and vertical eye position estimates can be derived from the relative positions of multiple corneal reflections and the center of the pupil. By using two eye landmarks (corneal surface reflections and pupil center) whose relative position are invariant under translation, the angular position of the eye independently of lateral motion of the video system relative to the head is able to be estimated. The optical components can be mounted on an eyeglasses frame or goggles.

The light source can be infrared and can be directed toward the eye or eyes. The camera can be used to track the reflection of the light source and visible ocular features such as the pupil features, cornea reflection features or retinal data imaging. The collected data from the eye tracking system can be used to measure the movement features of the eyes or eyelids or rotation of the eye, acceleration/velocity of the eye movement, duration of the eyelid closure, rate of the eyelid closure and the direction of gaze. Additional information such as blink frequency and changes in pupil diameter can also be detected by the eye tracker. Aggregated eye tracker data can be written to a file for later analysis. Stored eye tracker data can be used to analyze the visual path across an interface such as a computer screen. In this case, each eye data observation is translated into a set of pixel coordinates. From there, the presence or absence of collected eye data points in different screen areas can be examined. This type of analysis is used to determine which features are seen, when a particular feature captures attention, how quickly the eye moves, what content is overlooked and virtually any other gaze-related data. Eye position is extracted from video images and graphics are often generated to visualize such findings. Search based on an electro-oculogram may be used. When using a video-based eye tracker, the camera can be focused on one or both eyes and used to record eye movement as a viewer looks at some kind of stimulus.

A thin prism can be used between the eye and a camera system, which acts as a light-guide altering the imaging path between the camera and the eye. The use of a thin prism can also provide on-axis illumination. This arrangement can enable an eyeglass like eye tracking device, which captures a frontal (i.e., on-axis) or near frontal image of the eye to have a visually appealing form factor.

In other embodiment multiple prisms can be used which can use a corrective optical element to eliminate any deviation or aberrations in the see-though viewing path, such that a user of the device can comfortably see through the eye-tracker normally. For example, in one of it aspects, the invention may include a wedge prism having only planar surfaces. This prism acts as a light guide to supply illumination light to the eye, as well as providing imaging light to the camera from the illuminated eye. In this embodiment a complementary prism can be arranged with respect to the thin prism such that the two prisms appear to the eye as a plane-parallel plate, or as a weakly powered optic.

In an alternative embodiment, an eye-tracker can use a free-form prism between the eye and a sensor. The freeform prism includes one or more surfaces with optical power, which are used both for imaging of the eye onto the sensor, and for optical aberration control.

In certain embodiments, the freeform prism is used in conjunction with, or exclusive of, additional focusing optics such as a camera outside of the prism.

The eye-imaging camera can be mounted on the arm of an eyeglass frame or on the framework around the lens and can capture the image of the eye through reflection off of the lens. In order to properly capture the eye image through reflection off of lens, there must be sufficient clearance between the user's face and the lens surface to avoid the obstruction of the eye image by user's face or the imaging optics.

Alternatively, the camera can be mounted on the glass frame under or over the eye, and directly image the eye. This requires a more robust frame design, which must move the camera far enough away from the face to avoid interference. In this system, the camera captures an eye image at a close distance and from a slanted direction (i.e., at an angle), which results the eye image suffering keystone distortion. This arrangement also presents optical performance challenges due to the large depth of field necessary to accommodate all possible eye positions.

A beam splitter in an eyeglass lens can be used, off of which an eye is imaged by a camera positioned out of a user's line of sight. A beam splitter is an optical device that separates a beam of light into two or more different beams of light. Beam splitters are available in various forms. These include cubes, pipes and plates. What happens with a beam splitter is that it accepts the input beam and then proceeds to divide the light depending on the specified requirements. The input beam could be polarized or non-polarized light. The most commonly used is the cube beam splitter although the plate beam splitter is typically used to produce lower cost non-polarized beam splitters. These typically provide a 50-50% split ratio. The reflected and transmitted light emerging from the beam splitters are at various angles, which often necessitates external mirrors to redirect the light. Embodiments of the present invention are directed to single prism beam splitters and compound beam splitters formed from combining one or more of the single prism beam splitters. The beam splitters can be configured to produce one or more split beams of light that emerge from the prism at angles other than 90° to one another. The prisms can be configured so that the light propagating through the prisms encounters one or more intermediate planar surfaces at various angles with respect to the path of the light. A certain number of the intermediate planar surfaces can be angled so that the light transmitted along a particular path undergoes total internal reflection (TIR) at these intermediate planar surfaces. A number of other intermediate planar surfaces can be positioned or angled so that the light transmitted along a particular path does not undergo TIR. As a result, one or more beams of light propagating through the prism can be selectively split off to emerge from the prism by selectively disposing fully reflective and partial mirrors on the intermediate planar surfaces where TIR does not take place. The coating layer of a beam splitter can be made in such a way that a percentage of the light entering the beam splitter through one side can be reflected while another percentage is transmitted.

In other embodiments of the present invention, two or more of the single prism beam splitters can be combined to form compound beam splitters that split a single beam of light into three or more different beams of light. A beam splitter can have an optical multi-layer thin film, formed by laminating numerous layers in sequence. The numerous laminated layers can each be comprised of having a different refractive index.

In another embodiment, the eye tracking system can include a camera visor that is positioned in front of the eye of a user. In another embodiment, an array of optical detection elements can be placed directly onto the surface of the eyeglass-like lens located in front of an eye.

When using an eye-tracking camera, two general types of eye tracking techniques can be used: Bright Pupil and Dark Pupil. The difference between these eye-tracking techniques is based on the location of the illumination source with respect to the optics. If the illumination is coaxial with the optical path, then the eye acts as a retro-reflector as the light reflects off the retina creating a bright pupil effect similar to red eye. If the illumination source is offset from the optical path, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. But bright pupil techniques are not effective for tracking outdoors as extraneous IR sources interfere with monitoring. In embodiments of the present invention, eye tracking might typically use a sampling rate minimally of 20 Hz. Typical sampling frequencies can include 20/30/50/60 Hz, 240 Hz, 350 Hz, and 1000/1250 Hz. The higher sampling frequencies are needed to capture the detail of the very rapid eye movement during reading, or during studies of neurology.

Embodiments of the eye tracking system can track on the cornea or further in the eye, based on using light reflected by the eye. Whether using an external source or ambient light, some of the techniques for tracking the eye include: limbus tracking, pupil tracking, Purkinje image tracking, corneal and pupil reflection relationship, corneal reflection and eye image using an artificial neural network.

Regarding limbus tracking, the limbus is the boundary between the white sclera and the dark iris of the eye. Because the sclera is (normally) white and the iris is darker, this boundary can easily be optically detected and tracked. The limbus tracking technique is based on the position and shape of the limbus relative to the head. This means that either the head must be held still or the apparatus must be fixed to the user's head. Due to the occasional covering of the top and bottom of the limbus by the eyelids, it is more helpful for precise horizontal tracking only.

Regarding pupil tracking, this technique is similar to limbus tracking. The difference is that in pupil tracking the smaller boundary between the pupil and the iris is used instead of the boundary between the white sclera and the dark iris. Once again, the apparatus must be held completely still in relation to the head. The advantages of this technique over limbus tracking is that the pupil is far less covered by the eyelids than the limbus, and thus vertical tracking can be accomplished in more cases. Also, the border of the pupil is often sharper than that of the limbus, which yields a higher resolution. The disadvantage pupil tracking is that the difference in contrast is lower between the pupil and iris than between the iris and sclera, thus making border detection more difficult.

Regarding Purkinje image tracking, when (infrared) light is shone into the user's eye, several reflections occur on the boundaries of the lens and cornea. These reflections are called Purkinje images. The first Purkinje image is also called the glint, and this together with the reflection of light off the retina, the so-called bright-eye, can be video-recorded using an infrared sensitive camera as a very bright spot and a less bright disc, respectively. When the eye is panned horizontally or vertically, the relative positioning of the glint and the center of the bright-eye change accordingly, and the direction of gaze can be calculated from these relative positions. The problems associated with this technique are primarily those of getting a good view of the eye; lateral head movement can put the video image of the eye out of focus, or even make the image of the eye fall out of view of the camera. Due to the lack of contrast, the center of the iris can be tracked instead of the center of the pupil Regarding pupil and pupil reflection relationship tracking, eye trackers can combine a camera with an infra-red light source that illuminates the eye with bursts of invisible infra-red light. Some of this infra-red light disappears into the pupil (the dark opening in the center of the iris), and some of it bounces back off the iris (the colored part of the eye), the cornea (the clear part at the front of the eye), the eyelid or the surrounding skin. All these different areas reflect different amounts of infra-red light, which is picked up by the camera. By analyzing the reflections using "a lot of very fancy matrix math" it is then possible to work out where the eye is pointing. Because eyes move in tandem, this only needs to be done for one eye. The technique is able to cope with blinking, head movements, dim light, glasses and contact lenses.

Regarding the use of artificial neural networks (ANNs) for computation, this is of the more recently developed techniques. The raw material for eye-gaze tracking is still a digitized video image of the user, but this technique is based on a more wide-angled image of the user, so that the entire head is in the field of view of the camera. A stationary light is placed in front of the user, and the system starts by finding the right eye of the user by searching the video image for the reflection of this light-the glint, distinguished by being a small, very bright point surrounded by a darker region. It then extracts a smaller, rectangular part of the video image (typically only 40 by 15 pixels) centered at the glint, and feeds this to an ANN. The output of the ANN is a set of display coordinates. The ANN requires more than the simple calibration that is required by the other techniques; it must be trained by gathering images of the user's eye and head for at least three minutes while the user visually tracks a moving cursor on the display. This is followed by an automatic training session that uses the stored images lasting approximately 30 minutes using the current technology, but then the system should not require re-calibration on the next encounter. To improve the accuracy of an ANN-based system, the corneal/pupil based calculations can be augmented with a calculation based on the position of the glint in the eye socket. The great advantage of ANN-based techniques is that due to the wide angle of the base image, user head mobility is increased.

Eye movement information from the eye tracker can be typically divided into fixations and saccades, when the eye gaze pauses in a certain position, and when it moves to another position, respectively. The resulting series of fixations and saccades can be called a called a scan path. Most information from the eye can be made available during a fixation, but not during a saccade. The central one or two degrees of the visual angle (the fovea) can provide the bulk of visual information; the input from larger eccentricities (the periphery) is typically less informative and analysis algorithms can be structured accordingly. Hence, the locations of fixations along a scan path show what information loci on the stimulus are processed during an eye tracking session.

Scan paths are useful for analyzing cognitive intent, interest, and salience. Other biological factors (some as simple as gender) may affect the scan path as well. As a participant looks at a page on the internet, the eye-tracking device can focus on the pupil of the participant's eye and determine the direction and concentration of the participant's gaze. Heat maps represent where the visitor concentrated their gaze and how long they gazed at a given point. Generally, a color scale moving from blue to red indicates the duration of focus. Thus, a red spot over an area of your page might indicate that a participant, or group of participants, focused on this part of a page for a longer time. Saccade pathways trace the eye's movement between areas of focus. The movement is not unlike watching a hummingbird move between flowers—there are periods of attention and then rapid movement. A red circle may indicate the area of focus, while a red line indicates the flight.

Another capability of the eye tracking technology is eye movement analysis, which can provide valuable insight into users' overt visual behavior and attention. The most common method for determining the location of a user's observable visual attention is by identifying the fixations and saccades that best indicate where they are focusing on the stimulus in front of them.

A linear filter may be used when processing eye-tracking data to approximate eye movement signals, at least well enough to recognize a pattern. The salient eye movements that are typically identified by eye movement analysis are fixations, saccades, and smooth pursuits. Fixations are a result of one's desire to maintain gaze on a specific, stationary object. Smooth pursuits are similar except for the object of interest is in motion. Saccades represent a voluntary shift of focus from one fixation point to another.

Saccades can be detected and measured by two means as well: the position variance method and the velocity detection method. The position variance method identifies saccades as those moments in the signal in which the position of the eye changes rapidly. The velocity detection method uses an empirically determined velocity threshold. If the velocity of the signal is calculated as higher than the threshold, it is a saccade. Similarly, if it is below the threshold (as discussed above) it is a fixation. For both fixations and saccades, the velocity method is becoming more widely used because it is more suitable for real-time applications.

Beyond the analysis of visual attention, eye data can be examined to measure the cognitive state and workload of a person. Some techniques have been validated in multiple contexts as a reliable indicator of mental effort. Driving a car, reading a magazine, surfing the interne, searching the aisles of a grocery store, playing a video game, watching a movie or looking at pictures on your mobile device are such applications of eye tracking. With very few exceptions, anything with a visual component can be eye tracked. People use their eyes almost constantly, and understanding how the eyes are used has become an extremely important consideration.

In another embodiment, the use of sensors on a contact lens can also be used for eye tracking eye responses and specifically VOP measurement. Employing multiple sensors on a contact lens can be used for detecting eye movement and contact lens orientation. The contact lenses may also employ the use of markers or the lenses could be magnetized. A multi-sensor contact lens can be placed in one or both eyes of a user and can actively determine movement activities of the eye. These sensors can be located on the surface of the lens or within the lens material. In another embodiment, an eye blink for a defined time can trigger the measurement of eye movement or turn on the device to begin the calibration for measurement. It is to be appreciated that both eyes of a human user generally blink at the same time, and thus in various embodiments only one multi-sensor contact lens is needed to generate a command to a remote device. Components on or within a contact lens can be of a shape, size, opacity, and/or positioned so as not to obstruct vision through an opening of a pupil of an eye when worn. Control features of multi-sensor contact lens can include issuing commands, adjusting content presentation, activating or deactivating options or components, or any other suitable functions. The multi-sensor contact lens can include either on or within its substrate a control circuit that can be coupled wirelessly to the multiple sensors.

In another embodiment, the multi-sensor contact lens can also communicate via a wireless network to a remote device. The remote portable smart device can include a wearable device, such as a head worn device or smart watch, or a non-wearable device, such as a remote mobile computer device, like that of a mobile smart phone, smart pad, pc and the like. The multi-sensor contact lens can use various kinds of sensors and they can be integrated in various combinations. The power component can include any suitable power source that can manage, receive, generate, store, and/or distribute necessary electrical power for the operation of various components of multi-sensor contact lenses. For example, the power component can include but is not limited to a battery, a capacitor, a solar power source, radio frequency power source, electrochemical power source, temperature power source, or mechanically derived power source (e.g., MEMS system). In another example, the power component receives or generates power from one or more of the sensors. A transceiver can transmit and receive information to and from, or within multi-sensor contact lens. In some embodiments, the transceiver can include an RF (radio frequency) antenna. In further embodiments, the video eye camera/eye tracker can be controlled remotely and/or alternatively with eye movements or voice activation or haptically.

In embodiments of the present invention, saccades can be tested by positioning two widely spaced targets in front of the person and asking the person to look back and forth between the targets. The technology in an AR/VR platform can be used to calculate corrective saccades. This system for the person is configured to collect eye images of the person in excess of 60 Hz and configured to resolve eye movements smaller than at least 3 degrees of motion. Eye movement data can include at least one fixation target presented to the subject in a defined position and configured to yield a voluntary saccadic eye response from at least one eye of the person. The latency, amplitude, accuracy and velocity of each respective corrective saccade and latency totals and accuracy is calculated. This platform can calculate, and display secondary, and higher, corrective saccades. Calculating corrective saccade measurements from the eye data can include:

(a) the total number of corrective saccades associated with the subject's eye movement to each fixation;
(b) first corrective saccade latency;
(c) first corrective saccade amplitude;
(d) first corrective saccade accuracy;
(e) first corrective saccade velocity;
(f) ratio of first corrective saccade amplitude to main saccade amplitude associated with the subject's eye movement to each fixation target; and
(g) ratio of total of corrective saccade amplitudes to main saccade amplitude associated with the subject's eye movement to each fixation target presented to the subject.

The corrective saccade measurements can include measurements for a first corrective saccade and at least a second corrective saccade. The corrective saccade measurements for each corrective saccade can include the latency, amplitude, accuracy and velocity of each respective corrective saccade. During the initiation of a saccade, a high frame rate may be required to anticipate the landing zone of a saccade. This can be used, for example, to activate grammatical elements rapidly (i.e., without the need to even perceive the target element) and/or remove a target element from the display in order to eliminate corrective saccades and/or allow a new target to be chosen more rapidly using the so-called "gap effect."

Virtually, dynamic visual acuity (DVA), and retinal image stability (RIS), and foveal visual stability (FVS) testing can be used to determine the condition of a person's vestibulo-ocular reflex function. A DVA assessment can also include identifying a series of images or optotypes but with the addition of a head movement along an axis at a minimum rotational rate, engaging the vestibular system. The displayed images may also be dynamically moving in any direction, and can be random in position, appearance and presentation. Specifically, the image or visual element to be identified can be seen coming from any direction, randomly or with a specified pattern of motion, and may have different shapes, features, colors, sizes, orientation, patterns, or identifying characteristics, in a specific plane of axis or in variable plane, which the person must identify while the head in motion or rotating. The person can then provide feedback regarding what they see via an on-screen gesture, keyboard, smart device (e.g. defined as an electronic device, generally connected to other devices or networks via different wireless protocols such as Bluetooth, NFC, Wi-Fi, 3G, etc., that can operate to some extent interactively and autonomously), eye or other physical response or by voice response. The comparison of the smallest image, visual image or optotypes correctly identified or the comparison of the correct numbers of images, visual elements or optotypes in both the DVA and SVA tests can determine if the person has a defect in his or her vestibulo-ocular reflex functions.

In embodiments of the present invention, VR or AR platforms can have the unique advantage of measuring smooth pursuit in any plane and in a variety of scan paths. As an example, eye tracking and visual or smooth pursuit can be done by visually observing a moving image traditionally in a horizontal or vertical plane or alternatively in a saw-tooth, sinusoidal, square-wave, snake-like, torsional, looped or other non-fixed plane of motion, which is more natural to what the normal person experiences in everyday life. Convergence movements can be evaluated by having the person fixate on an object as it is moved slowly towards a point right between the person's eyes. In addition, the eyes can be observed and measured at rest to see if there are any abnormalities such as spontaneous nystagmus, dysconjugate gaze (eyes not both fixated on the same point) or skew deviation (eyes move upward (hypertropia), but in opposite directions, all resulting in diplopia (double vision). All of these evaluations can be measured with VR or AR platforms In embodiments of the present invention, pupillometry tests can easily be observed in either a VR or AR system, as the pupil can be measured on each side with variation of the levels of light. Both eye movement and peripheral vision testing can easily be measured in VR or AR systems. Eye movement testing can also be called extra-ocular muscle function testing is an examination of the function of the eye muscles. These tests observe the movement of the eyes in six specific directions. Peripheral vision testing is also called visual field testing. Testing the visual fields consists of confrontation field testing, in which each eye is tested separately to assess the extent of the peripheral field. Target detail within the peripheral field-of-view can be altered without attracting attention. In a process known as "change blindness," it is also difficult to discern visual changes (that attract attention) if the changes are introduced slowly or at times when an observer is not looking.

In embodiments of the present invention, the VR/AR system can be configured to:

(a) collect eye images in excess of 60 Hz;
(b) resolve eye movements smaller than at least 3 degrees of motion;
(c) measure when a stimulus is presented to only one eye of the subject or both eyes;
(d) yield a pupil eye response from at least one eye of the person;
(e) measure pupils in each eye independently for the person's left and right eyes; and
(f) compare pupillometry measurements for the left and right eyes.

Another embodiment involves dynamic control of the frame rate (i.e., number of images acquired per unit of time) of the one or more cameras that view regions of one or both eyes. Camera frame rate is a major determinant of the ability to determine and measure rates and directions of movement (i.e., velocities) of objects within images of an eye. The muscles within the eye are capable of movements that are the most rapid of all muscles within the human body. Thus, increased camera frame rate can be critical in some cases to more accurately and robustly measure dynamic movements of an eye and/or its components. Modern cameras are capable of operating over a wide range of frame rates. Instantaneous frame rates can also be adjusted (i.e., governed by so-called "clock" circuitry) as frequently as on an image-by-image basis. Closely aligned with camera frame rate is the acquisition time required to collect each image. The maximum time a camera can take to acquire an image is the inverse of the frame rate (i.e., the total time of a frame=1/frame rate). However, modern-day digital cameras also have the ability to limit the time over which they detect photons during the image acquisition process. Limiting the time to acquire photons is known in the art as "electronic shuttering." Shuttering light (including infrared) collection times to very brief intervals (typically in the order of microseconds to milliseconds) "freezes" images, allowing a clearer view of moving objects since object edges are spread over fewer pixels. On the other hand, longer acquisition times allow the detection of more photons during each image, increasing the amplitude (i.e., intensity within each pixel) of camera images and generally increasing signal-to-noise ratios. Although micro-movements can be useful to infer some aspects of a user's state (see below), they can interfere with directional and distance measurements of smooth pursuit and voluntary saccades. Higher frame rates allow algorithmic approaches to compensate for micro-movements by removing oscillations/movements at such frequencies or other mathematical approaches such as averaging results. Brief acquisition times can also be used to reduce image blur associated with micro-movements. The key to accurately determining initial saccadic direction and speed is the acquisition of camera images at high frame rates (typically hundreds of frames per second). Several techniques are available to acquire a rapid sequence of images immediately following a saccadic launch: 1) Once a saccadic launch is detected when sampling at a lower frame rate, the camera is immediately switched to a higher frame rate. 2) Camera circuitry (only) can be constantly run at a high frame rate, storing images within a circular buffer. Not all images are transferred out of the camera buffer and processed during normal operations. When a saccade is detected, rapidly sampled images that had been stored in the camera buffer can be retrieved for processing. 3) Frame rate can be adjusted based on the "context" of eye signal control. High frame rates can be maintained throughout these sequences.

Using an AR or VR display, one or more alphanumeric characters, halos, cursors, arrows, or other symbols may be superimposed within the display onto or adjacent to a particular object. These superimposed images or visual elements may indicate a particular meaning to the device user and this meaning may be assigned to the object so that it can be included in the eye signal language (in the same general manner as virtual icons). As examples, a halo can be placed around a physical light switch such that it can be the object of an action (e.g., turn on) or the name of a person can be displayed adjacent to the person's (real) face, allowing text or mail to be sent to that person using the eye signal language. Target or visual element fixation and image gaze data may be used within a gaze-based user interface enabled by an interaction model used with augmented reality or virtual reality. Such a user interface may also be multimodal incorporating head movement, hand movement, voice, and other physical or measurable brain-generated signals.

In further embodiments, any one of the tests, images, or visual elements described can also be visualized in a wearable display that includes a substrate guided optical device, known as the light-guide optical element system. Such a display can be a three-dimensional display. The display can be made up of an array of many small curved mirrors. Light could be delivered to that array via optical fiber. Each of the tiny mirrors could reflect some of that light to create the light field for a particular point in 3-D space, as a waveguide reflector array projector. The array could be semi-transparent to allow a person to see the real world at the same time. Multiple layers of such tiny mirrors would allow the display to produce the illusion of virtual objects at different distances. Planar wave guides or layers can be stacked to create a multifocal display in which each 2D planar wave guide, layer, column or set provides optical paths independently of other 2D planar wave guides, layers, columns or sets, allowing each to provide a respective focal or depth plane in a 3D image. This can include a series of linear or rectangular cylindrical wave guides arranged in vertical (xy) columns to create a planar 2D wave guide. This can include multiple 2D planar wave guides, columns, layers or sets, each corresponding to a different virtual depth plane. In such an embodiment using a partially transparent wave guide reflector array projector apparatus, a multiple depth plane three dimensional (3D) display system can visually provide multiple virtual depth planes at respective radial focal distances to simulate a 4D light beam field. The array of curved micro-reflectors can be oriented and positioned to project virtual images or visual elements at specified radial distances. The curved micro-reflectors typically partially reflect and partially pass electromagnetic energy, for instance optical wavelengths of light. The micro-reflectors can have one or more surface curvatures, and the surface curvatures may vary in each wave guide layer and the array can convert an input light beam from beam splitters into a stack of two-dimensional projections of virtual depth planes that recreates a three-dimensional volume on a display.

Embodiments of the invention can use miniature video cameras. The image of the eye can be tracked and allow the person's horizontal, vertical, and/or torsional (rotary) vestibulo-ocular responses to be measured. A moving visual target or visual element can provide a method for tracking, for optokinetic (OPK) testing, for saccade detection and measurement, for gaze fixation testing, for DVA measurement and for VOR testing. In the traditional Active Head Rotation (AHR) horizontal test, the subject moves their head left and right randomly to the auditory signal and visual presentation. The speed of the signals increases through 1 Hz up to a maximum of at least 5 Hz. The person will attempt to keep moving the head back and forth at the speed of the beeps. For AHR Vertical, this test is conducted in the same manner as the horizontal test above, except that the head motion is up and down rather than left and right In further embodiments, the VR/AR system can include a head mounted system with at least one, and typically two, digital camera(s) trained on the person's eyes and which the camera1 can have auto-tracking. Each camera can be connected to and/or powered by a computer, such as through a "firewire" type connection. The computer may be a laptop portable computer or other digital device. The digital cameras may allow for digital centering of the person's pupil at least in one direction through concentrating on the region of interest, and can be in multiple directions. The use of digital centering eliminates the need for a mechanical adjustment mechanism in the given direction.

In another embodiment, the eye sensor can be further configured to capture a 3D image of the iris. In another embodiment, the eye sensor can be comprised of an array of transparent light detectors based on graphene. In another embodiment, the system can include an illuminator that is configured to provide illumination in a visible, LED or infrared light spectral band for the eye sensor to capture the 3D image of the iris. In further embodiments, the eye sensor can be a microlens array light field camera (LFC) or plenoptic camera. Holograms can be used to blend the digital world with the real world in the AR systems (to aid in the testing and measurement of the eye movement, acquire more immersive ways to be engaged in activity desired, and provide ways to teach, train, learn, explore, collaborate and create). This can enable a more immersive see-through multi-dimensional method for all of the visual or oculomotor tests described in this disclosure.

Embodiments of the present invention can comprise existing wearable display devices such as: (a) the VR devices manufactured by Sony, Samsung, Oculus, Carl Zeiss; (b) head mounted displays (HMDs) such as those produced by Google (e.g., Google Glass®) and Vuzix; and (c) augmented reality (AR) displays such as those manufactured by Microsoft, Vuzix, and DigiLens. Eye tracking sensors, such as digital video cameras, can be used to view such displays and to determine eye position information. Head tracking accelerometers are already commonly embedded within wearable devices of the type described herein. Acceleration and orientation relative to the earth's gravitational field based on the output of a head-mounted multi-axial accelerometer can provide information about relative head movements. When coupled with eye gaze direction and the tracking of vestibulo-ocular eye movements, absolute head position and movements referenced to viewed objects can be discerned. Within a wearable display system object position, direction, distance, speed and acceleration can be plotted. These display devices, with eye and head tracking sensors, provide a method to integrate head gestures with eye-signal control.

In embodiments of the present invention, eye movements, responses or reflexes and head movements can be detected and measured in a manner using VR and/or AR platforms, that are novel and unique compared to what has been done traditionally in the clinical laboratory. These embodiments enable a higher level of testing and measurement for these eye responses, particularly for the VOR and DVA. Embodiments of the present invention also provide unique methods to rehabilitate persons with vestibular system disorders, particularly those with peripheral vestibular disorders and especially those persons with vestibulo-ocular reflex abnormalities and/or abnormalities of the dynamic visual acuity.

In another embodiment, the images or visual elements presented for VOP tests (which can include DVA or other oculomotor measurements) can correspond to a plurality of depth planes provided to a viewer in the VR or AR display. The target image or visualized element may be different for each depth plane, which can provide a slightly different presentation of a scene or object. The target or visual element may be separately focused by each of the viewer's eyes, to provide depth cues based on the accommodation of the eye required to bring into focus different image features for the scene located on different depth plane and/or based on observing different image features on different depth planes being out of focus. These depth cues can provide credible perceptions of depth and add complexity to the testing and measurement.

4. Image Projection

Eye tracking, video recording, and specifically VOP measurement can be performed using a virtual retinal display or holograph imaging in another embodiment. A virtual retinal display (VRD), also known as a retinal scan display (RSD) or retinal projector (RP), is a display technology that draws a raster display, or bitmap, directly onto the retina of the eye. The user sees what appears to be a conventional display floating in space in front of them. However, the portion of the visual area where imagery appears must still intersect with optical elements of the display system. It is not possible to display an image over a solid angle from a point source unless the projection system can bypass the lenses within the eye. In a conventional display a real image is produced. The real image is either viewed directly or, as in the case with most head-mounted displays, projected through an optical system and the resulting virtual image or visual element is viewed. The projection moves the virtual image or visual element to a distance that allows the eye to focus comfortably. No real image is ever produced with the VRD. Rather, an image is formed directly on the retina of the user's eye. Eye movement and head inertial tracking can be measured while being connected to a virtual display system. The measurements can also be triggered with an external "microcontroller". Not only can VOR testing and DVA measurement be done with the virtual display, but it can also be used for other "immersive testing", sport training, military training, commercial medical education or teaching.

Therefore, in an alternate embodiment, the camera can track the eye movement and measure the VOR using holographs or augmented reality display imaging.

Although the VRD is an output device, the technology lends itself to augmentation with eye tracking or eye gaze systems for input. The VRD system scanning light into only one eye allows images to be laid over one's view of real objects. The VRD system also can show an image in each eye with an enough angle difference to simulate three-dimensional scenes with high fidelity. The eye tracking can enable the fovea on the retina to always maintain good focus ability and as the pupil changes position, eye tracking with movement of the eye follows. As the eyes move, the foveation point can also change to achieve better tracking. Using a refractive lens can be used to prevent distortion of eye tracking. The fovea centralis, also generally known as the fovea is a part of the eye, located in the center of the macula region of the retina. The fovea is responsible for sharp central vision (also called foveal vision), which is necessary in humans for activities where visual detail is of primary importance.

In another embodiment low-persistence-of-vision display can enable a user to see images at only 24 frames per second. Even though the images flash by one by one, the mind fill in the blanks and the user will see (relatively) smooth motion. By reducing the amount of information the user sees, the brain can smooth out virtual reality. A head attached tracker (also known as an orientation sensor), with an adjustable sample rate, but minimally 20 Hz, and with tracker latency can be used to enhance virtual reality's realism on response time. Using a combination of 3-axis gyros, accelerometers, and magnetometers, can make it capable of absolute (relative to earth) head orientation tracking without drift. Each display to the eye can be adjusted with interchangeable lenses that allow for dioptric correction and adjustments for inter-pupillary distance requirements can be done. The mounted head tracker, when used with the eye worn virtual display can move the images to match the user's head movements, and create a greater sense of being inside a high definition LCD, LED or 1080p OLED 3D (3 dimensional) images being displayed. A wireless interface can be used for sending the collected tracking data to a remote device. Hand held micro-controllers can also be used to manipulate the displayed images and obtain more of an immersive testing, training or rehabilitation experience.

In another embodiment, a different medium platform can be used to project the visual data for measurement of VOP, using a 3D (3 dimensional) virtual retinal display. In this embodiment, the virtual projection imaging device has no screen but can project images directly to the user's eyes. This screen-less display with the image displayed directly to the retina can also use a multiple micro-mirror design and low power light source. The image display quality can display a separate WXGA resolution (1,280×768) image directly onto the retina of each eye. The displayed images can be generated with reflected rather than emitted light. While LCD and OLED panels are emissive light, this display can project reflective light directly into the eye and mimicking more natural vision. The resolution and frame rate (minimally 240 frames/sec) can be high. Each eye can be focused independently focus and adjustments can be made to acquire a single image when wearing the device. Head inertial tracking and eye tracking can be incorporated in the head worn device. Two discrete images can be projected directly onto the retinas of the user and the optical elements can be individually adjusted.

To create an image with the VRD a photon source (or three sources in the case of a color display) can also be used to generate a coherent beam of light. The use of a coherent source (such as a laser diode) can allow the system to draw a diffraction-limited spot on the retina. The light beam can be intensity modulated to match the intensity of the image being rendered. The modulation can be accomplished after the beam is generated. If the source has enough modulation bandwidth, as in the case of a laser diode, the source can be modulated directly.

The resulting modulated beam is then scanned to place each image point, or pixel, at the proper position on the retina. Varieties of scan patterns are possible. The scanner could be used in a calligraphic (vector) mode, in which the lines that form the image are drawn directly, or in a raster mode, much like standard computer monitors or television. Use of the raster method of image scanning allows the VRD to be driven by standard video sources. To draw the raster, a horizontal scanner moves the beam to draw a row of pixels. The vertical scanner then moves the beam to the next line where another row of pixels is drawn.

After scanning, the optical beam must be properly projected into the eye. The goal is for the exit pupil of the VRD to be coplanar with the entrance pupil of the eye. The lens and cornea of the eye will then focus the beam on the retina, forming a spot. The position on the retina where the eye focuses the spot is determined by the angle at which light enters the eye. This angle is determined by the scanners and is continually varying in a raster pattern. The brightness of the focused spot is determined by the intensity modulation of the light beam. The intensity modulated moving spot, focused through the eye, draws an image on the retina. The eye's persistence allows the image to appear continuous and stable. Finally, the drive electronics synchronize the scanners and intensity modulator with the incoming video signal in such a manner that a stable image is formed.

Liquid crystal displays (LCDs) currently are often used in display devices for the presentation of information. LCDs with a display resolution of 1080p HD or greater can provide the image quality that is best for VR or AR systems. An image that is generated electronically is viewed with the optical system of the eye. The image seen is subject not only to the quality of the optical system of the eye, but also to the quality of the display and the environment in which the display is located.

With a VRD, defects in the eye's optical system, such as damaged cornea and lens and reduced retinal sensitivity could be bypassed, as well as the problems of the display environment, such as ambient brightness, angle-of-view and display brightness. Additionally, the seen image could be augmented with other information and brightness of the system does not affect the image formed on the retina. It is believed that VRD based Laser or LED displays are not harmful to the human eye, as they are of a far lower intensity than those that are deemed hazardous to vision, the beam is spread over a greater surface area, and does not rest on a single point for an extended time. Optical damage caused by lasers comes from its tendency to concentrate its power in a very narrow area. This problem is overcome in VRD systems as they are scanned, constantly shifting from point to point with the beams focus. If the laser stops scanning, beam stays focused on one spot can cause permanent damage to the eye. This can be prevented by an emergency safety system to detect the situation and shut it off. Apart from the advantages mentioned before, the VRD system scanning light into only one eye allows images to be laid over one's view of real objects. For example, it could project an animated, X-ray-like image of a car's engine or the human body.

VRD system also can show an image in each eye with an enough angle difference to simulate three-dimensional scenes with high fidelity. VRD can refocus dynamically to simulate near and distant objects with a far superior level of realism. VRD also supports proximity sensing.

This means it can provide the illusion of being able to actually be more closely involved with the projected images.

In another embodiment a virtual image projector can also be comprised of a laser configured to form a narrow beam, multiple other optics, and a controller. The multiple optics each have a diffraction grating. One optic can be arranged to receive the narrow laser beam and to project a one-dimensionally dilated beam into the second optic. The second dilation optic can be arranged to receive the one-dimensionally dilated beam and to project a two-dimensionally dilated beam, which the can provide a virtual image. The first and second redirection optics are each operatively coupled to a transducer. The video-display eyewear can resemble eyeglasses and can include a pair of projectors that project virtual display images for view by a wearer. The virtual display images are projected directly in front of the wearer's eyes. The device can include a wearable mount configured to position the projectors a short distance in front of the wearer's eyes. The device can also include controller, which controls the internal componentry of the projectors in order to form the virtual display. Projectors may project virtual display images of infinitely distant objects, where the lens of the human eye adjusts to an infinite or near-infinite focal length to focus on such objects. The projectors may be at least partly transparent, so that the wearer can see external objects as well as the virtual display images or visual elements. The glasses include lenses arranged in front of the projectors and they can be arranged in front of the projectors. The lenses may be configured to correct the focus and/or brightness of the external objects for the comfort and vision needs of the wearer. This arrangement may allow the wearer to shift his or her focus between the external objects, a finite distance away, and virtual display images an infinite distance away.

In an alternative embodiment, the controller can cause projectors to project the same virtual display image concurrently, so that the wearer's right and left eyes receive the same image at the same time. In another embodiment, the projectors may project slightly different images concurrently, so that the wearer perceives a 3 D stereoscopic image.

In another embodiment, eye movement is measured without a camera system and utilizes electrodes placed on the surface of the skin around the eye(s). It is based on the principal where the eye acts like a battery: the cornea is the positive pole and the retina is the negative pole. Electrodes located in specific peri-orbital areas (e.g. around the eye) pick up the corneal-retinal electrical potential variation caused by eye movements, which are then amplified and sent to a recording device. Two (2) or three (3) channel recording devices can be used to record all eye movements. An active electrode is placed next to the external corner of each eye and the third electrode is placed on the frontal midline in such a way that the three recording channels are configured as an isosceles triangle. Three bipolar derivations are set from the active electrodes, thereby making it possible to identify horizontal, vertical and oblique eye movements. Measuring the slow component velocity of nystagmus takes into account the directional influence of responses according to the vector projection of eye movements.

5. Head Tracking

Head tracking on a head-worn unit can be performed by using an inertial measurement unit (also called an IMU or 'tracker'). An IMU is an electronic device that measures one or more DOF (such as position, velocity, orientation, and/or gravitational force, as was described previously in this disclosure) by using one or more sensors. Sensors used in IMUs can include one or more accelerometers, gyroscopes, and magnetometers. A MEMS (micro electro mechanical system) gyroscope, a MEMS accelerometer, and a MEMS magnetometer can be used as complementary and/or redundant sensors to accurately support a full range of motion in a three-dimensional space. Accelerometers work well for measuring five DOF: linear movements in three axes; and absolute tilt about the two axes perpendicular to gravity (i.e. pitch and roll). Accelerometers cannot easily measure rotation about an axis aligned with gravity (i.e. yaw). Magnetometers work well for measuring absolute yaw providing a sixth DOF. Gyroscopes provide a stable way to measure changes the three rotational DOF (pitch, roll, and yaw). Devices that measure these three displacements and measure each of the three rotations in two different ways are typically called nine DOF IMUs. The input signals from the accelerometer(s), magnetometer(s), and gyroscope(s) in these nine DOF IMUs are often processed using a Kalman or a Madgwick filter located in a sensor pre-processing unit to provide output signals that have been optimized for accuracy, stability, and response rate.

The head tracking inertial system can be mounted to the head in numerous configurations. Examples include: at the top of the head with helmets, caps, straps or other head worn covering; in the center of eyeglasses; at the nose piece; in the side of the eyeglasses; in the ear or attached to the ear; and/or attached to the teeth with mouth guards, prosthetic attachments, or fixation with other oral appliances. In other embodiments, the head tracking can be done from sensors in a hand held smart phone, smart pad, or other sensor system attached to a body part. When used in VR and AR platforms, the head tracking technology can normally refresh on-screen images 125-1250 frames per second (or Hz). Higher frame rates reduce movement lag. For specific applications, the refresh rate may be lower than 125 frames per second (fps) or higher than 250 (fps), depending upon the platform used, the application, and type of measurement or testing being performed. For performing some tests, such as the head impulse test a sample rate or refresh rate of 250 Hz is necessary to capture the subtle eye movements, such as the covert saccades. Reducing the lag between head movement and the headset response will mitigate symptoms of motion sickness or visually induced motion sickness. The resolution use can be variable depending on the application or platform used, but may be chosen as 1080×1200 or 2160×1200–2560×1440 or higher and the latency between images should be short (20 ms or less). In further embodiments, the head tracker can be controlled remotely and/or alternatively with eye movements, or voice activation or haptically.

6. Fourier Analysis

A Fourier transform can be used to convert the relationship between an input (such as head motion) and an output (such as eye movement) in the time domain to a relationship in the frequency domain. By doing this, VOP can be measured for natural motion in a non-clinical environment. As described previously, one of the traditional ways of measuring VOR has been to oscillate a subject's head at a fixed frequency and then to measure how quickly the eyes respond. For this kind of testing, a frequency of 0.5 Hertz would correspond to one cycle every 2 seconds. A cycle corresponds to the combination of one movement to the right and one movement to the left. These movements are typically in the form of a sine wave. The gain at this frequency would be the amount of compensation that the eyes make to the movement of the head. A gain of −1 (also often written as a gain of 1) is perfect because the eyes have rotated exactly the same angle as the head, but in the opposite direction. A gain of −0.75 (often written as 0.75) means that the eyes only compensated for 75% of the head rotation. The phase or phase lag describes how much later the eyes moved than the head. A phase or phase lag of 0 would mean the eyes followed exactly. A phase or phase lag of 45 degrees at a frequency of 0.5 Hertz means that the eyes were delayed by $\frac{1}{8}^{th}$ of 2 seconds (or 250 milliseconds) because 45 degrees corresponds to $\frac{1}{8}^{th}$ of a full 360-degree cycle. To determine gain and phase at a variety of frequencies using the traditional approach of oscillating the head in a clinical environment one would repeat the above test at a variety of frequencies and record the results. This method requires control over each input frequency and measuring the gain and phase of the eye response separately for each frequency, which will not work in a non-clinical setting having natural motion.

Any time-varying signal (such as the natural motion of an object in one dimension) can be converted to a series of sine waves. This conversion from a time-varying signal to a series of sine waves is called a Fourier transform. Fourier transforms can be discrete or continuous. A continuous Fourier transform is one in which the time-varying signal is converted to an entire range of frequencies with no gaps between the frequencies. A discrete Fourier transform is one in which the time-varying signal is converted to a specific set of frequencies, such as the series 0.125 Hz, 0.25 Hz, 0.5 Hz, 1.0 Hz, and 2.0 Hz. Discrete Fourier transforms are easier to calculate using digital electronics. By converting the observed natural yaw of the head as a function of time using a Fourier transform, one can generate a graph showing the amplitude of the input signal that the eyes would need to compensate for in order to follow a stationary image or visual element. By converting the sensed horizontal movement of the eyes at this same time using a Fourier transform, one can generate a second graph showing the amplitude of the eye signal that compensates for the head movement. By comparing these two graphs mathematically, it is possible to determine gain at various frequencies directly from the natural head yaw movement. Similar mathematical calculations can be made to determine phase. The same method can be used to determine gain and phase in other dimensions such as pitch of the head versus the sensed vertical movement of the eyes, etc. Discrete Fourier transform calculations of this type can be performed by a microprocessor that receives the time-varying orientation signals from a head orientation sensor and the time-varying signals from an eye orientation sensor using mathematical calculations capable of being understood by anyone skilled in the art.

7. Other Potential System Elements

An example of a portable and wearable computing and head mounted display system can include an eye tracking and measuring system, a connected head mounted display tracking and measuring system, an optical system, peripherals, a power supply, a micro-processor, a memory, and a user interface. Components of the system may be configured to work in an interconnected fashion with each other and/or with other components coupled to respective systems. For example, the power supply may provide power to all the components of the system. The processor may receive information from and control the eye tracking system; the head mounted tracking system, the optical system, and peripherals. The processor may be configured to execute program instructions stored in the memory unit and to generate a display of images on the user interface. The display to the user can be presented as a 2D or 3D (3 dimensional) virtual display.

The system may include or be coupled to peripherals, such as a wireless communication interface, a touchpad, an integrated microphone, a high definition (HD) camera, and a speaker. A wireless communication interface may use 3G cellular communications, such as CDMA, EVDO, GSM/GPRS, or 4G cellular communications, such as WiMAX or LTE. Alternatively, wireless communication interface may communicate with a wireless local area network (WLAN), for example, using Wi-Fi. In some examples, wireless communication interface may communicate directly with a device, for example, using an infrared link, Bluetooth, near field communication, or ZigBee. In addition, other wireless interface communication can be used with "off-the-grid" networks (such are FireChat) where there is not cellular phone service or no internet connection.

The power supply may provide power to various components in the system and may include, for example, a rechargeable lithium-ion battery, solar power, mechanical power or various other power supply materials and types known in the art.

The processor may execute instructions stored in a non-transitory computer readable medium, such as the memory, to control functions of the system. Thus, the processor in combination with instructions stored in the memory may function as a controller of the system. For example, the processor may control the wireless communication interface and various other components of the system. In other examples, the processor may include a plurality of computing devices that may serve to control individual components or subsystems of the system. The processor, in conjunction with the memory unit, may perform analysis of the images obtained by the infrared camera.

In addition, the memory unit may store data that may include a set of calibrated wearer eye pupil positions and a collection of past eye pupil positions. Thus, the memory may function as a database of information related to gaze direction. Calibrated wearer eye pupil positions may include, for instance, information regarding extents or range of an eye pupil movement (right/left and upwards/downwards), and relative position of eyes of the wearer with respect to the HMD. For example, a relative position of a center and corners of an HMD screen with respect to a gaze direction or a gaze angle of the eye pupil of the wearer may be stored. Also, locations or coordinates of starting and ending points, or waypoints, of a path of a moving object displayed on the HMD, or of a static path (e.g., semicircle, Z-shape etc.) may be stored on the memory unit.

The system may include the user interface for providing information to the wearer or receiving input from the wearer. The user interface may be associated with displayed images, a touchpad, a keypad, buttons, a microphone, and/or other peripheral input devices. The processor may control functions of the system based on input received through the user interface.

One or more of the described functions or components of the system may be divided up into additional functional or physical components, or combined into fewer functional or physical components. For example, the infrared camera may be mounted on the wearer separate from the system. Thus, the system may be part of a portable/wearable computing device in the form of separate devices that can be worn on or carried by the wearer. Separate components that make up the wearable computing device may be communicatively coupled in either a wired or a wireless fashion. In some further examples, additional functional and/or physical components may be added.

The system may be configured as, for example, eyeglasses, goggles, a helmet, a hat, a visor, a headband, or in some other form that can be supported on or from a head or parts of the head of the wearer. The system may be further configured to display images or visual elements to both eyes of the wearer. Alternatively, the system may display images or elements to only one eye, either a left eye or a right eye.

If used as part of a head mounted display (HMD), the system may include a gyroscope, a global positioning system (GPS), magnetometer, and an accelerometer. The head mounted display tracking system may be configured to provide information associated with a position and an orientation of the HMD to the processor. The gyroscope may include a micro-electromechanical system (MEMS) gyroscope or a fiber optic gyroscope as examples. The gyroscope may be configured to provide orientation information to the processor. The GPS unit can include a receiver that obtains clock and other signals from GPS satellites. The GPS unit can be configured to provide real-time location information to the processor. The HMD-tracking system may further include an accelerometer configured to provide motion input data to the processor.

8. Additional Embodiments

In one embodiment, the device or method uses utilizes eyewear with an eye-tracking and measuring sensor, a head motion sensor and compares the gain and phase of each (e.g. an electronic circuit generates a comparison of the three axes from the head orientation sensing element with eye movement signals from the eye sensor to calculate a gain and phase of the eye movement response to head rotation, in the opposite direction). The eye orientation sensor senses vertical movement and horizontal movement of at least one eye. A visual target is provided in the eye worn lens, which can be otherwise transparent, translucent or opaque. The device or method can present this visual target to one eye (monocular) or both eyes (binocular). The device or method is sufficiently comfortable, secure to the head and lightweight to allow the user to have active head movements while wearing the device. Wearing such a mobile or portable, head worn or eye worn device requires a power source. If the power source is in the head worn device of the eye tracker or head tracker it can be rechargeable by a wireless interface.

The device can measure the relationship between motion of the head in this environment and VOP. The data acquired can be uploaded to a remote position from the user for display and interpretation or transmitted wirelessly to a smart phone, wearable display device or other hand held device or other pc computer source. The eye tracker latency delay can be in the range 1 ms-10 ms and can have options to set the latency. The device can be charged with a wireless interface. The head orientation sensor does not use an external pulsed magnetic field and senses pitch and yaw of the person's head in a range of frequencies that comprises at least one frequency greater than 0.01 Hertz and less than 15 Hertz. The head orientation sensor can comprise an IMU. The head orientation sensor can comprise one or more accelerometer(s), magnetometer(s), and/or gyroscopes.

In one embodiment, a single camera system is used for the eye tracking. In another embodiment a multi-camera system is used and the cameras can be located in the lens, framework or eye or head worn device or located remotely. The camera control unit could be activated by touch, head movement, voice, a timer, an external wireless signal, or by placing the device on the head (e.g. putting on the head-worn unit). An eye blink, for a defined time, could also trigger the camera. An algorithm measuring blinking time and duration to discriminate between voluntary and involuntary eye blinks could be used to issue a command to a controller to operate the camera system. The controller could communicate with other parts of the system to support the commands. The camera could have a resolution of at least five megapixels and could be capable of recording at 720p or 1080p resolutions. The camera could have a microphone for voice commands, and at least 12 GB of usable storage. The camera could support Bluetooth and/or Wi-Fi. The camera could be part of, or work with an Android or iOS smartphone. The camera could have at least a 25° field of view. The camera system could also comprise an onboard OMAP (Open Multimedia Applications Platform) processor running the Android or iOS operating system. The entire system could be a smartphone that includes an embedded eye camera sensor with a head motion sensor. Providing direct image overlay over the wearer's main line-of-sight, coupled with the motion sensors and camera, it can enable true augmented reality capability. A smartphone or similar device (such as a tablet computer) could also be used to provide wireless remote control.

In one embodiment, the eye-tracker uses the center of the pupil and infrared and/or near-infrared non-collimated light to create corneal reflections (CR). The vector between the pupil center and the corneal reflections can be used to compute the point of regard on surface or the gaze direction.

In an alternative embodiment of a binocular system, two mirror-image optical systems are mounted on each side of the eyeglasses frame. The corneal reflections are generated by illumination with two infrared LED's mounted to the glasses frame. These LED's also serve to illuminate the pupil. The use of infrared (IR) light allows for invisible illumination of the eye. The use of multiple corneal reflections extends the linear range of the system by ensuring that one corneal reflection is always visible on the spherical surface of the cornea even with eccentric gaze. The images of the pupil and corneal reflections are reflected off of an IR mirror positioned in front of the subject's eye and directed to the cameras. This mirror is transparent to visible light and thus does not interfere with normal vision. The video image is sampled by a custom charge-coupled device (CCD) array that allows images to be sampled minimally at 20 Hz. Images from the CCD camera are processed in real time to obtain estimates of the corneal reflection and pupil center locations. Calibration of the eye tracker can be performed using a light source, such as a laser pointer, and calibration procedure looking at multiple objects or points (usually 5).

Another embodiment may use an OLED-based eyewear display which enables the eye tracking of a person with the use of an embedded IR display and camera in the see-through-lens of a head mounted/eye worn device. This can be worn as a monocular or binocular device with a transparent OLED display inside, which overlays digital information on top of the reflected light that strikes the eye. A bi-directional micro-display can be used in the head worn system for additional gaze triggered augmented-reality (AR) applications. The display contains both an active OLED matrix and integrated photodetectors that can track eye movement activity with front brightness up to 2000 cd/m$^2$.

Another embodiment can use a Liquid Crystal on Silicon (LCoS), field-sequential color, LED illuminated display. The display's LED illumination can be polarized and then shines through the in-coupling polarizing beam splitter (PBS) to the LCoS panel. The panel reflects the light and alters it to S-polarization at active pixel sites. The in-coupling PBS then reflects the S-polarized areas of light through the out-coupling beam splitter to a collimating reflector at the other end. Finally, the out-coupling beam reflects the collimated light into the wearer's eye.

In another embodiment, a low persistence OLED (Organic Light Emitting Diode) 1080p HD 3D (3 dimensional) virtual display can be utilized for VOP measurement. The OLED display may not be as bright as an LCD display, but it has a major advantage in delivering crisp, rapid movement without any smearing or ghosting of objects. Multiple separate cameras or a single large screen, which is split in half, can be used to provide two view points for each half of the screen. The two views can then be seen separately to either eye to with lenses in the head worn device, to provide a wider field of view. Orientation and movement can be tracked with the stereo 3D (3-dimensional) head tracker with 360 degrees. The user when being tested with the 3D (3-dimensional) virtual display has a sense of being "intimately around the points of visual focal interest". An additional embodiment of using a hand held controller can also be used to sense motion anteriorly and posteriorly, with a 3D (3-dimensional) hand held mobile controller. Testing of the VOR can also be tested with pitch and roll of the head tilt. Predictive tracking (e.g. algorithm which can predict the next head position and orientation can help computing and updating) can be used to prevent latency issues and lessen motion disturbances while being tested. A bone conducting sensor incorporated in the framework can provide auditory/acoustic signals to the user. This data can then be stored, logged, interpreted and uploaded to a remote location.

The eye tracking system can be used with or without a light source. Therefore, another embodiment of eye gaze tracking can be provided with magnetized contact lenses tracked by magnetic sensors mounted on the user's eyewear and/or reflectors or markers on the contact lenses tracked by video-based sensors, also mounted on the user's eyewear. Tracking information of contact lenses from magnetic sensors and video-based sensors may be used to improve eye tracking and/or combined with other sensor data to improve accuracy of eye tracking. Contact lenses may be tracked by one or more mounted head worn cameras and/or magnetic sensors in order to resolve tracking information, such as position of the objects, the distance between the objects and a camera, and the like. Furthermore, reflective contact lenses improve blink detection while eye gaze tracking is otherwise unimpeded by magnetized contact lenses. Additionally, contact lenses may be adapted for viewing 3D (3-dimensional) information. Alternatively, another method could be to place four evenly spaced sensors on the inside of the contact lens, so they cover every angle of the eye movement. The sensors could even be embedded in the lens itself.

In further embodiments, magnetic sensors and video-based sensors may be used in combination to track a magnetized contact lens with one or more reflective patterns, provide blink detection, and eye movement. Other video-based sensors may be used to locate the head position of a user and prune noise from other magnetic or other light sources. Additionally, tracking information from contact lenses of both eyes may be used to improve accuracy.

Magnetized and reflective contact lenses may be utilized to browse menus of computer applications, control virtual characters of video games, select-drag-manipulate objects, and perform other trained or learned actions responsive to a user's eye movement or eye gaze. In further aspects, magnetized and reflective contact lenses can be used in any application that can benefit from eye and/or gaze tracking.

In one embodiment, magnetic sensors may be placed on a video game console or near the head of a user of a video game console to track the location and polarization of magnetized contact lenses. In another embodiment, video-based sensors may be used to track the location of reflective contact lenses transparent to normal light and reflecting one or more portions of the electromagnetic spectrum.

Contact lenses in embodiments can be passive (e.g., utilizing color or polarity for 3D viewing) or active, for example, using a liquid crystal layer that is normally transparent but darkens when a voltage is applied.

One of the advantages of using contact lenses for eye tracking and viewing 3D (3 dimensional) information is that they are more practical (i.e., smaller, light weight and easy to carry around) compared to some peripherals used for eye gaze tracking or for 3D information viewing. For example, glasses typically used for 3D information viewing or head-mounts typically used for eye gaze tracking can be complex and cumbersome.

In addition, contact lenses can offer highly accurate eye tracking information at low cost. For example, when contact lenses are used for eye gaze tracking, the performance can be better than the one that can be achieved with a camera-based eye tracking solution. Also, compared to camera-based solutions which require expensive high-resolution cameras, contact lenses can offer low cost solutions which make them more suitable for consumer products.

Accordingly, in various embodiments, a combination of marker-based and marker-less eye tracking techniques using contact lenses provide interacting with or controlling objects or menus of a video game, a projected visual user interface, an augmented virtual reality user interface, or the like.

In another embodiment contact lenses with embedded electronics inside such as LEDs, LCDs. or new nano-electronic materials can also be used for eye tracking. Applications of electronic contact lenses may be even more promising.

Trackers can constantly ping the sensors in the IMU to get information from them. The rate at which this happens is expressed as [samples] Hz (per second). The wearer of a head tracker may perform a gesture to indicate an attempt to unlock the head mounted camera display. For example, a gyroscope coupled to the head mounted display may detect a head tilt, for example, and indicate that the wearer may be attempting to unlock the head mounted display screen.

In one embodiment the head tracker comprises an IMU, an RGB (Red Green Blue) LED, an 800-925 nm infrared LED, a battery and wireless interface charger, a wireless interfaced micro-controller, and a transceiver. The gyroscope in the IMU can be capable of sampling rates up to 760 Hz, and the transmitter link can have the throughput to transmit that fully under 1 ms latency to the remote station. Full positional updates (fused information from all the sensors) from the IMU can be sent at a rate of at least 500 Hz. The IMU comprises sensors that can sense roll, pitch, and yaw, as well as inertia when the IMU is moved forward/back, left/right, and up/down. The IMU could be a nine DOF IMU.

Another embodiment can use eyewear that has elements within the transparent, opaque or semi-transparent lens comprised of: calibration points, light source and video camera for recording any eye movement. In this embodiment, no mirrors are utilized. The framework provides the power source, data logging capacity, software for measurement and can include: alarm signal for movement of the head, sensors to transmit collected data to remote source and data interpretation. This can be done with passive head movements or active head movements and an alarm in the device can trigger the timing event of head movement, rather than having another person move the user's head for more of an "active head movement test". Specifically, the electronic circuit can be triggered or turned on by verbal command (auditory input), by visual means (such as prolonged eyelid closure or other specific eyelid movement), mechanically (such as by the attachment of the head worn device to the head), with timer software programming, and remotely. Additionally, this worn device can provide software to detect a value or abnormality for eye response or eye reflex, where eye response (or reflex) might be VOR, DVA, DVS, or RIS. This eye response (or reflex) output could be reported as a binary (normal or abnormal) value or it could be reported as a score on a continuous scale, such as the way in which other physiologic parameters (such as height, weight, blood pressure, temperature, and many more parameters) are reported. If a score is reported, it could be a score for a single parameter at a single frequency, such as gain or phase at 0.5 Hertz, or it could be a multi-frequency composite score (such as gain or phase or a combination of gain and phase at a range of frequencies from 0.1 Hertz to 1 Hertz). The score could be for one eye or both eyes. The score could include measurement of asymmetry.

An eye response (or reflex) score on a continuous scale or on a continuous composite scale (or a simple reporting of abnormalities), could then benefit from a rehabilitative VOR eye-tracking program. This can then enable the person to develop normal VOP again or enhanced eye fixation and specifically RIS on a target of interest with head rotation or head movement, or improve other ocular response or reflex capabilities while performing their occupational activities.

If the device does not need to be completely portable and self-contained, one can perform inertial head position and/or orientation tracking by transmitting external signals such as pulsed magnetic fields, optical signals, or audio signals to a transducer located on the head-mounted (eye-tracker) system. The transducer can be mounted on the eyewear/head for azimuth rotation. For example, a fixed transmitting device can radiate a pulsed magnetic field into which the head mounted receiver is immersed. The field is sensed by the receiver and processed by a microprocessor to provide three-dimensional position information as well as head elevation, azimuth and roll angles. The head tracker provides absolute angular and translational position measurements and does not require calibration for each person. The head tracker can operate with multiple receivers allowing for measurement of other important parameters such as hand position in hand-eye coordination studies. Other embodiments that use external signals can include the use of external infrared and ultrasonic signals to detect the position and orientation of the head or other part of the human anatomy.

The mounted head tracker sensor in the head worn/eye worn device can include an IMU of any type cable of being understood by anyone skilled in the art. The mounting of the head tracker can be in the center of the head worn device, or in the nosepiece with eyeglass device or on the sides of the eyeglasses. The head tracker can also be mounted to a removable in-the-mouth appliance, which is fixed to the tooth. It can also be incorporated into a mouth guard or retainer device. The mouth worn device can also generate a sound signal to produce imperceptible sound vibrations that are conducted via the teeth, through bone, to the cochlea and providing the user with signals to move the head.

Another alternative embodiment of the invention is an inertial angular orientation tracking apparatus mounted to the head worn device. Drift sensitive sensors, such as angular rate sensors, produce a signal that is integrated to give a signal that represents angular position. The angular position signal may drift, due to integration of a bias or noise in the output of the rate sensors. To correct this drift, compensating sensors, such as gravimetric tilt sensors and geomagnetic heading sensor(s) can periodically measure the angular position, and this directly measured position signal is used to correct the drift of the integrated position signal. The direct angular position sensors cannot be used alone for dynamic applications because the gravitational sensors are also affected by non-gravitational accelerations, and therefore only accurately reflect angular position when under the influence of no non-gravitational accelerations. Typically, the drift sensitive sensors are angular rate sensors, (these include: rate gyroscopes and vibrating piezoelectric, magneto-hydrodynamic, optical and micro-machined silicon devices) the outputs from which are integrated once. However, other suitable drift sensitive sensors include linear accelerometers used to sense angular rate, gyroscopic angular position sensors and angular accelerometers. Typically, the compensating sensors are inclinometers, accelerometers and compasses.

In another embodiment a head orientation and/or inertial tracking device can be used that is essentially "sourceless", in that it can be used anywhere with no set-up of a source, yet it enables a wider range of virtual environment-style navigation and interaction techniques than does a simple head-orientation tracker, including manual interaction with virtual objects. This device can feature a sourceless orientation tracker including an inertial sensor, a tilt-sensor, or a magnetic compass sensor.

In another embodiment, the device can include a position tracker which includes an acoustic position tracker, an electro-optical system that tracks LEDs, optical sensors or reflective marks, a video machine-vision device, a magnetic tracker with a magnetic source held in the hand and sensors integrated in the headset or vice versa, or a radio frequency position locating device.

In an alternative embodiment, the present invention not only measures VOP (as the VOR or RIS with head movement), but also rehabilitates/retrains the user when an abnormality is present, to enhance the VOR and RIS or retinal visual accuracy with specific visual stimulation and head movements. This rehabilitation can be done for specific vestibulo-ocular pathologic findings. Specifically, when there is an abnormal VOR in the horizontal plane, specific algorithms of eye fixation on a target object, while the head is moving horizontally can be used to rehabilitate the abnormality. When the abnormal VOR is seen in the vertical plane, specific algorithms of eye fixation on a target object, while the head is moving in a vertical manner can be used to rehabilitate the abnormality. As the VOR is enhanced or improved, the DVA or RIS will be enhanced.

In one embodiment, the device or method could provide a sound signal and/or visual signal to alert or trigger the user to respond by moving the eye or head. Remote sensing, see through capability with the head/eye worn device, and the rendering of a visible target in broad daylight are all features that can be incorporated in embodiments of the present technology. The head/eye worn device or method could also collect the data, which could then be uploaded to a medical doctor, trainer, coach or other person at a remote location. This remote location could then provide verbal or visual feedback to the user and this feedback could be integrated with other information provided to the user.

In one embodiment the device or method disclosed here can also be used to help a person improve his or her VOR and DVS and accuracy used during activities in daily living, routine exercise, and high level athletic/vocational activities. This can be used to help a person improve his or her balance by challenging, exercising, enhancing, and/or retraining the VOR (fixation/re-fixation) used during activities in daily living, routine exercise, and high level athletic/vocational activities and therefore improving the retinal visual stability and accuracy of the fovea to remain fixed on the visual element. Thus, embodiments of the present invention can incorporate head movements in one or a number of planes as part of a systematic program for enhancing the VOR and DVA. Using the devices and methods described here it is possible for rehabilitation programs to incorporate head movement with stable image identification and image identification movement with the head remaining stable. The data obtained from the devices and methods described here can be used for wireless communications. The data can be embedded GIS or geographic information system of the eyes or a digital map of where the eyes are located relative to the head movement.

In an embodiment of the present invention, the main functions (head orientation sensing, eye tracking, and the display of an image or images can be performed by a general purpose portable, battery operated, hand held device, such as a smartphone, computer pad, or other wearable computer device. For example, vestibulo-ocular performance could be measured in a virtual environment that was created by attaching a smartphone to a person's head, using the smartphone screen to display stereoscopic images, using the orientation sensors in the smartphone as a head tracker, and using the user-facing video camera to view and track the user's eyes. If the light from the display is insufficient, additional light could be provided by another source that could be operated using infrared (IR) or visible light. Eye tracking could also be enhanced by having the subject wear a contact lens or lenses that have markers on them that would be visible to the smartphone camera. Examples of configurations that could be adapted in this way include Google Cardboard and the Samsung Gear VR. Data on the smartphone could be stored, logged, interpreted, displayed, and/or transmitted to other devices. Transmission of data could use any of the communications technologies available on a typical smartphone including, but not limited to Bluetooth, WiFi, a cellphone signal, or a wired signal. The smartphone based system could also use auditory signals for instructions, audio cues during the test, and/or alarms. This system could be used for passive head movement testing or active head movement testing. Additionally, this portable hand held device or limb worn device can provide a software rehabilitative eye tracking program, if an abnormality is present. This can then enable the person to develop normal or enhanced eye or foveal fixation stability on a target of interest with head rotation or head movement, while performing their occupational activities. Additionally, fiduciary markers can be applied on the head to facilitate inertial head tracking.

It would also be possible for the smartphone to be handheld instead of head-mounted and provide the head orientation sensing, eye tracking, and display functions. Data on the smartphone could also be stored, logged, interpreted, displayed, and/or transmitted to other devices. Transmission of data could use any of the communications technologies available on a typical smartphone including, but not limited to Bluetooth, WiFi, a cellphone signal, or a wired signal. The smartphone-based system could also use auditory signals for instructions, audio cues during the test, and/or alarms. This system could be used for passive head movement testing or active head movement testing.

In one embodiment, the device can be calibrated before it is used to measure VOR. When used in the laboratory setting, calibration can be performed by focusing on a distant target, such as a light bar or laser light which is projected to the wall. The image or visual element moves horizontally, vertically and then is center located. Typically, several trials are performed to establish good reproducible results. During this test, the person is instructed to rotate the head from side to side horizontally or vertically to an auditory cue at frequencies ranging from 2 to 6 Hz. Eye movements are recorded including: direction, amplitude, and velocity of eye movements. Head inertial movements are recorded by the velocity rate sensor attached to the head. Tracking eye movement from spot to spot in this way is called "active tracking". When used in a non-laboratory or a non-clinical setting, similar testing can be performed if there are objects available that will serve the same purpose as the distant target in the laboratory setting. Testing of this type allows gain, phase, and asymmetry to be measured separately at each frequency. A more sophisticated approach would be to ask the subject to follow an object that is not necessarily moving at one specific frequency, but at a combination of frequencies and then using a Fourier transform to convolve the gain, phase, and asymmetry at various frequencies directly from the complex waveform that was being followed by the subject.

As described in the previous paragraph, in some embodiments of the present invention, the head movement tracked and measured can be active. Another approach is to use and measure natural movement that normally occurs during normal activities or activities associated with a person's work and to compare that to the eye movement that occurs at the same time using a Fourier transform. This approach can be called "natural tracking" A third approach is to attach the head to something that then forces the head to move in a specific pattern—which is called "passive tracking."

In embodiments of the present invention, the head movement testing can be used to sense horizontal, vertical or torsional movements at various linear velocities, angular velocities, linear accelerations, angular accelerations, or frequencies. Natural test method testing in the horizontal plane could utilize focusing on a target moving across the horizontal visual field. Watching a moving object ascend and descend in the air would provide a vertical test in a natural manner.

Any combination of the discussed embodiments of head inertial trackers and eye tracking systems can be used to measure the ocular response (e.g. VOR) with head movement. If active tracking is used, the user visualizes a target of interest while moving the head. The target the user is focused on can be seen through a see-through lens (e.g. such as looking at a dot on a wall projected in front of them) or, if wearing other semi-transparent or non-transparent head worn applications (such as a pair of goggles), the target may be displayed as a 3D image, hologram or some other light source image. Video camera eye orientation tracking, using invisible or visible light, simultaneously can be used with head tracking. As the head moves, the ocular responses can be tracked and measured by a variety of modalities. A Fourier transform can be used to compares the inertial head movement and eye movement response at various frequencies in a complex waveform and software can analyze the data. The stored data can be displayed remotely and abnormalities of the related ocular response to the head movement can then predict the performance of the user when performing an occupational activity.

In the prior art, clinicians have looked at the VOR response and made a binary judgment (e.g. the VOR was abnormal or normal). This normal/abnormal criterion would then be used to determine whether vestibular rehabilitation was needed. A better method for evaluating the VOR response would be to measure vestibulo-ocular performance on a continuous scale, just like we measure the speed of an athlete. By doing this, one can get a subject's human performance measurement. Specifically, there can be a VOR response score that more clearly establishes the vestibuloocular response measurement and expresses this response measurement in language that can more appropriately be applied to human performance measurement and improvement. Establishing such a scoring system will enable people to more accurately predict human performance with specific activities. It may also help in the development of activities that improve the human performance in fields where above average VOP is of benefit. The same use of scoring on a continuous scale and multi-frequency composite scoring can apply to DVA, DVS and RIS.

9. Areas of Application

There are many applications for measuring eye responses such as the VOR, DVA and DVS devices and methods here. For example, in sports, the technology described can predict play performance, position performance and it can also be used to help detect and/or assess concussions/TBI to determine whether a player can return to the sport after suffering a hit. Having an abnormal VOR or abnormal DVA can also be used in the pre-selection process for athletes, military personnel, pilot training, or in any other vocational selection process where a high level of human performance is required. The following paragraphs provide greater detail about the use of VOR, DVA, DVS, and other vestibuloocular performance measurements using the embodiments previously described.

Visual acuity tests may be performed using this system in many different ways. It can be a quick way to detect vision problems in schools or for other mass screening (e.g. military recruits, sport applications and other occupations). Within the meaning of this application, any ophthalmic eye-testing device that supplies a predetermined visual stimulus to the person in a predetermined location (which may move) is an automated ophthalmic eye-testing device. In the tests described herein, all of oculomotor responses can be measured in a virtual reality or augmented platform system. Eye and head movement can be tracked as well as that of the eyelid. Eye movement, eye position, visual acuity, pupil function, peripheral and central vision testing can all be easily performed with this technology in these platform systems. These eye activities can be correlated with movement of the extremities to assess hand eye coordination.

Athletics.

Embodiments of the present invention can be used in athletic environments where VOR can help predict performance and early detection of VOR abnormalities and DVA difficulties can be used to identify medical conditions that in a real time environment. Specifically, if a player has an abnormal VOR/DVA in the horizontal plane, that person may not be able to catch a ball when competing in athletic activities that require the head to rotate in a horizontal plane. Similarly, if a player has a vertical VOR/DVA abnormality and is running downfield while looking upwards over the shoulder, the ball will not be in focus. Specifically, the retinal visual stability and accuracy would be diminished. In this instance, there would a higher likelihood of dropping the ball compared to another athlete who has normal VOR responses with normal DVA. If there were a VOR abnormality, which would cause an abnormality of the RIS, seen prior to play, an athlete could do VOR retraining, in an attempt to rectify the abnormality and therefore improve play performance. Alternatively, the coaching staff could select another athlete who did not have this abnormality for specific VOP testing of athletes on the day of play and can predict the likely performance ability of that particular athlete when moving the head in a particular plane of rotation or translation while attempting to fixate on an object such as a ball. For example, on game day if a football player had an abnormal VOR, with resultant decline in the DVA, in the vertical plane (e.g. lack of visual fixation on an object of interest with upwards and downwards movement of the head), then it can be predicted that the athlete is predictable not likely to catch a ball while running downfield and looking upwards over the shoulder (e.g. you cannot catch, what you cannot accurately see). This would offer some value to the coaching staff in selecting plays for the player or players for the necessary play to be performed. Additionally, if an athlete had such an abnormality and could be given some rehabilitation methods prior to play, this could correct the abnormality and increase performance in that activity. Athletes who have had concussions or TBI can have a VOP abnormality, with resultant decrements in the VOR, DVA, or RIS. Embodiments of the present invention can be an accurate method to determine when the athlete is ready to return to play activities, based on improvement of the VOR or DVA. It therefore can be utilized in TBI/concussion evaluation/assessment and management for return to play. It is also intended for athletes who wish to enhance their training and athletic/vocational performance. It can be used in fitness centers, sports training centers, athletic performance centers, and vocational performance centers.

Military personnel functioning in a high-level environment and requiring target fixation of their eyes, while performing other activities such as with head or body movement, require a normal VOR and normal DVA. If the VOR/DVA is abnormal, the individual will not demonstrate peak human performance. Embodiments of the present invention can be used by the military in places such as the pilot selection process or special operations community to aid in the selection of individuals without a VOR/DVA abnormality. VOP measurement could enable other individuals, who had normal retinal visual stability and accuracy, to be chosen for a particular task that has better predictable performance for a particular duty of the day.

Medical.

Similarly, any person with a motion sensitivity disorder (such as motion sickness, vection induced motion sickness, or visually induced motion sickness) or a balance problem, either of a central or peripheral origin, will have a VOR/DVA abnormality. Individuals with such an abnormality will express symptoms of dizziness, disorientation, difficulty with focusing, nausea, fuzziness, and such other complaints as not being clear headed. Embodiments of the present invention can be useful to people who have experienced a vestibular insult, vestibular dysfunction or labyrinthine dysfunction such as those caused by infection, concussive injury, traumatic brain injury, vascular disease, ototoxic or vestibulotoxic medication use, surgical complications, Meniere's disease, people experiencing chronic imbalance, such as, but not limited to, stroke victims, people with systemic illnesses, the elderly and other people who have experienced head injuries, especially those who have experienced cerebral or labyrinthine (inner ear) concussions. It can be used in physician offices to see if a gaze stabilization problem exists and can be useful in the treatment of such an abnormality when it is present. It also can be utilized other centers which perform vestibular rehabilitation and athletic/vocational enhancement environments. This VR/AR system or method described herein can be used as an objective tool for assisting in the diagnosis of traumatic brain injury (TBI), concussion and other degenerative cerebellar disorders that cause highly saccadic results.

Commercial.

Embodiments of the present invention can also be used in other industries where individuals are expected to perform in high activity levels, which may often be also in provocative environments with head/body motion.

Vestibular Rehabilitation.

VOR scoring can also be beneficial in determining who is likely to benefit with vestibular rehabilitation therapy. VOR scoring can also be used more objectively in determining the benefit or improvement with such therapy. The system can include improvement information that can be used by the user, a coach, a medical practitioner, or any other advisor to help interpret the scoring and provide advice and/or exercises to improve ocular reflex. Although vestibular rehabilitation therapy can improve the ocular responses, this scoring can accurately quantify the improvement and more ably predict who is able to return to their normal activity without loss of human performance. Having a VOP score can also provide feedback that helps to control abnormal VOR responses. When an ocular response is abnormal with head rotation (a VOR abnormality, for example), such a finding can also determine a need for improvement with rehabilitation. Repetitive head movement in the abnormal plane of rotation, while the eye remains fixed on a target of interest, can provide a means for improving or enhancing the VOR or other eye responses. Specifically, if a VOR abnormality is found to exist in the horizontal plane, VOR enhancement rehabilitation therapy is given in the same plane. In this instance, the user focuses on a target of interest and the user rotates the head horizontally, while continuing to look at the target. If a VOR abnormality is found to exist in the vertical plane, VOR enhancement rehabilitation therapy is also given in the similar plane of the abnormality. In this instance, the user focuses on a target of interest and the user rotates the head vertically, while continuing to look at the target. The head speed can be varied and the target, which the user is focused, can be changed. The process can be repeated as often as necessary until the VOR abnormality is corrected. This therapy can be performed in any plane where such an abnormality exists. The same use of scoring on a continuous scale and multi-frequency composite scoring can apply to DVA, DVS and MS.

The present invention permits supernormal enhancement of these same systems where no balance disorder exists, as in the case for enhancement of athletic and vocational abilities. Such an enhancement methodology can be used in athletic/vocational enhancement or training and other training environments such as virtual reality training and the like.

While the disclosure has been described with respect to a limited number of embodiments and areas of use, those skilled in the art, having benefit of this disclosure, will appreciate that other embodiments may be devised which do not depart from the scope of the disclosure as disclosed herein. The disclosure has been described in detail, it should be understood that various changes, substitutions and alterations can be made hereto without departing from the spirit and scope of the disclosure.

What is claimed is:

1. A vestibulo-ocular performance measuring device wherein:
    the device is configured for measuring a human physiologic vestibulo-ocular performance characteristic selected from the group of:
    vestibulo-ocular reflex;
    dynamic visual acuity;
    dynamic visual stability;
    kinetic visual acuity;
    retinal image stability; and
    foveal fixation stability; and
    the device comprises:
        an eye orientation sensor wherein:
            the eye orientation sensor is attachable to a person's head;
            the eye orientation sensor comprises a video camera; and
            the eye orientation sensor senses vertical movement and horizontal movement of at least one eye;
        a head orientation sensor wherein:
            the head orientation sensor is attachable to the person's head;
            the head orientation sensor senses pitch and yaw of the person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
            the head orientation sensor senses pitch and yaw in a range of frequencies between 0.01 Hertz and 15 Hertz;
            the head orientation sensor comprises a micro-electro-mechanical system integrated circuit comprising a module selected from the group consisting of an accelerometer, a magnetometer, and a gyroscope;
        an electronic circuit wherein:
            the electronic circuit comprises a battery, a central processing unit, and a memory unit;
            the electronic circuit is responsive to horizontal and vertical eye movement information received from the eye orientation sensor;
            the electronic circuit is responsive to pitch and yaw information received from the head orientation sensor;
            the electronic circuit uses a Fourier transform to generate a vertical gain signal and a vertical phase signal in response to the vertical eye movement information and the pitch information; and
            the electronic circuit uses a Fourier transform to generate a horizontal gain signal and a horizontal phase signal in response to the horizontal eye movement information and the yaw information; and
        a display wherein:
            the display is attachable to the person's head.

2. The device of claim 1; wherein:
    the device is a portable head-worn device configured for use outside of a medical facility;
    the device is self-contained wherein self-contained comprises a configuration that measures the human physiologic vestibulo-ocular performance characteristic without the use of any external devices;
    the video camera is responsive to motion of an eye feature selected from the group of the pupil, the cornea, the iris, the limbus, and the retina;
    the eye orientation sensor senses movement of both the left eye and the right eye;
    the electronic circuit is responsive to both left eye movement information and right eye movement information received from the eye orientation sensor;
    the electronic circuit compares eye movement of one eye in one direction with eye movement of the same eye in the opposite direction to determine eye movement asymmetry;
    the electronic circuit comprises an element that compares a gain signal and a phase signal with a reference value to determine if the measured eye response is normal.

3. The device of claim 2; wherein:
    the eye orientation sensor comprises two separate video cameras, one video camera for sending movement of the left eye and one video camera for sensing movement of the right eye;
    the video cameras are responsive to infrared light;
    the eye orientation sensor senses rotational movement of at least one eye wherein the rotational movement represents a rotation of the eye as viewed by looking at the front of the eye;
    the head orientation sensor comprises a 9-axis inertial measurement unit further comprising an accelerometer, a gyroscope, and a magnetometer;
    the head orientation sensor senses roll of the person's head wherein roll represents a rotation about a third axis substantially orthogonal to the first axis and the second axis representing rotation of the person's face when viewed from the front;
    the battery comprises a lithium ion battery;
    the display comprises a 3-dimensional element;
    the display is responsive to the video camera;
    the electronic circuit is responsive to rotational eye movement information received from the eye orientation sensor;
    the electronic circuit is responsive to roll information received from the head orientation sensor;
    the electronic circuit uses a Fourier transform to generate a rotational gain signal and a rotational phase signal in response to the rotational eye movement information and the roll information;
    the electronic circuit generates a multi-frequency composite score for a measurement selected from the group consisting of vestibulo-ocular reflex, dynamic visual acuity, dynamic visual stability, kinetic visual acuity, retinal image stability, and foveal fixation stability in response to a plurality of signals at a plurality of frequencies selected from the group comprising a plurality of phase signals, a plurality of gain signals, and signals from a plurality of eyes;

the memory unit comprises data logging functionality wherein the data logging functionality stores a plurality of multi-frequency composite scores;

the device comprises a Global Positioning System receiver;

the device comprises a calibration function;

the device comprises vestibulo-ocular performance improvement information for the user; and the display is responsive to the head orientation sensor.

4. A portable eye response measuring system configured for measuring a human physiologic vestibulo-ocular performance characteristic selected from the group of:

vestibulo-ocular reflex;
dynamic visual acuity;
dynamic visual stability;
kinetic visual acuity;
retinal image stability; and
foveal fixation stability, the system comprising:

an eye orientation sensor wherein:
the eye orientation sensor is attachable to a person's head;
the eye orientation sensor comprises a video camera; and
the eye orientation sensor senses movement of at least one eye wherein the eye movement is selected from the group comprising vertical eye movement and horizontal eye movement;

a head orientation sensor wherein:
the head orientation sensor is attachable to a person's head;
the head orientation sensor senses movement of the person's head wherein the head movement is selected from the group comprising pitch movement and yaw movement wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
the head orientation sensor senses movement in a range of frequencies that comprises at least one frequency between 0.01 Hertz and 15 Hertz;
the head orientation sensor comprises a micro-electro-mechanical system integrated circuit comprising a device selected from the group consisting of an accelerometer, a magnetometer, and a gyroscope; and an electronic circuit wherein:
the electronic circuit comprises a central processing unit and a memory unit;
the electronic circuit is responsive to the movement information received from the eye orientation sensor;
the electronic circuit is responsive to the movement information received from the head orientation sensor; and
the electronic circuit generates a signal selected from the group comprising a phase signal and a gain signal in response to eye movement information received from the eye orientation sensor and head movement information received from the head orientation sensor; and a display wherein:
the display is attachable to the person's head.

5. The system of claim 4; wherein:
the system is configurable for use in an ambulatory environment outside of a medical facility;
the eye orientation sensor senses movement of both the left eye and the right eye;
the electronic circuit is responsive to both left eye movement information and right eye movement information received from the eye orientation sensor;
the electronic circuit uses a Fourier transform to generate both the gain signal and the phase signal;
the electronic circuit compares eye movement of one eye in one direction with eye movement of the same eye in the opposite direction to determine eye movement asymmetry;
the electronic circuit comprises an element that compares the gain signal and the phase signal with a reference value to determine if the measured eye response is normal.

6. The system of claim 4; wherein:
the electronic circuit generates a multi-frequency composite score for the human physiologic vestibulo-ocular performance characteristic in response to a plurality of signals at a plurality of frequencies selected from the group consisting of a plurality of phase signals, and a plurality of gain signals.

7. The system of claim 4; wherein:
the eye sensor comprises a mobile electronic device selected from the group comprising a smart phone, a smart watch, a hand-held electronic device, and a body-attached electronic device.

8. The system of claim 4; wherein:
the video camera is responsive to infrared light.

9. The system of claim 4; wherein:
the eye orientation sensor senses vertical movement and horizontal movement of at least one eye;
the head orientation sensor senses pitch and yaw of the person's head;
the electronic circuit uses a Fourier transform to generate a vertical signal selected from the group consisting of a gain signal and a phase signal in response to the vertical eye movement information and the pitch information; and
the electronic circuit uses a Fourier transform to generate a horizontal signal selected from the group consisting of a gain signal and a phase signal in response to the horizontal eye movement information and the yaw information.

10. The system of claim 4; wherein:
the system is configured for detecting neurological damage selected from the group of a concussion and traumatic brain injury.

11. The system of claim 4; wherein:
the display comprises a stereoscopic display; and
the system comprises a virtual reality device.

12. The system of claim 4; wherein:
the system comprises an augmented reality device.

13. The system of claim 4; wherein:
the system is further configured for tests selected from the group of:
vestibulo-ocular performance calibration;
static active vestibulo-ocular performance;
static passive vestibulo-ocular performance;

positional testing;
benign positional paroxysmal vertigo testing;
smooth pursuit testing; and
optokinetic testing.

14. The system of claim 4; wherein:
the system comprises eyewear; and
the eyewear comprises a lens.

15. The system of claim 4; wherein:
the electronic circuit transmits a signal responsive to the eye orientation sensor to a remote device using a wireless communications interface.

16. The system of claim 4 wherein:
the display further comprises a target visual element and a background scene; and
the target visual element has been enhanced with a feature selected from the group comprising:
  a recognizable character;
  a recognizable optotype;
  a feature that moves relative the rest of the target visual element;
  a difference in contrast relative to the background scene;
  a difference in intensity relative to the background scene;
  a difference in focus relative to the background scene; and
  a color that contrasts with the background scene.

17. The system of claim 4; wherein:
the display further comprises a target visual element and a background scene;
the background scene comprises a realistic natural scene; and
the target visual element comprises a moving familiar visual object further comprising a ball.

18. The system of claim 4; wherein:
the display further comprises a target visual element and a background scene;
the background scene is presented in three dimensions;
the target visual element is configured to move relative to the background scene along a scan path comprising variations in movements in three orthogonal axes.

19. The system of claim 4; wherein:
the electronic circuit generates a signal selected from the group comprising:
  a saccade accuracy;
  a saccade amplitude;
  a saccade velocity;
  a saccade latency;
  a saccade duration;
  a visual pursuit accuracy;
  a visual pursuit acceleration;
  a visual pursuit velocity; and
  a visual pursuit latency;
in response to eye movement information received from the eye orientation sensor and head movement information received from the head orientation sensor.

20. A vestibulo-ocular performance measuring method, the method comprising the steps of:
electronically sensing changes in eye orientation wherein:
  the eye orientation changes are sensed by a video camera in a portable device; and
  the eye orientation changes are selected from the group comprising vertical eye movement and horizontal eye movement;
electronically sensing changes in head orientation wherein:
  the head orientation changes are sensed by the portable device;
  the head orientation changes are selected from the group consisting of pitch movement and yaw movement;
  the head orientation changes are sensed in at least one frequency between 0.01 Hertz and 15 Hertz; and
  head orientation sensing comprises the use of a device selected from the group consisting of an accelerometer, a magnetometer, and a gyroscope;
comparing the eye orientation and head orientation information using an electronic circuit wherein:
  the electronic circuit comprises a central processing unit and a memory unit;
  the electronic circuit uses a Fourier transform to generate a signal selected from the group consisting of a phase signal and a gain signal in response to the eye orientation changes and the head orientation changes;
displaying a computer-generated image wherein:
  the image is presented on a display on the portable device; and
measuring a human physiologic vestibulo-ocular performance characteristic selected from the group of:
  vestibulo-ocular reflex;
  dynamic visual acuity;
  dynamic visual stability;
  kinetic visual acuity;
  retinal image stability; and
  foveal fixation stability.

21. The vestibulo-ocular performance measuring method of claim 20; wherein:
the Fourier transform generates the phase signal and the gain signal in response to the eye orientation changes and the head orientation changes;
the method further comprises the step of generating a multi-frequency composite score in response to the signal generated by the Fourier transform.

22. The vestibulo-ocular performance measuring method of claim 20; wherein:
sensing eye orientation changes comprises sensing vertical eye movement and horizontal eye movement;
sensing head orientation changes comprises sensing pitch movement and yaw movement;
the Fourier transform generates a horizontal signal and vertical signal in response to the eye orientation changes and the head orientation changes.

23. The vestibulo-ocular performance measuring method of claim 20; wherein the method is done on a device selected from the group of:
a virtual reality device; and
an augmented reality device.

24. The vestibulo-ocular performance measuring method of claim 20; wherein:
the method is used for improving vestibulo-ocular performance in a rehabilitation environment.

\* \* \* \* \*